United States Patent
Bathe et al.

(10) Patent No.: US 9,624,204 B2
(45) Date of Patent: *Apr. 18, 2017

(54) POLYMORPHIC FORMS OF 1-[4-(5-CYANOINDOL-3-YL)BUTYL]-4-(2-CARBAMOYLBENZOFURAN-5-YL) PIPERAZINE HYDROCHLORIDE

(71) Applicant: Merck Patentgesellschaft, Darmstadt (DE)

(72) Inventors: Andreas Bathe, Darmstadt (DE); Bernd Helfert, Ober-Ramstadt (DE); Steffen Neuenfeld, Messel (DE); Heike Kniel, Heppenheim (DE); Matthias Bartels, Darmstadt (DE); Susanne Rudolph, Dieburg (DE); Henning Bottcher, Darmstadt (DE)

(73) Assignee: Merck Patentgesellschaft, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/549,779

(22) Filed: Nov. 21, 2014

(65) Prior Publication Data
US 2015/0080411 A1 Mar. 19, 2015

Related U.S. Application Data

(60) Continuation of application No. 14/291,931, filed on May 30, 2014, now Pat. No. 8,921,375, which is a continuation of application No. 13/658,088, filed on Oct. 23, 2012, now Pat. No. 8,927,552, which is a continuation of application No. 13/085,117, filed on Apr. 12, 2011, now Pat. No. 8,318,744, which is a continuation of application No. 12/566,835, filed on Sep. 25, 2009, now Pat. No. 7,981,894, which is a division of application No. 12/110,704, filed on Apr. 28, 2008, now Pat. No. 7,834,020, which is a division of application No. 10/481,270, filed as application No. PCT/EP02/06153 on Jun. 5, 2002, now Pat. No. 7,381,726.

(30) Foreign Application Priority Data

Jun. 19, 2001 (EP) .................................... 01113647

(51) Int. Cl.
C07D 405/12 (2006.01)
A61K 31/496 (2006.01)
C07D 405/14 (2006.01)

(52) U.S. Cl.
CPC .......... *C07D 405/12* (2013.01); *A61K 31/496* (2013.01); *C07D 405/14* (2013.01)

(58) Field of Classification Search
None
See application file for complete search history.

(56) References Cited

U.S. PATENT DOCUMENTS

| | | | |
|---|---|---|---|
| 5,521,241 A | 5/1996 | Wu | |
| 5,532,241 A | 7/1996 | Bottcher et al. | |
| 5,723,614 A | 3/1998 | Bathe et al. | |
| 5,977,112 A | 11/1999 | Bathe et al. | |
| 7,381,726 B2 | 6/2008 | Bathe et al. | |
| 7,834,020 B2 | 11/2010 | Bathe et al. | |
| 7,981,894 B2 | 7/2011 | Bathe et al. | |
| 8,193,195 B2 | 6/2012 | Bathe et al. | |
| 8,236,804 B2 | 8/2012 | Bathe et al. | |
| 8,318,744 B2 | 11/2012 | Bathe et al. | |
| 8,673,921 B2 | 3/2014 | Bathe et al. | |
| 2011/0183994 A1 | 7/2011 | Bathe et al. | |
| 2011/0294824 A1 | 12/2011 | Bathe et al. | |
| 2013/0102616 A1 | 4/2013 | Bathe et al. | |

FOREIGN PATENT DOCUMENTS

| | | |
|---|---|---|
| EP | 0648767 A1 | 4/1995 |
| EP | 0738722 A1 | 10/1996 |
| WO | 00/72832 A2 | 12/2000 |
| WO | 02/102794 A2 | 12/2002 |

OTHER PUBLICATIONS

Summary of Facts Regarding US Clinical Trials Prior to Jun. 5, 2001.
Sorbera, L.A. et al. "Vilazodone Hydrochloride. Antidepressant 5-HT.sub.1A Partial Agonist 5-HT Reuptake Inhibitor" Drugs of the Future 2001, 26(3):247-252. (Mar. 2001).
Remington Farmacia Tomo 2 19.sup.a edicion. (1998).
Farmacotecnia Teorica Y Practica Tomo iV, Dr. Jose Heiman. (1980).
Hungarian Search Report of May 10, 2010, citing HU P0201275 which corresponds to WO 00/72832.

(Continued)

*Primary Examiner* — Samantha Shterengarts
(74) *Attorney, Agent, or Firm* — McCarter & English, LLP; Danielle L. Herritt, Esq.; Jin Wang, Esq.

(57) ABSTRACT

The invention relates to new crystalline modifications of the hydrochloride of 1-[4-(5-cyanoindol-3-yl)butyl]-4-(2-carbamoyl-benzofuran-5-yl)-piperazine, crystalline modification of the dihydrochloride of 1-[4-(5-cyanoindol-3-yl)butyl]-4-(2-carbamoyl-benzofuran-5-yl)-piperazine and amorphous 1-[4-(5-cyanoindol-3-yl)butyl]-4-(2-carbamoyl-benzofuran-5-yl)-piperazine hydrochloride which are suitable in particular for the preparation of solid medicaments for the treatment or prevention of depressive disorders, anxiety disorders, bipolar disorders, mania, dementia, substance-related disorders, sexual dysfunctions, eating disorders, obesity, fibromyalgia, sleeping disorders, psychiatric disorders, cerebral infarct, tension, for the therapy of side-effects in the treatment of hypertension, cerebral disorders, chronic pain, acromegaly, hypogonadism, secondary amenorrhea, premenstrual syndrome and undesired puerperal lactation.

27 Claims, 23 Drawing Sheets

(56) References Cited

OTHER PUBLICATIONS

Office Action for U.S. Appl. No. 12/945,260, date of mailing Aug. 17, 2011.
Office Action for U.S. Appl. No. 12/945,272, date of mailing Aug. 17, 2011.
Office Action for U.S. Appl. No. 13/100,911, date of mailing Nov. 9, 2011.
Office Action for U.S. Appl. No. 13/085,117, date of mailing Jan. 13, 2012.
Notice of Allowance for U.S. Appl. No. 12/945,272, date of mailing Mar. 19, 2012.
Corrected Notice of Allowance for U.S. Appl. No. 12/945,272, date of mailing Apr. 3, 2012.
Office Action for U.S. Appl. No. 13/100,911, date of mailing Mar. 23, 2012.
Office Action for U.S. Appl. No. 13/100,911, date of mailing Aug. 17, 2012.
Office Action for U.S. Appl. No. 13/085,117, date of mailing Apr. 3, 2012.
Notice of Allowance for U.S. Appl. No. 13/085,117, date of mailing Aug. 17, 2012.
Office Action for U.S. Appl. No. 13/100,948, date of mailing Nov. 18, 2011.
Office Action for U.S. Appl. No. 13/100,948, date of mailing Mar. 27, 2012.
Notice of Allowance for U.S. Appl. No. 13/100,948, date of mailing Jun. 4, 2012.
Morissette et al. Advanced Drug Delivery Reviews, 2004, 56:275-300.
Notice of Allowance for U.S. Appl. No. 14/032,183, date of mailing Dec. 13, 2013.
Office Action for U.S. Appl. No. 13/658,088, date of mailing May 23, 2013.
Office Action for U.S. Appl. No. 13/658,088, date of mailing Dec. 2, 2013.
U.S. Appl. No. 14/291,931, filed May 30, 2014.

EMD 68843 FORM I (ACETONE SOLVATE)

POLYMORPHIC FORMS OF 1-[4-(5-CYANOINDOL-3-YL)BUTYL]-4-(2-CARBAMOYLBENZOFURAN-5-YL) PIPERAZINE HYDROCHLORIDE

RELATED APPLICATIONS

This application is a continuation application of U.S. patent application Ser. No. 14/291,931, filed May 30, 2014; which is a continuation of U.S. patent application Ser. No. 13/658,088, filed on Oct. 23, 2012; which is a continuation of U.S. patent application Ser. No. 13/085,117, filed Apr. 12, 2011, now U.S. Pat. No. 8,318,744, issued Nov. 27, 2012; which is a continuation application of U.S. patent application Ser. No. 12/566,835, filed Sep. 25, 2009, now U.S. Pat. No. 7,981,894, issued Jul. 19, 2011; which is a divisional application of U.S. patent application Ser. No. 12/110,704, filed Apr. 28, 2008, now U.S. Pat. No. 7,834,020, issued Nov. 16, 2010; which is a divisional application of U.S. patent application Ser. No. 10/481,270, filed Dec. 19, 2003, now U.S. Pat. No. 7,381,726, issued Jun. 3, 2008; which is a national phase application of International Application No. PCT/EP2002/006153, filed Jun. 5, 2002; which claims priority to European Patent Application No. 01113647.0, filed Jun. 19, 2001. The entire contents of each of the foregoing applications and patents are hereby incorporated in their entirety by reference.

FIELD OF THE INVENTION

The present invention relates to novel compounds, to processes for preparing them and to their use in treating medical disorders.

BACKGROUND OF THE INVENTION

1-[4-(5-Cyanoindol-3-yl)butyl]-4-(2-carbamoyl -benzofuran-5-yl)-piperazine, its physiologically acceptable salts thereof (U.S. Pat. No. 5,532,241, column 7, lines 30 to 58), a process (U.S. Pat. No. 5,532,241, Example 4) by which it/they can be prepared and their use in treating certain medical disorders are known from U.S. Pat. No. 5,532,241 and WO 00/72832.

Example 4 of U.S. Pat. No. 5,532,241 describes the preparation of 1-[4-(5-cyanoindol-3-yl)butyl]-4-(2-carbamoyl-benzofuran-5-yl)-piperazine hydrochloride by reacting 1-[4-(5-cyanoindol-3-yl)butyl]-4-(2-carboxybenzofuran-5-yl)piperazine at first with 2-chloro-1-methylpyridinium methanesulfonate in N-methylpyrrolidine and then with dried $NH_3$. Customary working up gives the free base 1-[4-(5-cyanoindol-3-yl)butyl]-4-(2-carboxybenzofuran-5-yl)piperazine. 700 mg of the base are dissolved in 30 ml 2-propanol under heating and then treated with 0.1 n 2-propanolic HCL-solution (Merck-Art. No. 1.00326) until precipitation of hydrochloride is complete. The precipitate was filtered off and washed with diethylether and dried at room temperature to yield 1-[4-(5-cyanoindol-3-yl)butyl]-4-(2-carbamoyl-benzofuran-5-yl)-piperazine hydrochloride having a melting point of 269-272° C. There is no clear teaching elsewhere in the document of any alternative route or modification to the process which would generate new crystal modifications of 1-[4-(5-cyanoindol-3-yl)butyl]-4-(2-carbamoyl-benzofuran-5-yl)-piperazine hydrochloride or new solvates or hydrates of 1-[4-(5-cyanoindol-3-yl)butyl]-4-(2-carbamoyl-benzofuran-5-yl)-piperazine hydrochloride in different crystal modifications.

Former 1-[4-(5-cyanoindol-3-yl)butyl]-4-(2-carbamoyl-benzofuran-5-yl)-piperazine hydrochloride having a melting point of 269-272° C. was a mixture of amorphous 1-[4-(5-cyanoindol-3-yl)butyl]-4-(2-carbamoyl-benzofuran -5-yl)-piperazine hydrochloride, crystallized 1-[4-(5-cyanoindol-3-yl)butyl]-4-(2-carbamoyl-benzofuran-5-yl)-piperazine hydrochloride and the free base 1-[4-(5-cyanoindol-3-yl) butyl]-4-(2-carbamoyl-benzofuran-5-yl)-piperazine.

Certain crystalline, i.e. morphological forms of pharmaceutical compounds may be of interest to those involved in the development of a suitable dosage form because if the morphological form is not held constant during clinical and stability studies, the exact dosage used or measured may not be comparable from one lot to the next. Once a pharmaceutical compound is produced for use, it is important to recognize the morphological form delivered in each dosage form to assure that the production process use the same form and that the same amount of drug is included in each dosage. Therefore, it is imperative to assure that either a single morphological form or some known combination of morphological forms is present. In addition, certain morphological forms may exhibit enhanced thermodynamic stability and may be more suitable than other morphological forms for inclusion in pharmaceutical formulations.

SUMMARY OF THE INVENTION

Methods for preparing pure crystals of 1-[4-(5-cyanoindol-3-yl)butyl]-4-(2-carbamoyl-benzofuran-5-yl)-piperazine hydrochloride have now been found. Furthermore, surprisingly, 1-[4-(5-cyanoindol-3-yl)butyl]-4-(2-carbamoyl-benzofuran-5-yl)-piperazine dihydrochloride, six (five+ dihydrochloride XIII) new forms of 1-[4-(5-Cyanoindol-3-yl)butyl]-4-(2-carbamoyl-benzofuran-5-yl)-piperazine hydrochloride, three new forms of 1-[4-(5-cyanoindol-3-yl) butyl]-4-(2-carbamoyl-benzofuran-5-yl)-piperazine hydrochloride hydrate, six new forms of solvates of 1-[4-(5-cyanoindol-3-yl)butyl]-4-(2-carbamoyl-benzofuran-5-yl)-piperazine hydrochloride and pure amorphous 1-[4-(5-cyanoindol-3-yl)butyl]-4-(2-carbamoyl-benzofuran-5-yl)-piperazine hydrochloride have been found as have processes for their preparation. These forms are hereinafter referred to as I, II, III, IV, V, VI, VII, VIII, IX, X, XI, XIII, XIV, XV and XVI respectively. Throughout the specification, the term "Form" is generally used as a synonym for the term "modification" or "crystalline modification."

Accordingly, the present invention provides solvates of 1-[4-(5-cyanoindol-3-yl)butyl]-4-(2-carbamoyl-benzofuran-5-yl)-piperazine hydrochloride in crystalline modifications and their use for the treatment and prevention of depressive disorders, anxiety disorders, bipolar disorders, mania, dementia, substance-related disorders, sexual dysfunctions, eating disorders, obesity, fibromyalgia, sleeping disorders, psychiatric disorders, cerebral infarct, tension, for the therapy of side-effects in the treatment of hypertension, cerebral disorders, chronic pain, acromegaly, hypogonadism, secondary amenorrhea, premenstrual syndrome and undesired puerperal lactation.

The present invention furthermore provides 1-[4-(5-cyanoindol-3-yl)butyl]-4-(2-carbamoyl-benzofuran-5-yl)-piperazine hydrochloride hydrates in crystalline modifications and their use for the treatment and prevention of depressive disorders, anxiety disorders, bipolar disorders, mania, dementia, substance-related disorders, sexual dysfunctions, eating disorders, obesity, fibromyalgia, sleeping disorders, psychiatric disorders, cerebral infarct, tension, for the therapy of side-effects in the treatment of hypertension, cerebral disorders, chronic pain, acromegaly, hypogonadism, secondary amenorrhea, premenstrual syndrome and undesired puerperal lactation.

The present invention also provides 1-[4-(5-cyanoindol-3-yl)butyl]-4-(2-carbamoyl-benzofuran-5-yl)-piperazine hydrochloride anhydrates in crystalline modifications and their use for the treatment and prevention of depressive disorders, anxiety disorders, bipolar disorders, mania, dementia, substance-related disorders, sexual dysfunctions, eating disorders, obesity, fibromyalgia, sleeping disorders, psychiatric disorders, cerebral infarct, tension, for the therapy of side-effects in the treatment of hypertension, cerebral disorders, chronic pain, acromegaly, hypogonadism, secondary amenorrhea, premenstrual syndrome and undesired puerperal lactation.

The present invention relates additionally to 1-[4-(5-cyanoindol-3-yl)butyl]-4-(2-carbamoyl-benzofuran-5-yl)-piperazine dihydrochloride in its crystalline modification and its use for the treatment and prevention of depressive disorders, anxiety disorders, bipolar disorders, mania, dementia, substance-related disorders, sexual dysfunctions, eating disorders, obesity, fibromyalgia, sleeping disorders, psychiatric disorders, cerebral infarct, tension, for the therapy of side-effects in the treatment of hypertension, cerebral disorders, chronic pain, acromegaly, hypogonadism, secondary amenorrhea, premenstrual syndrome and undesired puerperal lactation.

The present invention relates additionally to pure amorphous 1-[4-(5-cyanoindol-3-yl)butyl]-4-(2-carbamoyl-benzofuran-5-yl)-piperazine hydrochloride and its use for the treatment and prevention of depressive disorders, anxiety disorders, bipolar disorders, mania, dementia, substance-related disorders, sexual dysfunctions, eating disorders, obesity, fibromyalgia, sleeping disorders, psychiatric disorders, cerebral infarct, tension, for the therapy of side-effects in the treatment of hypertension, cerebral disorders, chronic pain, acromegaly, hypogonadism, secondary amenorrhea, premenstrual syndrome and undesired puerperal lactation.

DETAILED DESCRIPTION OF THE INVENTION

Figure 1:
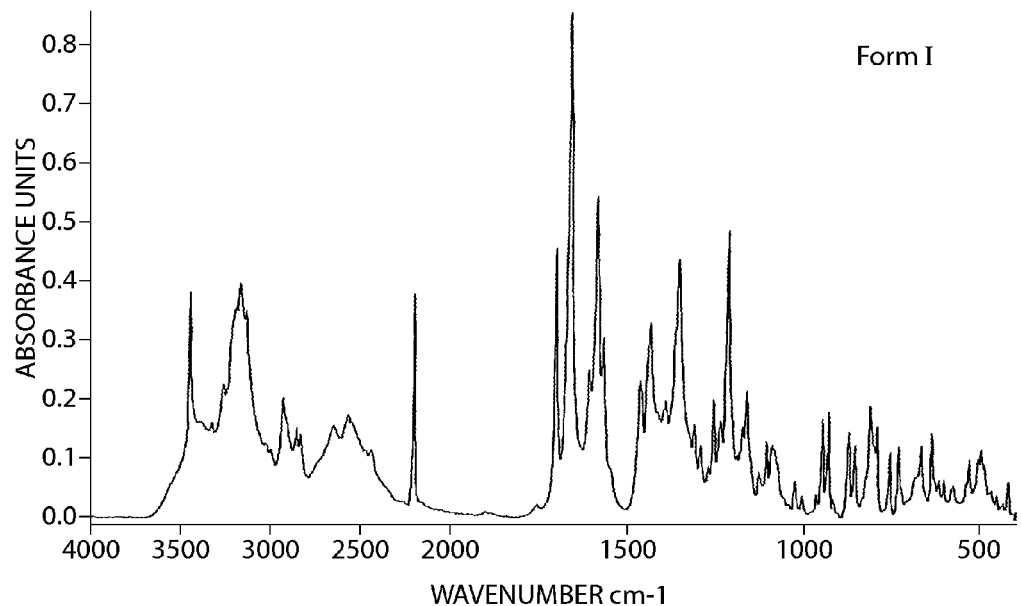
FIG. 1 is an IR absorption spectra of Form I

It has been found that 1-[4-(5-cyanoindol-3-yl)butyl]-4-(2-carbamoyl-benzofuran-5-yl)-piperazine hydrochloride is able to form solvates in crystalline modifications. Examples of such solvates include solvates from water, solvates from alcohols such as methanol, ethanol, propan-1-ol or propan-2-ol; solvates from organic esters such as ethyl acetate; solvates from nitriles such as acetonitrile; solvates from ketones such as acetone and butanone; solvates from ethers such as tetrahydrofuran and solvates from chlorinated hydrocarbons such as chloroform and solvates of hydrocarbons such as n-heptane or toluene. Preferred solvates are formed with polar solvents, preferably water, alcohols, organic esters, nitriles, ketones and ethers.

Preferably, 1-[4-(5-cyanoindol-3-yl)butyl]-4-(2-carbamoyl-benzofuran-5-yl)-piperazine hydrochloride forms solvates with acetone, tetrahydrofuran, methanol, ethyl acetate or n-heptane in crystalline modifications that means the bound solvent together with 1-[4-(5-cyanoindol-3-yl)butyl]-4-(2-carbamoyl-benzofuran-5-yl)-piperazine hydrochloride build the crystal structure. The molar ratio of the solvent to 1-[4-(5-cyanoindol-3-yl)butyl]-4-(2-carbamoyl-benzofuran-5-yl)-piperazine hydrochloride could vary as known to skilled persons in the art. Preferably, the molar ratio is between 0.25:1 to 2.5:1, more preferably between 0.5:1 to 1:1, most preferably 1:1. (n-heptan solvate 1/15:1)

It should be understood that the present solvates of the invention may contain unbound water that is to say water which is other than water of crystallization.

Preferred forms of solvates of 1-[4-(5-cyanoindol-3-yl)butyl]-4-(2-carbamoyl-benzofuran-5-yl)-piperazine hydrochloride include:
  a) 1-[4-(5-cyanoindol-3-yl)butyl]-4-(2-carbamoyl-benzofuran-5-yl)-piperazine hydrochloride solvate with acetone in Form I; (as hereinafter defined),
  b) 1-[4-(5-cyanoindol-3-yl)butyl]-4-(2-carbamoyl-benzofuran-5-yl)-piperazine hydrochloride solvate with tetrahydrofuran in Form II; (as hereinafter defined),
  c) 1-[4-(5-cyanoindol-3-yl)butyl]-4-(2-carbamoyl-benzofuran-5-yl)-piperazine hydrochloride solvate with tetrahydrofuran in Form XV; (as hereinafter defined), d) 1-[4-(5-cyanoindol-3-yl)butyl]-4-(2-carbamoyl-benzofuran-5-yl)-piperazine hydrochloride solvate with tetrahydrofuran in Form X; (as hereinafter defined), e) 1-[4-(5-cyanoindol-3-yl)butyl]-4-(2-carbamoyl-benzofuran-5-yl)-piperazine hydrochloride solvate with methanol in Form XI; (as hereinafter defined), and f) 1-[4-(5-cyanoindol-3-yl)butyl]-4-(2-carbamoyl-benzofuran-5-yl)-piperazine hydrochloride solvate with n-heptane in Form XIV; (as hereinafter defined).

Generally, the specific crystalline forms of the present invention have certain advantages over the product obtained according to U.S. Pat. No. 5,532,241.

Among others, the most important advantages are:
reduced hygroscopicity,
better compressibility during the tablating process,
prolonged shelf life,
better thermodynamic stability, i.e. stability against heat and humidity,
better resistance to sunlight, i.e. UV-light,
increased bulk density,
improved solubility,
bioavailability characteristics which are constant from one batch to the other,
better flow and handling properties in the tableting process,
improved color stability, and
better filtration properties in the production process.

Therefore, by use of the crystalline forms of the present invention, it is possible to obtain galenic formulations having improved homogenicity, stability, purity and uniformity from one batch to the other.

Figure 12:
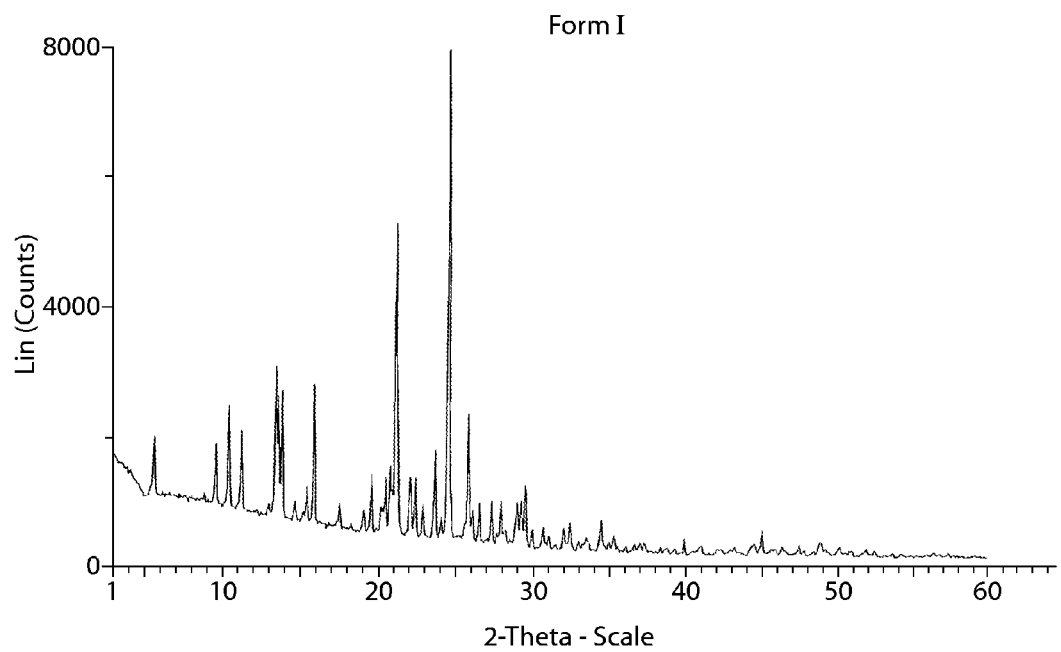
FIG. 12 is an x-ray diffractogram of Form I

Form I according to the invention has the characteristic IR absorption spectra as shown in FIG. 1 and the characteristic X-ray diffraction pattern as shown in FIG. 12. XRD pattern were recorded using a x-ray powder diffractometer (Bruker AXS D5000) in transmission mode (Cu K alpha 1, PSD).

IR absorption spectra were measured in the spectral range 4000-400 $cm^{-1}$ on a Bruker IFS48. Spectral resolution was 2 $cm^{-1}$. Sample preparation was performed generally as KBr disk. The spectra contains additionally a specific acetone absorption band at 1709 $cm^{-1}$.

Figure 28:
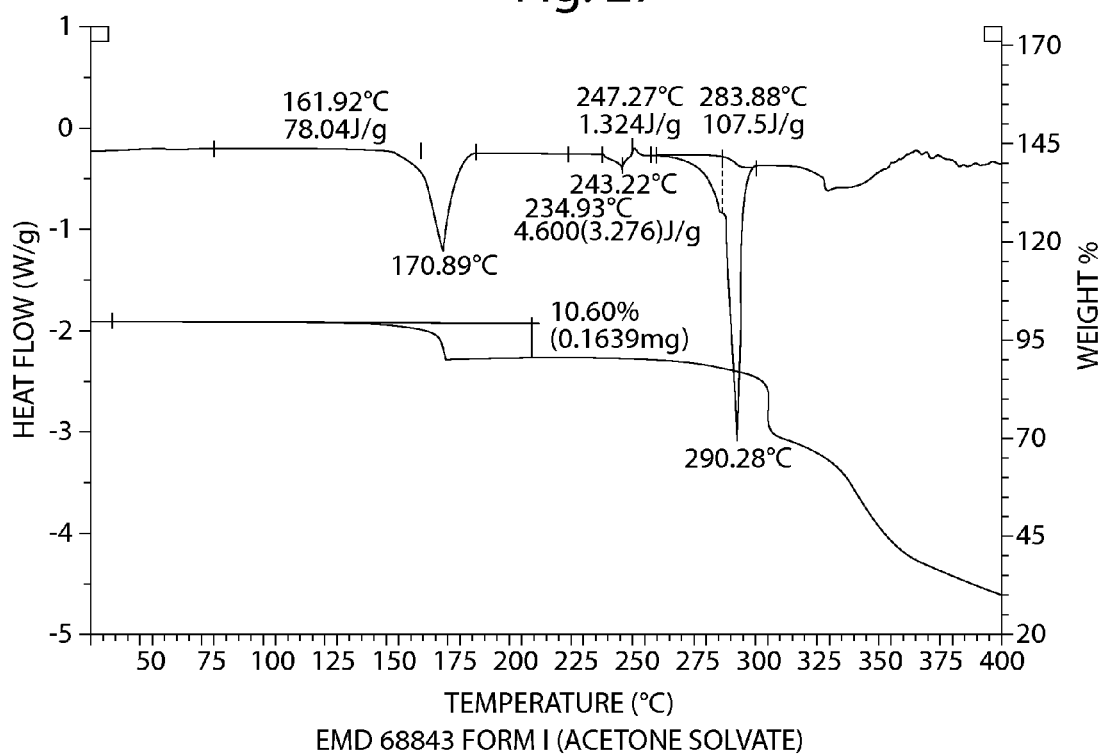
FIG. 28 is a diagram of thermal analysis of Form I

Form I can be further characterized with the aid of thermal analysis measured in the range of 30° to 350° C. FIG. 28 shows the DSC (TA Instruments DSC 2920) and TGA (TA Instruments TGA 2950) measurements. Form I shows a desolvation process between 50° C. and 180° C. Analysis by thermogravimetry showed the presence of 10 weight-% to 11 weight-% of acetone (theory of 1:1 solvate 10.82 weight-%). The DSC measurement gives a phase transition to form VII between 200° C. and 260° C. The thermoanalytically resulting form VII melts between 280° C. and 290° C.

The molar ratio of acetone to 1-[4-(5-cyanoindol-3-yl)butyl]-4-(2-carbamoyl-benzofuran-5-yl)-piperazine hydrochloride in said crystal modification is 1:1, that means the compound of the invention in crystal modification of Form I is 1-[4-(5-cyanoindol-3-yl)butyl]-4-(2-carbamoyl-benzofuran-5-yl)-piperazine hydrochloride monoacetonate.

The invention also provides a process for preparing the above Form I according to the invention, which comprises:
(1) dispersing 1-[4-(5-cyanoindol-3-yl)butyl]-4-(2-carbamoyl-benzofuran-5-yl)-piperazine in acetone,
(2) converting the 1-[4-(5-cyanoindol-3-yl)butyl]-4-(2-carbamoyl-benzofuran-5-yl)-piperazine base, by addition of 1N hydrocloric acid into the hydrochloride salt at temperatures between 30° C. and the boiling point of acetone, preferably between 40° C. and 50° C.,
(3) precipitation of Form I at room temperature, and
(4) recovering the precipitated 1-[4-(5-cyanoindol-3-yl)butyl]-4-(2-carbamoyl-benzofuran-5-yl)-piperazine hydrochloride acetonate by filtration, and drying in vacuo at room temperature.

Alternatively, Form I can be prepared according to a process which comprises:
(1) suspending Form III of 1-[4-(5-cyanoindol-3-yl)butyl]-4-(2-carbamoyl-benzofuran-5-yl)-piperazine hydrochloride, which will be described later in detail, in acetone,
(2) stirring at room temperature between a few hours or days, preferably 10 to 20 days, and
(3) recovering the precipitated 1-[4-(5-cyanoindol-3-yl)butyl]-4-(2-carbamoyl-benzofuran-5-yl)-piperazine hydrochloride solvate with tetrahydrofuran by filtration, and drying in vacuo at room temperature.

Figure 2:
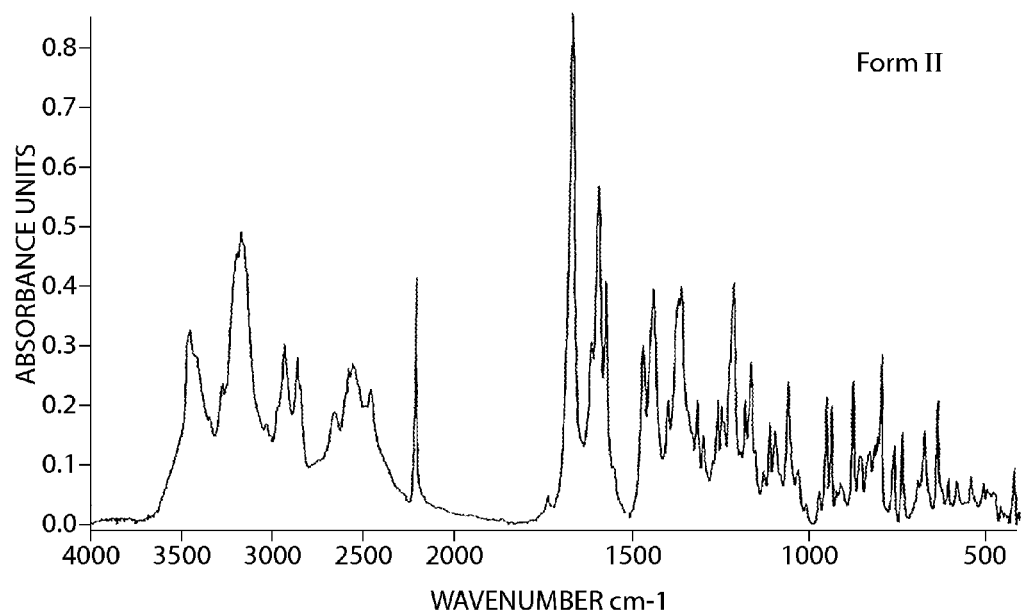
FIG. 2 is an IR absorption spectra of Form II
Figure 13:
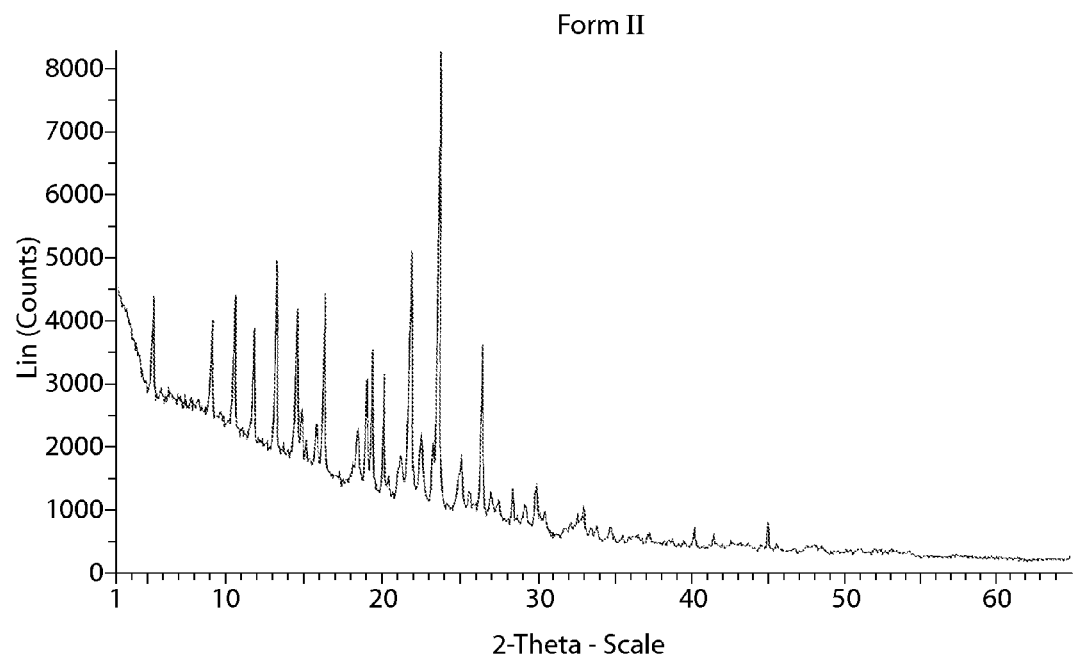
FIG. 13 is an x-ray diffractogram of Form II

Form II according to the invention has the characteristic IR absorption spectra as shown in FIG. 2 and the characteristic X-ray diffraction pattern as shown in FIG. 13. XRD pattern were recorded using a x-ray powder diffractometer (Bruker AXS D5000) in transmission mode (Cu K alpha 1, PSD).

IR absorption spectra were measured in the spectral range 4000-400 $cm^{-1}$ on a Bruker IFS48. Spectral resolution was 2 $cm^{-1}$. The spectra as shown in the figures were converted to transmission.

Figure 29:
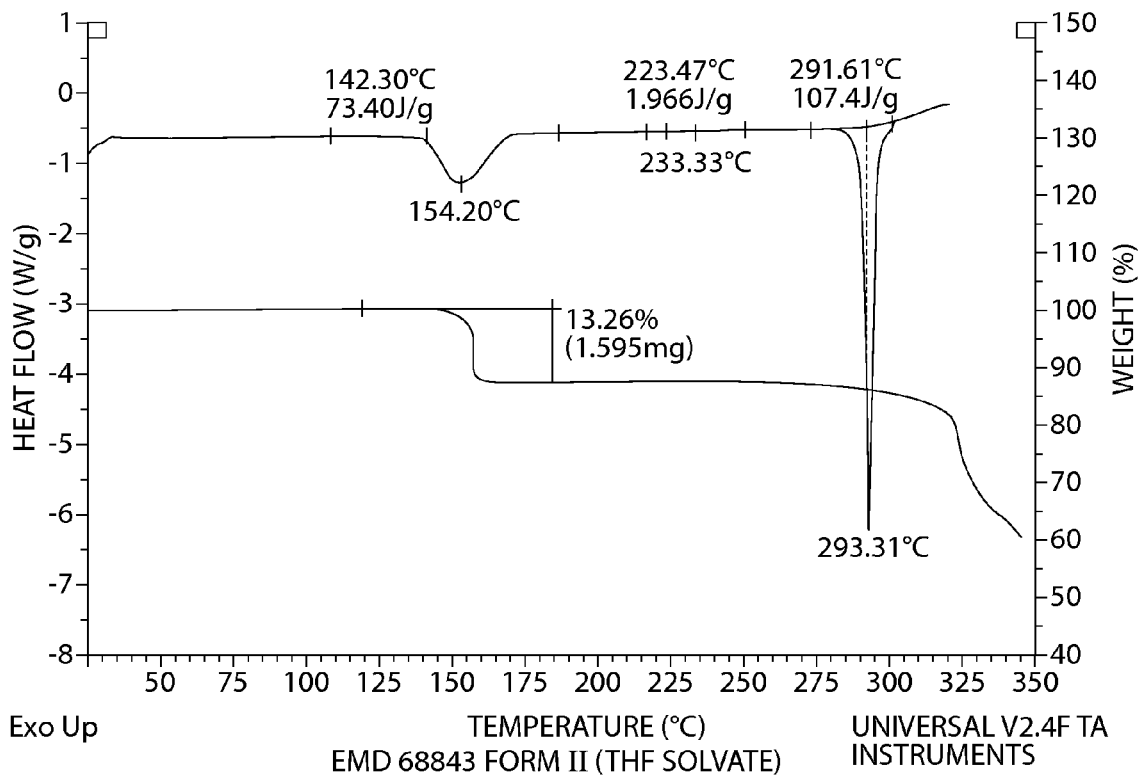
FIG. 29 is a diagram of thermal analysis of Form II

Form II can be further characterized with the aid of thermal analysis measured in the range of 30° to 350° C. FIG. 29 shows the DSC (TA Instruments DSC 2920) and TGA (TA Instruments TGA 2950) measurements. Form II shows a desolvation process between 120° C. and 180° C. Analysis by thermogravimetry showed the presence of 13 weight-% to 14 weight-% of THF (theory of 1:1 solvate 13.11 weight-%). The DSC measurement gives a phase transition to form VII between 200° C. and 260° C. The thermoanalytically resulting form VII melts between 280° C. and 290° C.

The molar ratio of tetrahydrofuran to 1-[4-(5-cyanoindol-3-yl)butyl]-4-(2-carbamoyl-benzofuran-5-yl)-piperazine hydrochloride in said crystal modification is 1:1, that means the compound of the invention in crystal modification of Form II is a monosolvate of 1-[4-(5-cyanoindol-3-yl)butyl]-4-(2-carbamoyl-benzofuran-5-yl)-piperazine hydrochloride with tetrahydrofuran.

The invention also provides a process for preparing the above Form II according to the invention, which comprises:
(1) dispersing 1-[4-(5-cyanoindol-3-yl)butyl]-4-(2-carbamoyl-benzofuran-5-yl)-piperazine in tetrahydrofuran,
(2) converting the 1-[4-(5-cyanoindol-3-yl)butyl]-4-(2-carbamoyl-benzofuran-5-yl)-piperazine base, by addition of 1N hydrochloric acid into the hydrochloride salt at temperatures between 10° C. and 60° C., preferably between 20° C. and 30° C.,
(3) precipitation of Form II between −10° C. and 10° C., and
(4) recovering the precipitated 1-[4-(5-cyanoindol-3-yl)butyl]-4-(2-carbamoyl-benzofuran-5-yl)-piperazine hydrochloride solvate with tetrahydrofuran by filtration, and drying in vacuo at room temperature.

Alternatively, Form II can be prepared according to a process which comprises:
(1) suspending Form III of 1-[4-(5-cyanoindol-3-yl)butyl]-4-(2-carbamoyl-benzofuran-5-yl)-piperazine hydrochloride, which will be described later in detail, in tetrahydrofuran, (2) stirring at room temperature between a few hours or days, preferably 15 to 30 days, and (3) recovering the precipitated 1-[4-(5-cyanoindol-3-yl)butyl]-4-(2-carbamoyl-benzofuran-5-yl)-piperazine hydrochloride acetonate by filtration, and drying in vacuo at room temperature.

Figure 3:
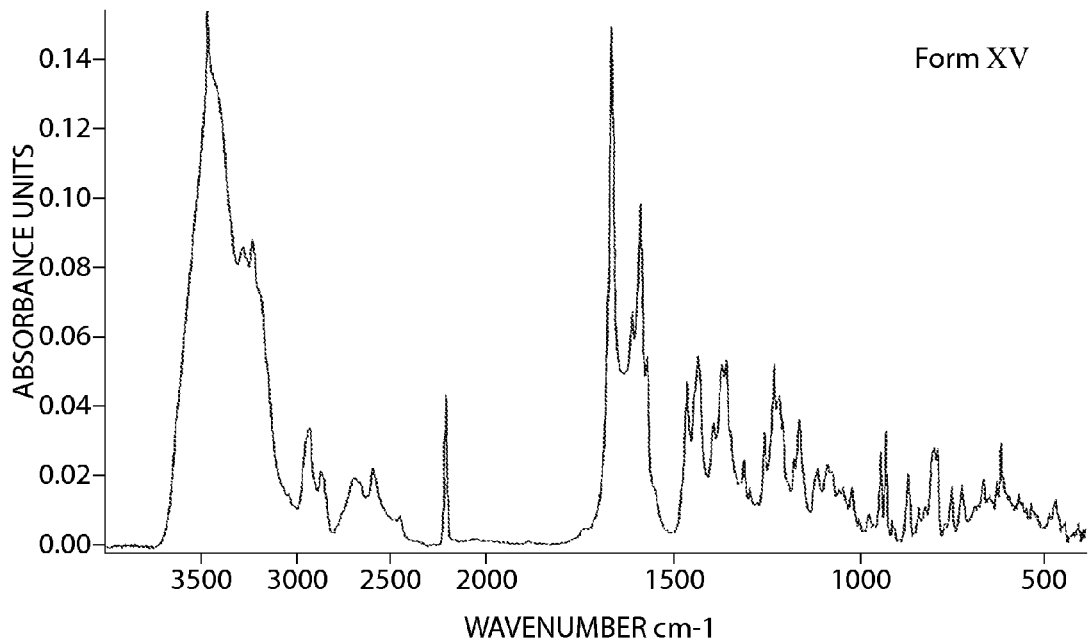
FIG. 3 is an IR absorption spectra of Form XV
Figure 14:
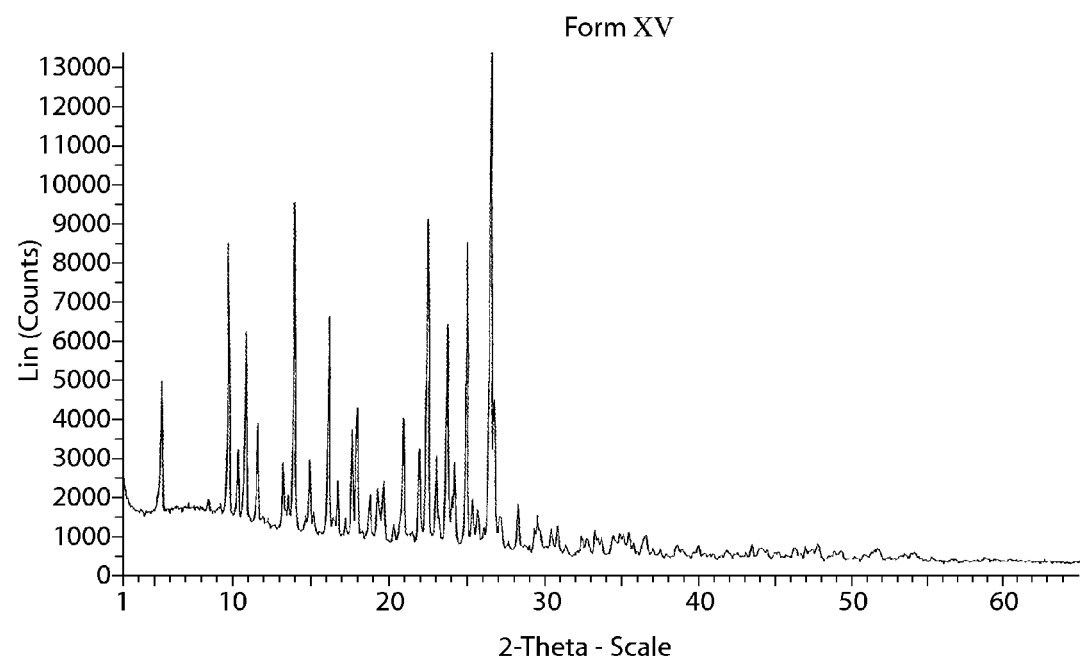
FIG. 14 is an x-ray diffractogram of Form XV

Form XV according to the invention has the characteristic IR absorption spectra as shown in FIG. 3 and the characteristic X-ray diffraction pattern as shown in FIG. 14. XRD pattern were recorded using a x-ray powder diffractometer (Bruker AXS D5000) in transmission mode (Cu K alpha 1, PSD).

IR absorption spectra were measured in the spectral range 4000-400 cm$^{-1}$ on a Bruker IFS48. Spectral resolution was 2 cm$^{-1}$. The spectra as shown in the figures were converted to transmission.

Figure 39:
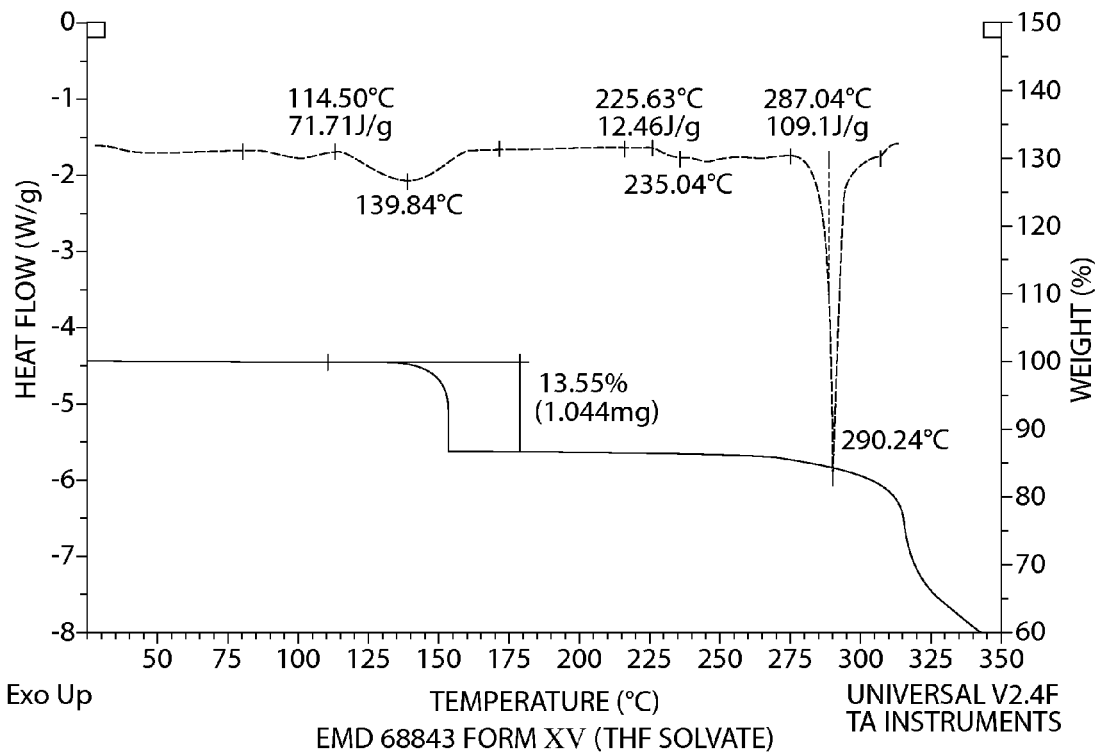
FIG. 39 is a diagram of thermal analysis of Form XV
Figure 40:
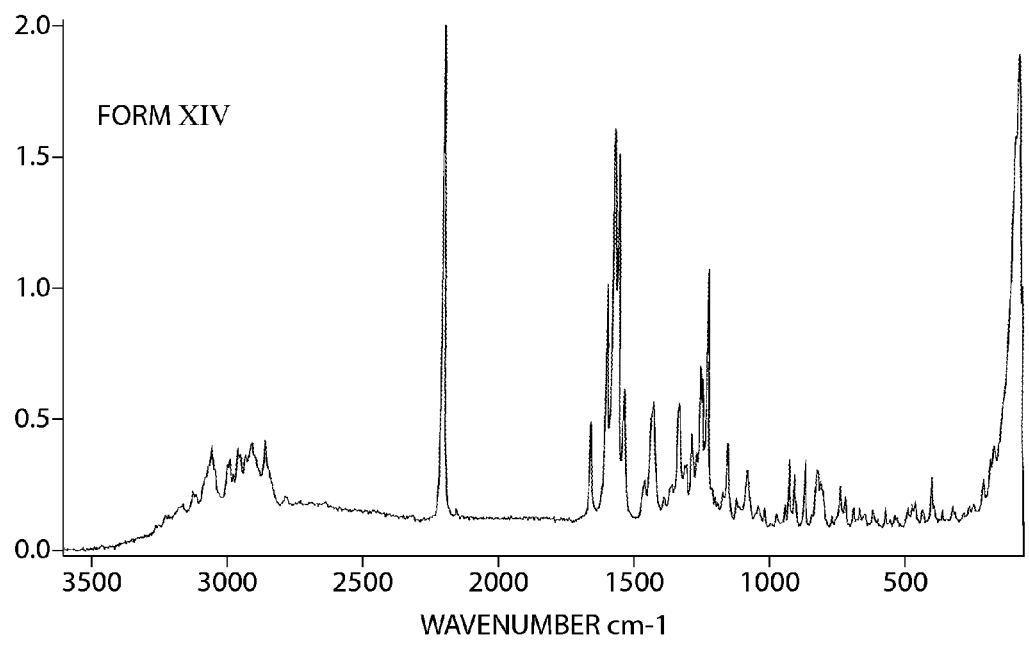
FIG. 40 is a Raman spectra of Form XIV
Figure 41:
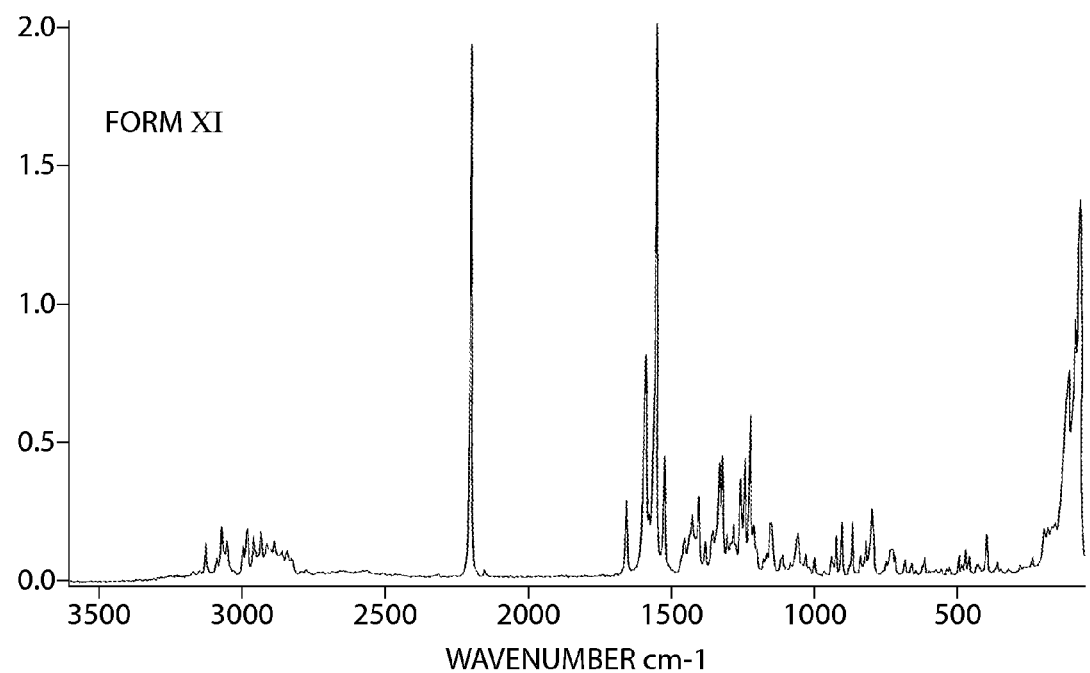
FIG. 41 is a Raman spectra of Form XI
Figure 42:
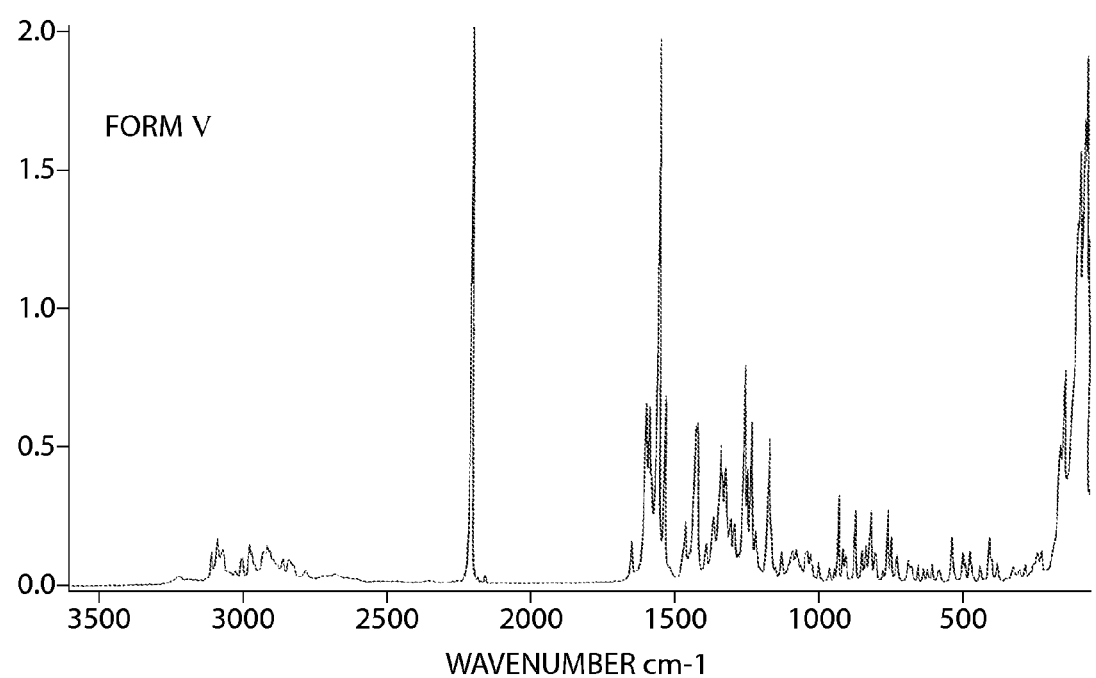
FIG. 42 is a Raman spectra of Form V
Figure 43:
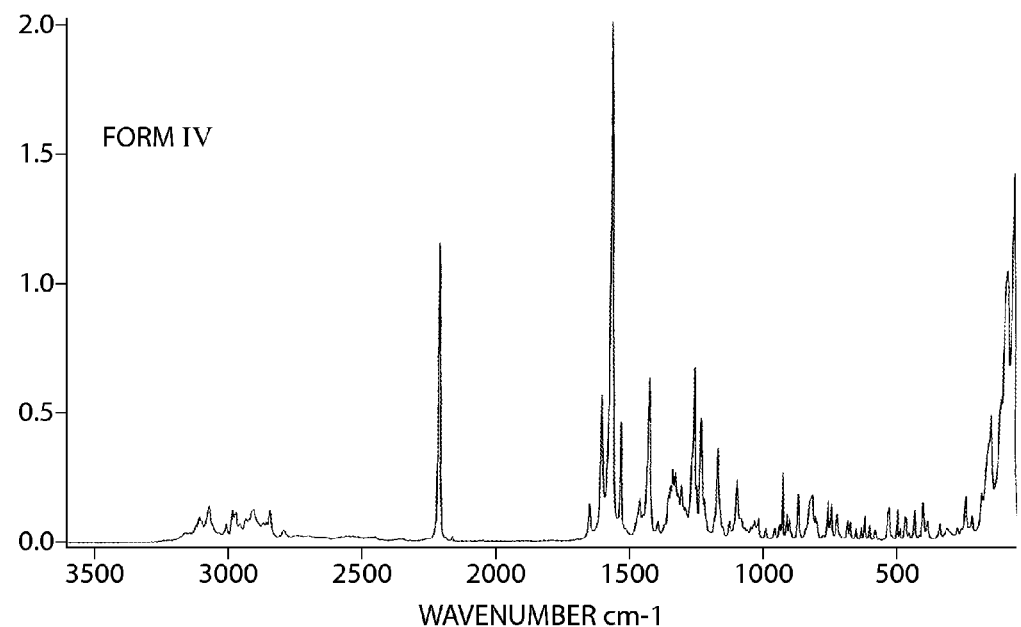
FIG. 43 is a Raman spectra of Form IV
Figure 44:
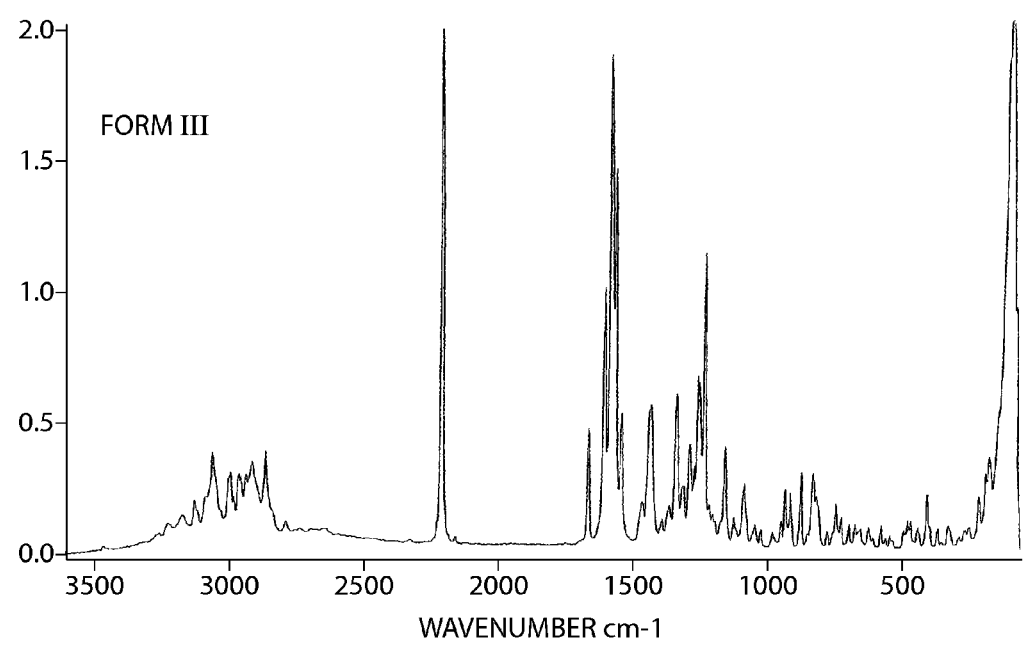
FIG. 44 is a Raman spectra of Form III
Figure 45:
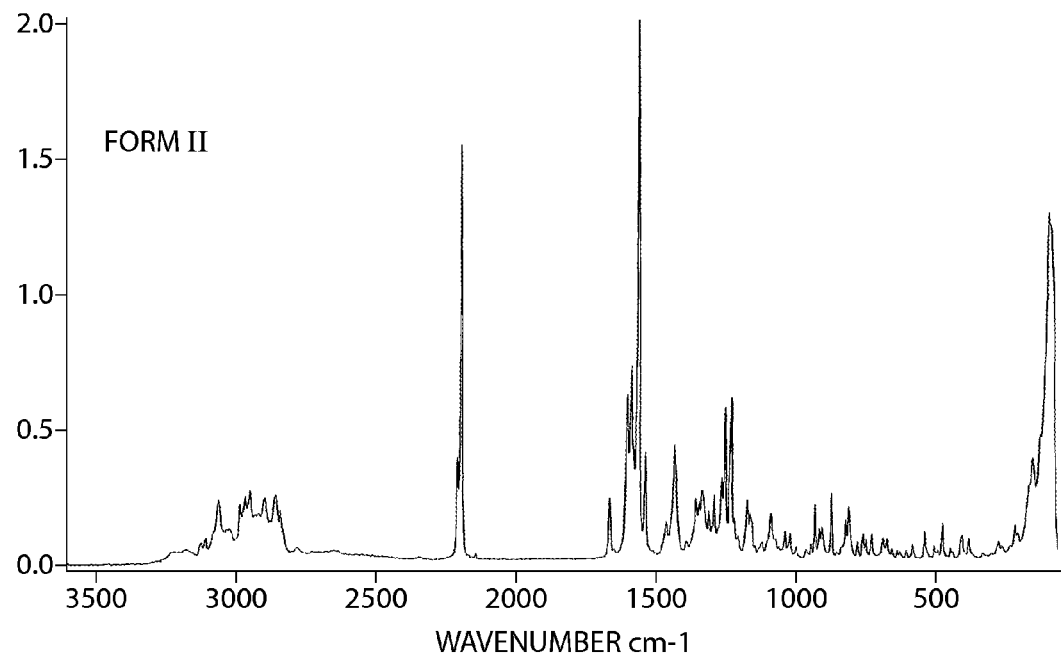
FIG. 45 is a Raman spectra of Form II
Figure 46:
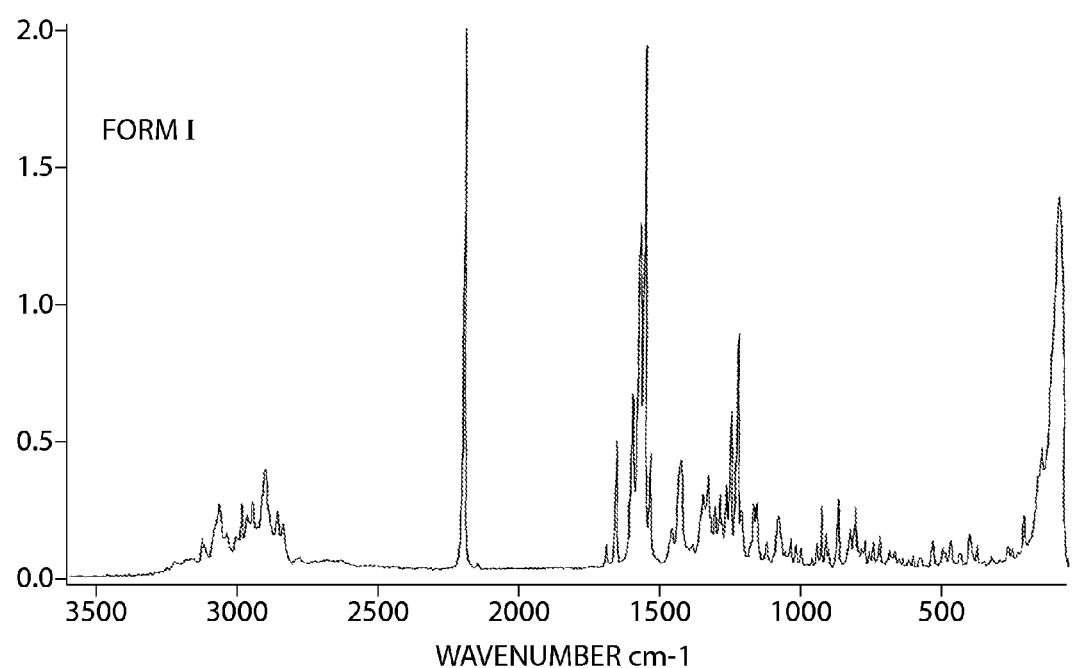
FIG. 46 is a Raman spectra of Form I

Form XV can be further characterized with the aid of thermal analysis measured in the range of 30° to 350° C. FIG. 39 shows the DSC (TA Instruments DSC 2920) and TGA (TA Instruments TGA 2950) measurements. Form XV shows a desolvation process between 75° C. and 180° C. Analysis by thermogravimetry showed the presence of 13 weight-% to 14 weight-% of THF (theory of 1:1 solvate 13.11 weight-%). The DSC measurement gives a phase transition to form VII between 200° C. and 260° C. The thermoanalytically resulting form VII melts between 280° C. and 290° C. The molar ratio of tetrahydrofuran to 1-[4-(5-cyanoindol-3-yl)butyl]-4-(2-carbamoyl-benzofuran-5-yl)-piperazine hydrochloride in said crystal modification is 1:1, that means the compound of the invention in crystal modification of Form XV is a monosolvate of 1-[4-(5-cyanoindol-3-yl)butyl]-4-(2-carbamoyl-benzofuran-5-yl)-piperazine hydrochloride with tetrahydrofuran.

The invention also provides a process for preparing the above Form XV according to the invention, which comprises:

(1) dispersing 1-[4-(5-cyanoindol-3-yl)butyl]-4-(2-carbamoyl-benzofuran-5-yl)-piperazine in tetrahydrofuran, (2) converting the 1-[4-(5-cyanoindol-3-yl)butyl]-4-(2-carbamoyl-benzofuran-5-yl)-piperazine base, by addition of 1N hydrochloric acid into the hydrochloride salt at temperatures between −10° C. and 10° C., preferably between −5° C. and +5° C., (3) precipitation of Form XV at room temperature, and (4) recovering the precipitated 1-[4-(5-cyanoindol-3-yl)butyl]-4-(2-carbamoyl-benzofuran-5-yl)-piperazine hydrochloride solvate with tetrahydrofuran by filtration, and drying in vacuo at room temperature.

Figure 15:
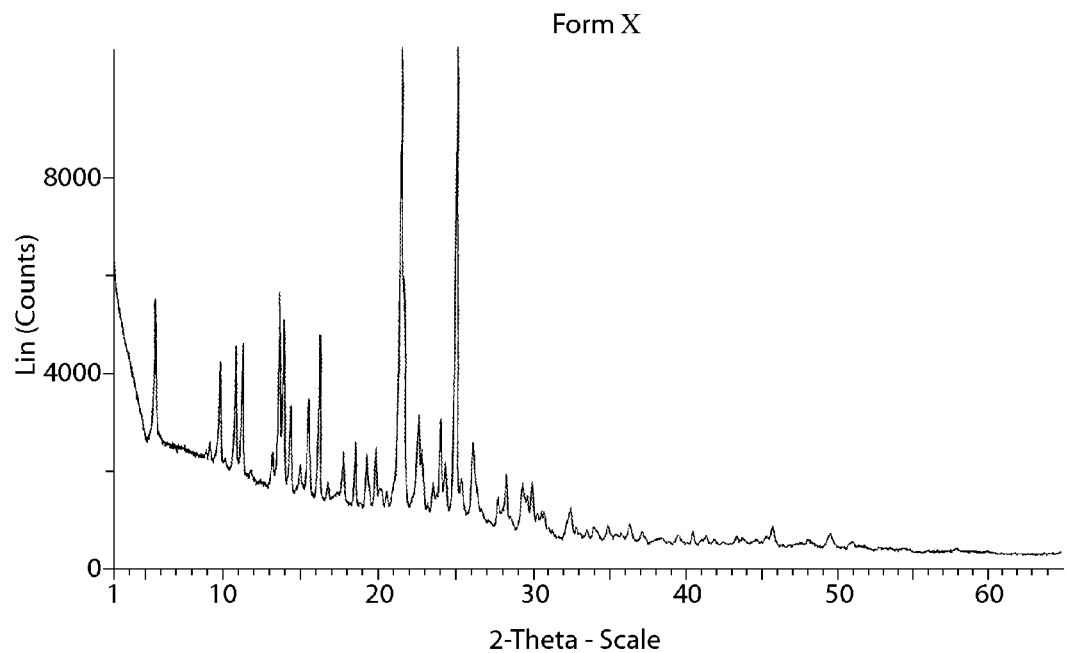
FIG. 15 is an x-ray diffractogram of Form X

Form X according to the invention has the characteristic X-ray diffraction pattern as shown in FIG. 15. XRD pattern were recorded using a x-ray powder diffractometer (Bruker AXS D5000) in transmission mode (Cu K alpha 1, PSD).

The molar ratio of tetrahydrofuran to 1-[4-(5-cyanoindol-3-yl)butyl]-4-(2-carbamoyl-benzofuran-5-yl)-piperazine hydrochloride in said crystal modification is 0.5:1, that means the compound of the invention in crystal modification of Form X is a hemisolvate of 1-[4-(5-cyanoindol-3-yl)butyl]-4-(2-carbamoyl-benzofuran-5-yl)-piperazine hydrochloride with tetrahydrofuran.

The invention also provides a process for preparing the above Form X according to the invention, which comprises:

(1) dispersing 1-[4-(5-cyanoindol-3-yl)butyl]-4-(2-carbamoyl-benzofuran-5-yl)-piperazine in tetrahydrofuran, (2) converting the 1-[4-(5-cyanoindol-3-yl)butyl]-4-(2-carbamoyl-benzofuran-5-yl)-piperazine base, by addition of 1N hydrochloric acid into the hydrochloride salt at temperatures between 10° C. and 40° C., preferably between 20° C. and 30° C., (3) precipitation of Form X at room temperature, and (4) recovering the precipitated 1-[4-(5-cyanoindol-3-yl)butyl]-4-(2-carbamoyl-benzofuran-5-yl)-piperazine hydrochloride solvate with tetrahydrofuran by filtration, and drying at temperatures up to 80° C. maximum.

Figure 4:
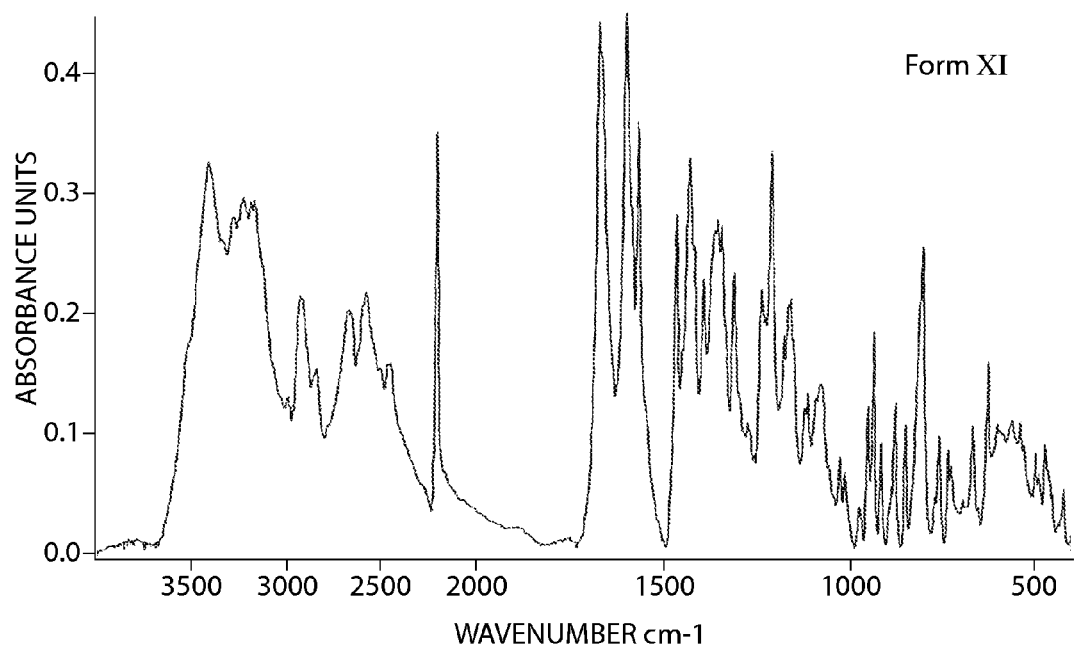
FIG. 4 is an IR absorption spectra of Form XI
Figure 16:
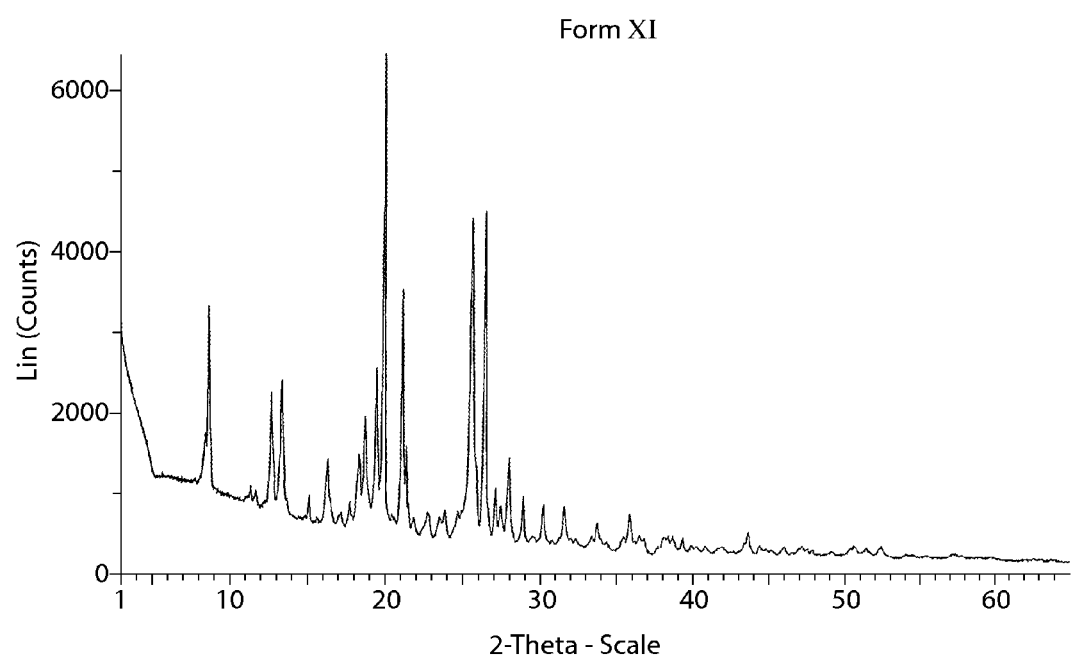
FIG. 16 is an x-ray diffractogram of Form XI

Form XI according to the invention has the characteristic IR absorption spectra as shown in FIG. 4 and the characteristic X-ray diffraction pattern as shown in FIG. 16. XRD pattern were recorded using a x-ray powder diffractometer (Bruker AXS D5000) in transmission mode (Cu K alpha 1, PSD).

IR absorption spectra were measured in the spectral range 4000-400 cm$^{-1}$ on a Bruker IFS48. Spectral resolution was 2 cm$^{-1}$. The spectra as shown in the figures were converted to transmission.

Figure 37:
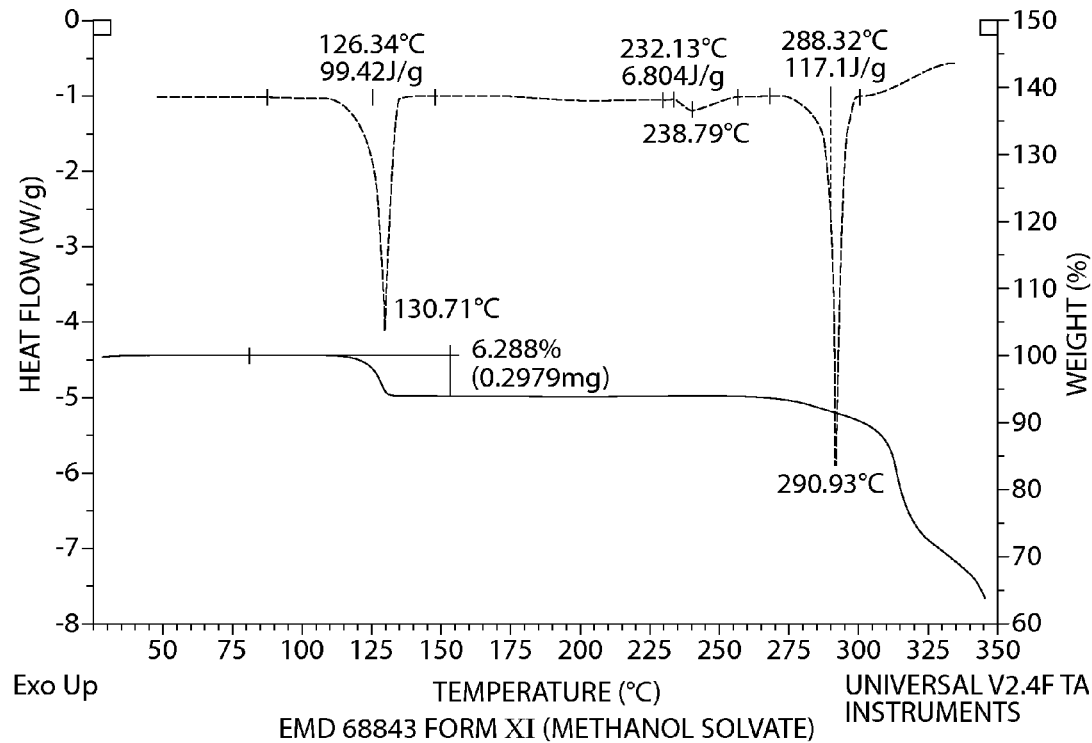
FIG. 37 is a diagram of thermal analysis of Form XI

Form XI can be further characterized with the aid of a thermal analysis measured in the range of 30° to 350° C. FIG. 37 shows the DSC (TA Instruments DSC 2920) and TGA (TA Instruments TGA 2950) measurements. Form XI shows a desolvation process between 75° C. and 150° C. Analysis by thermogravimetry showed the presence of 6 weight-weight-% to 7 weight-weight-% of methanol (theory of 1:1 solvate 6.28 weight-%). The DSC measurement gives a phase transition to form VII between 200° C. and 260° C. The thermoanalytically resulting form VII melts between 280° C. and 290° C.

The molar ratio of methanol to 1-[4-(5-cyanoindol-3-yl)butyl]-4-(2-carbamoyl-benzofuran-5-yl)-piperazine hydrochloride in said crystal modification is 1:1, that means the compound of the invention in the crystalline modification of Form XI is a monosolvate of 1-[4-(5-cyanoindol-3-yl)butyl]-4-(2-carbamoyl-benzofuran-5-yl)-piperazine hydrochloride with methanol.

The invention also provides a process for preparing the above Form XI according to the invention, which comprises:

(1) suspending Form VI of 1-[4-(5-cyanoindol-3-yl)butyl]-4-(2-carbamoyl-benzofuran-5-yl)-piperazine hydrochloride, which will be described later in detail, in methanol at temperatures between 55° C. and the boiling point of methanol, (2) cooling down the reaction mixture to temperatures between −40° and −10° C., preferably to −30° C., and (3) recovering the precipitated 1-[4-(5-cyanoindol-3-yl)butyl]-4-(2-carbamoyl-benzofuran-5-yl)-piperazine hydrochloride methanolate by filtration at room temperature, and drying in vacuo at room temperature.

Figure 5:
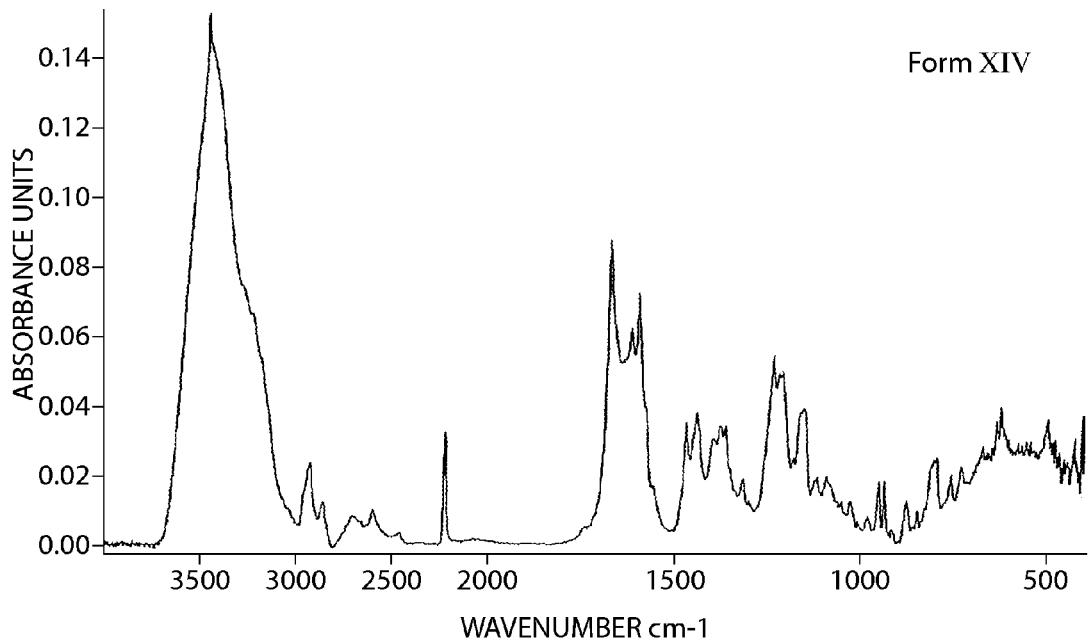
FIG. 5 is an IR absorption spectra of Form XIV
Figure 17:
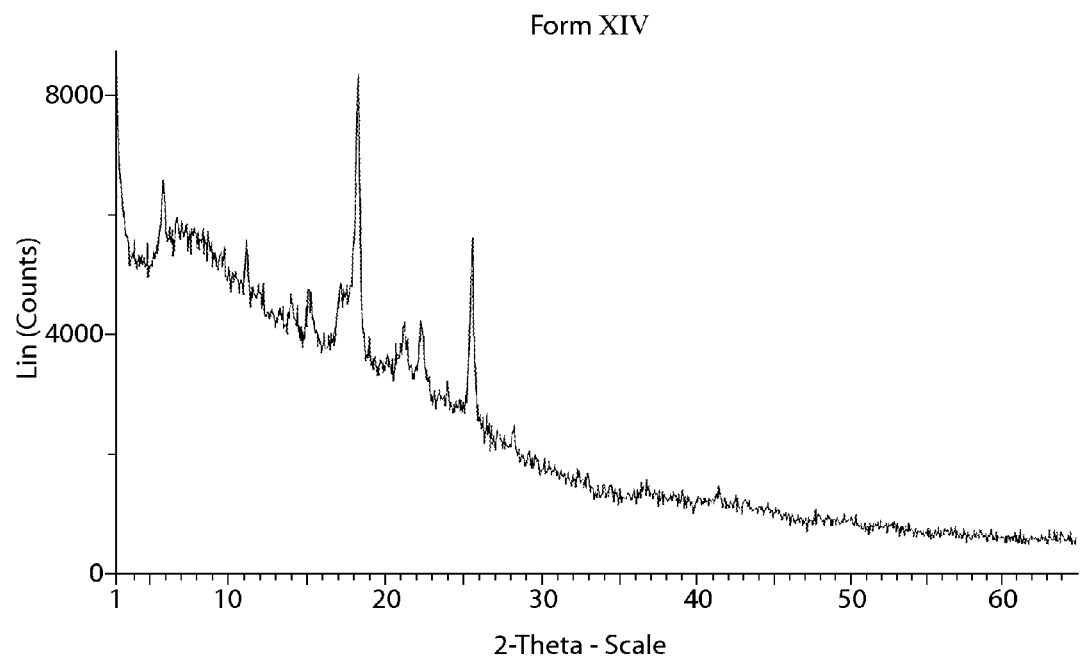
FIG. 17 is an x-ray diffractogram of Form XIV

Form XIV according to the invention has the characteristic IR absorption spectra as shown in FIG. 5 and the characteristic X-ray diffraction pattern as shown in FIG. 17. XRD pattern were recorded using a x-ray powder diffractometer (Bruker AXS D5000) in transmission mode (Cu K alpha 1, PSD).

IR absorption spectra were measured in the spectral range 4000-400 cm$^{-1}$ on a Bruker IFS48. Spectral resolution was 2 cm$^{-1}$. The spectra as shown in the figures were converted to transmission.

Figure 38:
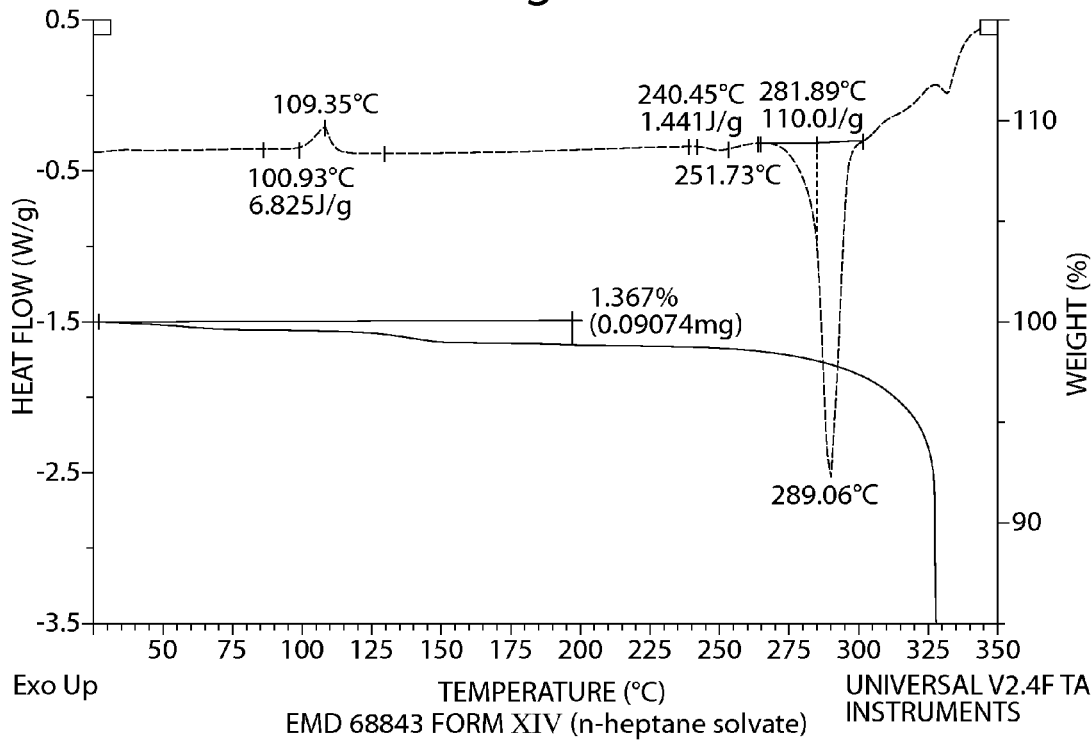
FIG. 38 is a diagram of thermal analysis of Form XIV

Form XIV can be further characterized with the aid of a thermal analysis measured in the range of 30° C. and 350° C. FIG. 38 shows the DSC (TA Instruments DSC 2920) and TGA (TA Instruments TGA 2950) measurements. Analysis by thermogravimetry showed the presence of 1 weight-% to 3 weight-% of n-heptane (theory of 15:1 solvate 1.37 weight-%, theory of 10:1 solvate 2.05 weight-%).

The molar ratio of n-heptane to 1-[4-(5-cyanoindol-3-yl)butyl]-4-(2-carbamoyl-benzofuran-5-yl)-piperazine hydrochloride in said crystal modification is between 1:10 and 1:15, that means the compound of the invention in crystal modification of Form XIV is a solvate of 1-[4-(5-cyanoindol-3-yl)butyl]-4-(2-carbamoyl-benzofuran-5-yl)-piperazine hydrochloride with n-heptane. The DSC measurement gives phase transitions between 80° C. and 120° C. and between 200° C. and 260° C. The thermoanalytically resulting form VII melts between 280° C. and 290° C.

The invention also provides a process for preparing the above Form XIV according to the invention, which comprises:
(1) suspending Form III of 1-[4-(5-cyanoindol-3-yl)butyl]-4-(2-carbamoyl-benzofuran-5-yl)-piperazine hydrochloride, which will be described later in detail, in n-heptane,
(2) stirring at room temperature between a few hours or days, preferably 15 to 30 days, and
(3) recovering the precipitated solvate of 1-[4-(5-cyanoindol-3-yl)butyl]-4-(2-carbamoyl-benzofuran-5-yl)-piperazine hydrochloride with n-heptane by filtration, and drying in vacuo at room temperature.

Additionally, it has been found that 1-[4-(5-cyanoindol-3-yl)butyl]-4-(2-carbamoyl-benzofuran-5-yl)-piperazine hydrochloride is able to form hydrates in crystalline modifications. Preferably, the molar ratio of water to 1-[4-(5-cyanoindol-3-yl)butyl]-4-(2-carbamoyl-benzofuran-5-yl)-piperazine hydrochloride is between 0.25:1 to 2.5:1, more preferably between 0.5:1 to 1:1, most preferably 1:1.

It should be understood that the present hydrates of the invention may contain unbound water that is to say water which is other than water of crystallization.

Preferred forms of hydrates of 1-[4-(5-cyanoindol-3-yl)butyl]-4-(2-carbamoyl-benzofuran-5-yl)-piperazine hydrochloride include:
a) 1-[4-(5-cyanoindol-3-yl)butyl]-4-(2-carbamoyl-benzofuran-5-yl)-piperazine hydrochloride monohydrate in Form V; (as hereinafter defined),
b) 1-[4-(5-cyanoindol-3-yl)butyl]-4-(2-carbamoyl-benzofuran-5-yl)-piperazine hydrochloride in Form VI; (as hereinafter defined), and
c) 1-[4-(5-cyanoindol-3-yl)butyl]-4-(2-carbamoyl-benzofuran-5-yl)-piperazine hydrochloride hemihydrate in Form VIII; (as hereinafter defined).

Figure 6:
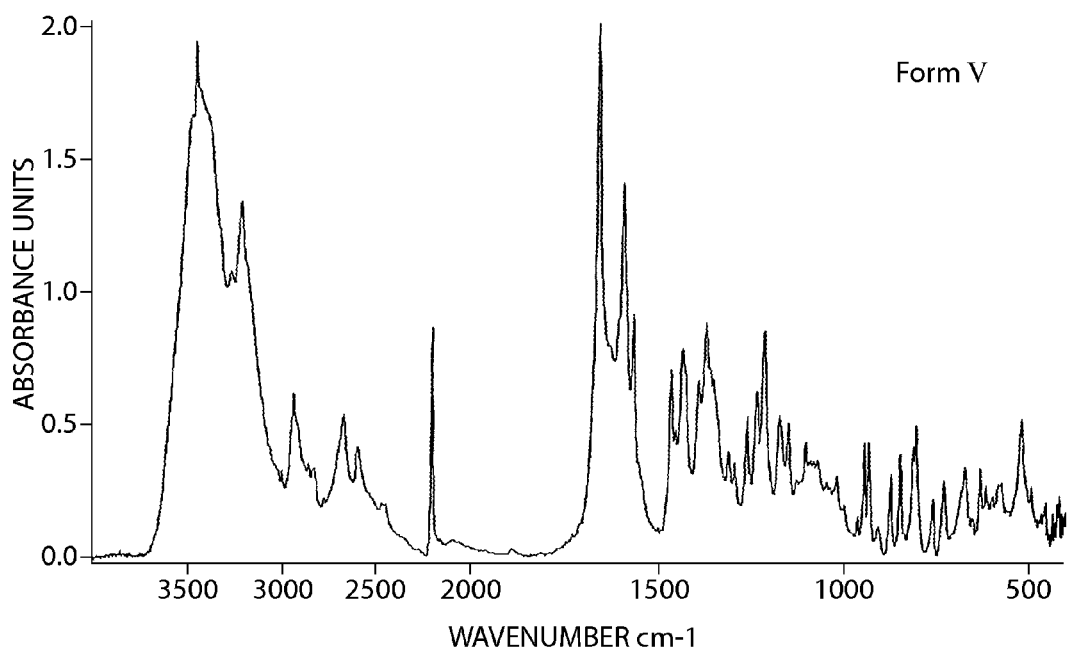
FIG. 6 is an IR absorption spectra of Form V
Figure 18:
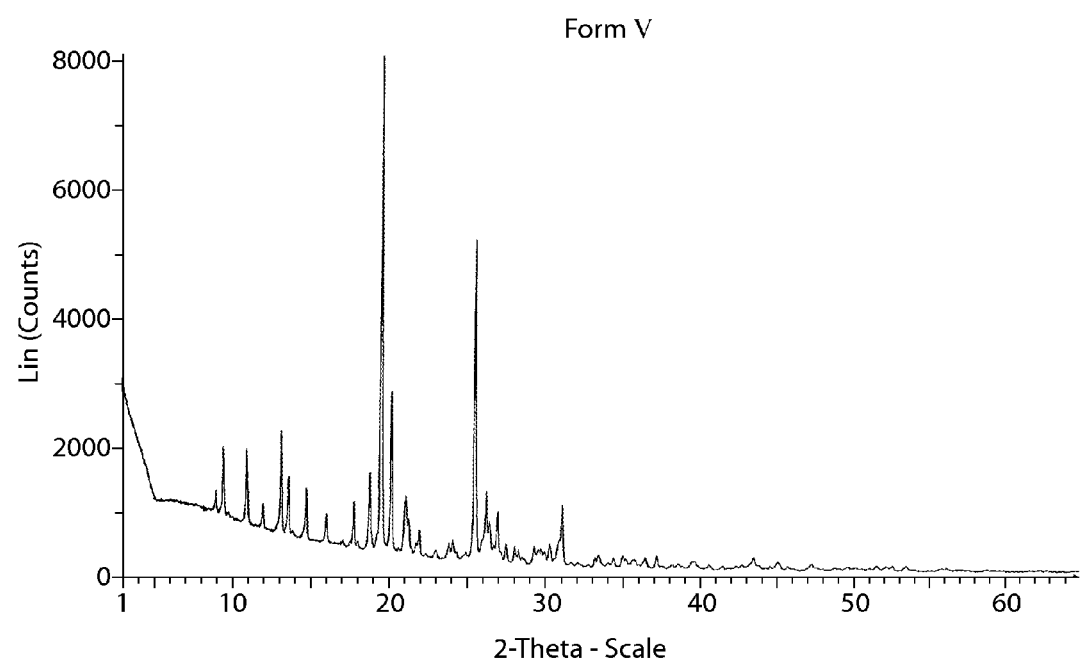
FIG. 18 is an x-ray diffractogram of Form V

Form V according to the invention has the characteristic IR absorption spectra as shown in FIG. 6 and the characteristic X-ray diffraction pattern as shown in FIG. 18. XRD pattern were recorded using a x-ray powder diffractometer (Bruker AXS D5000) in transmission mode (Cu K alpha 1, PSD).

IR absorption spectra were measured in the spectral range 4000-400 cm$^{-1}$ on a Bruker IFS48. Spectral resolution was 2 cm$^{-1}$. Sample preparation was performed generally as KBr disk.

Figure 32:
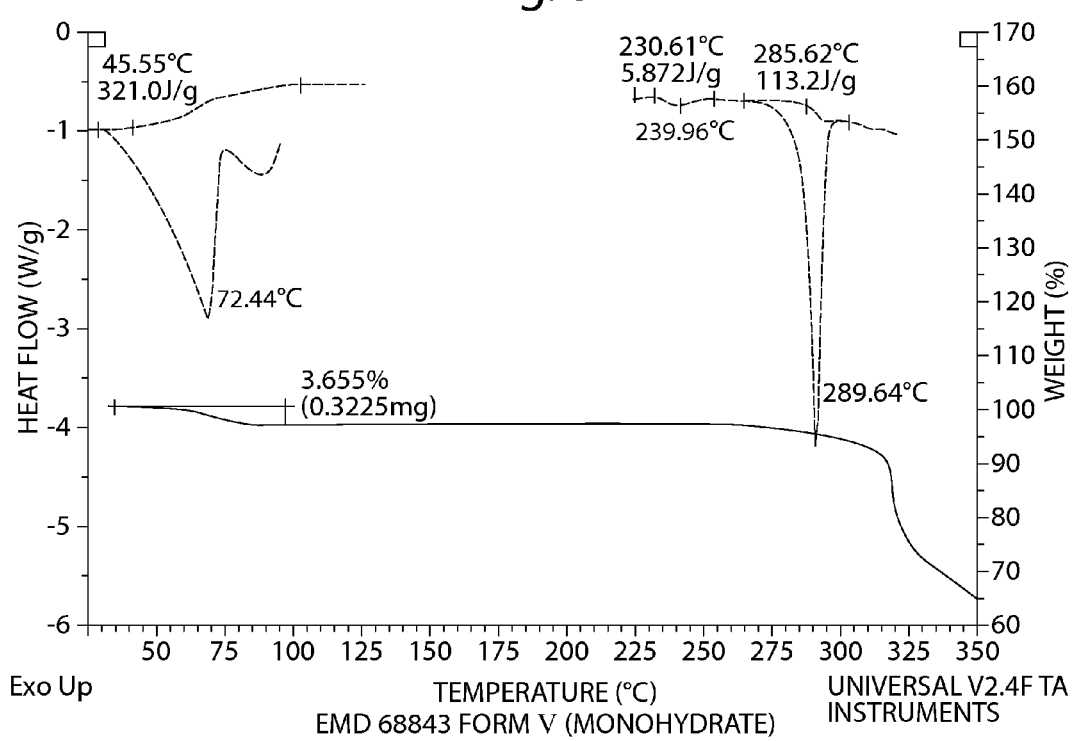
FIG. 32 is a diagram of thermal analysis of Form V

Form V can be further characterized with the aid of a thermal analysis measured in the range of 30° to 350° C. FIG. 32 shows the DSC (TA Instruments DSC 2920) and TGA (TA Instruments TGA 2950) measurements. Form V shows a dehydration process between 25° C. and 100° C. Analysis by thermogravimetry showed the presence of 3 weight-% to 4 weight-% of water (theory of 1:1 solvate 3.63 weight-%). The DSC measurement gives a phase transition to form VII between 200° C. and 260° C. The thermoanalytically resulting form VII melts between 280° C. and 290° C.

Form V of 1-[4-(5-cyanoindol-3-yl)butyl]-4-(2-carbamoyl-benzofuran-5-yl)-piperazine hydrochloride monohydrate according to the invention has surprising advantages with regard to its stability under conditions of high humidity. Form V according to the invention is obtained as colorless solid substance in form of well defined crystals.

The invention also provides a process for preparing the above Form V according to the invention, which comprises:
(1) dispersing 1-[4-(5-cyanoindol-3-yl)butyl]-4-(2-carbamoyl-benzofuran-5-yl)-piperazine in tetrahydrofuran,
(2) converting the 1-[4-(5-cyanoindol-3-yl)butyl]-4-(2-carbamoyl-benzofuran-5-yl)-piperazine base, by addition of aqueous hydrochloric acid into the hydrochloride salt,
(3) precipitation of Form V at room temperature, and
(4) recovering the precipitated 1-[4-(5-cyanoindol-3-yl)butyl]-4-(2-carbamoyl-benzofuran-5-yl)-piperazine hydrochloride monohydrate by filtration, and drying in vacuo at room temperature.

Alternatively, Form V can be prepared according to a process which comprises:
(1) stirring of Form IV of 1-[4-(5-cyanoindol-3-yl)butyl]-4-(2-carbamoyl-benzofuran-5-yl)-piperazine hydrochloride, which will be described later in detail, in water with an amount of 5 to 10 times more relating to Form IV, and
(2) recovering the precipitated 1-[4-(5-cyanoindol-3-yl)butyl]-4-(2-carbamoyl-benzofuran-5-yl)-piperazine hydrochloride monohydrate by filtration, and drying in vacuo at room temperature until the forming of the monohydrate of Form V without excess of water.

Alternatively, Form V can be prepared according to a process which comprises:
(1) stirring of Form XIII of 1-[4-(5-cyanoindol-3-yl)butyl]-4-(2-carbamoyl-benzofuran-5-yl)-piperazine dihydrochloride, which will be described later in detail, in water, and
(2) recovering the precipitated 1-[4-(5-cyanoindol-3-yl)butyl]-4-(2-carbamoyl-benzofuran-5-yl)-piperazine hydrochloride monohydrate by filtration, and drying in vacuo at room temperature.

Figure 7:
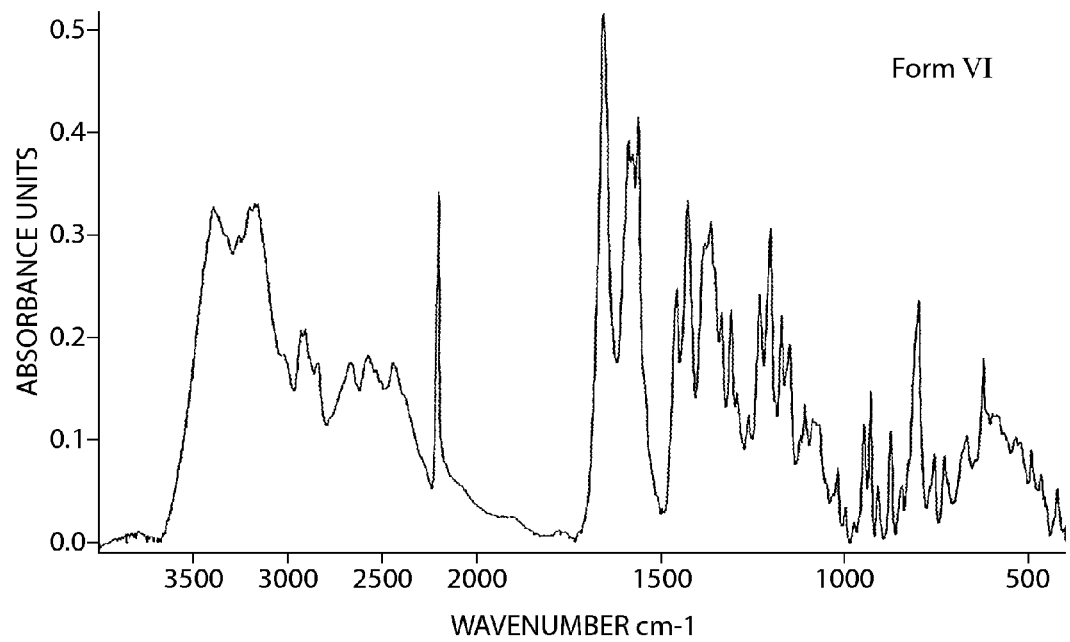
FIG. 7 is an IR absorption spectra of Form VI
Figure 19:
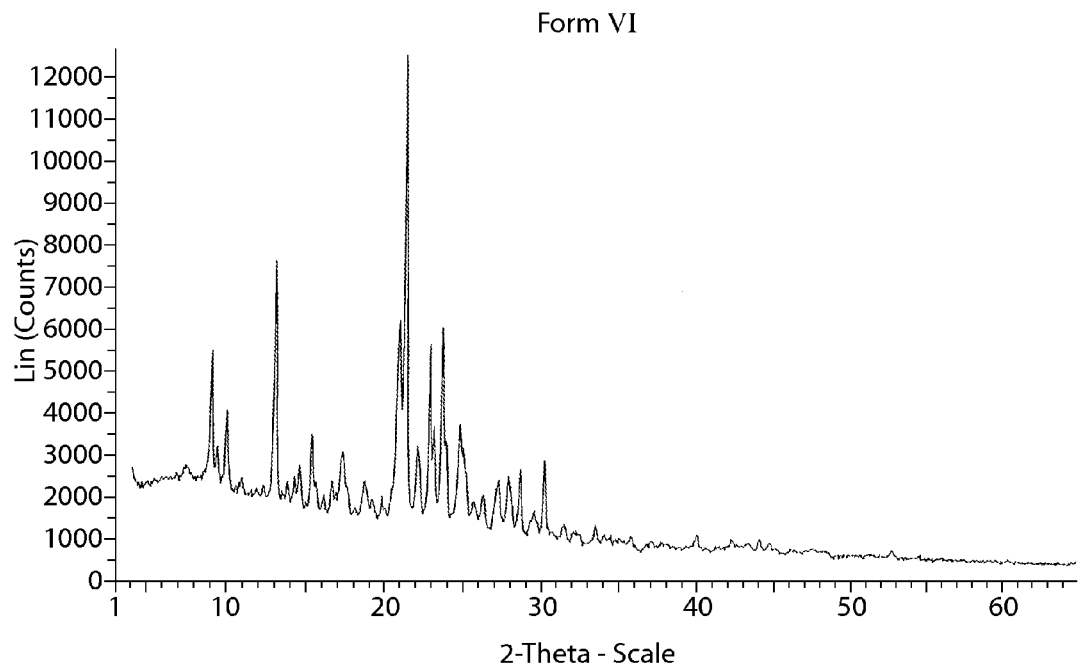
FIG. 19 is an x-ray diffractogram of Form VI

Form VI according to the invention has the characteristic IR absorption spectra as shown in FIG. 7 and the characteristic X-ray diffraction pattern as shown in FIG. 19. XRD pattern were recorded using a x-ray powder diffractometer (Bruker AXS D5000) in transmission mode (Cu K alpha 1, PSD).

IR absorption spectra were measured in the spectral range 4000-400 cm$^{-1}$ on a Bruker IFS48. Spectral resolution was 2 cm$^{-1}$. Sample preparation was performed generally as KBr disk.

Figure 33:
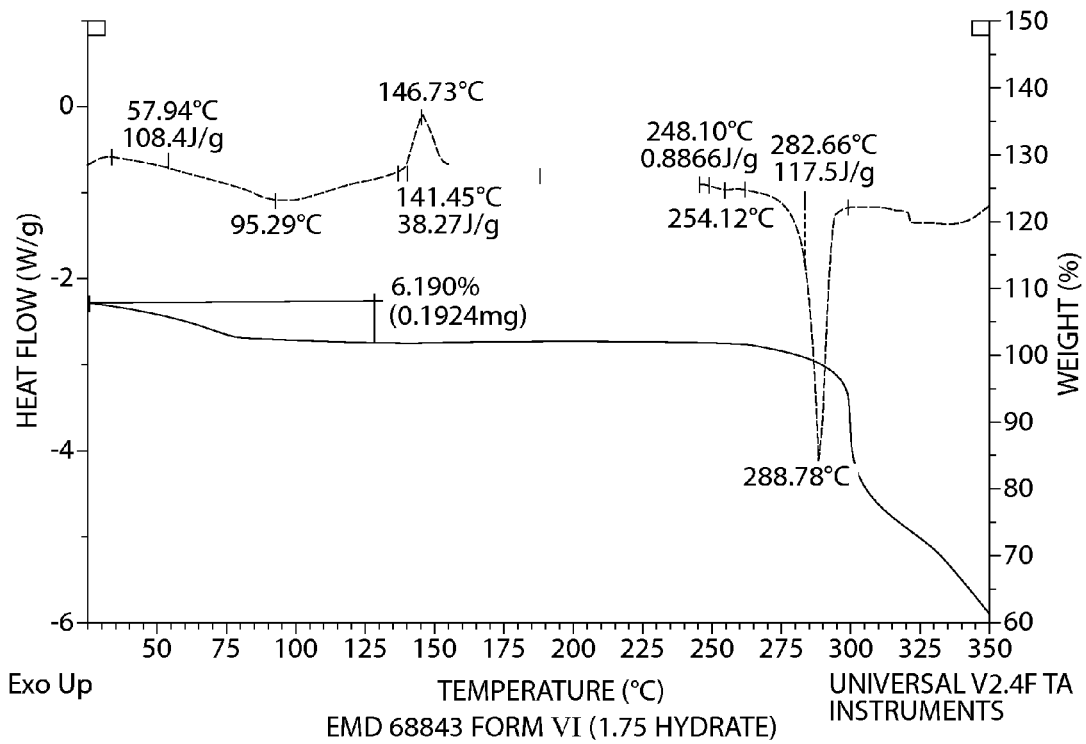
FIG. 33 is a diagram of thermal analysis of Form VI

Form VI can be further characterized with the aid of a thermal analysis measured in the range of 30° to 350° C. FIG. 33 shows the DSC (TA Instruments DSC 2920) and TGA (TA Instruments TGA 2950) measurements. Form VI shows a dehydration process between 25° C. and 100° C. Analysis by thermogravimetry showed the presence of 6 weight-% to 7 weight-% of water (theory of 1:1.75 solvate 6.19 weight-%). The DSC measurement gives a phase transition to form VII between 200° C. and 260° C. The thermoanalytically resulting form VII melts between 280° C. and 290° C.

The invention also provides a process for preparing the above Form VI according to the invention, which comprises:
(1) stirring of Form IV of 1-[4-(5-cyanoindol-3-yl)butyl]-4-(2-carbamoyl-benzofuran-5-yl)-piperazine hydrochloride, which will be described later in detail, in water in which the relative proportions of salt to water are between 1:5 and 1:10, and (2) recovering the precipitated 1-[4-(5-cyanoindol-3-yl)butyl]-4-(2-carbamoyl-benzofuran-5-yl)-piperazine hydrochloride sesquihydrate by filtration, and drying in vacuo at room temperature.

Alternatively, Form VI can be prepared according to a process which comprises:

(1) stirring of Form II of 1-[4-(5-cyanoindol-3-yl)butyl]-4-(2-carbamoyl-benzofuran-5-yl)-piperazine hydrochloride, as described above, in water for one hour, and (2) recovering the precipitated 1-[4-(5-cyanoindol-3-yl)butyl]-4-(2-carbamoyl-benzofuran-5-yl)-piperazine hydrochloride sesquihydrate by filtration, and drying in vacuo at room temperature.

Figure 8:
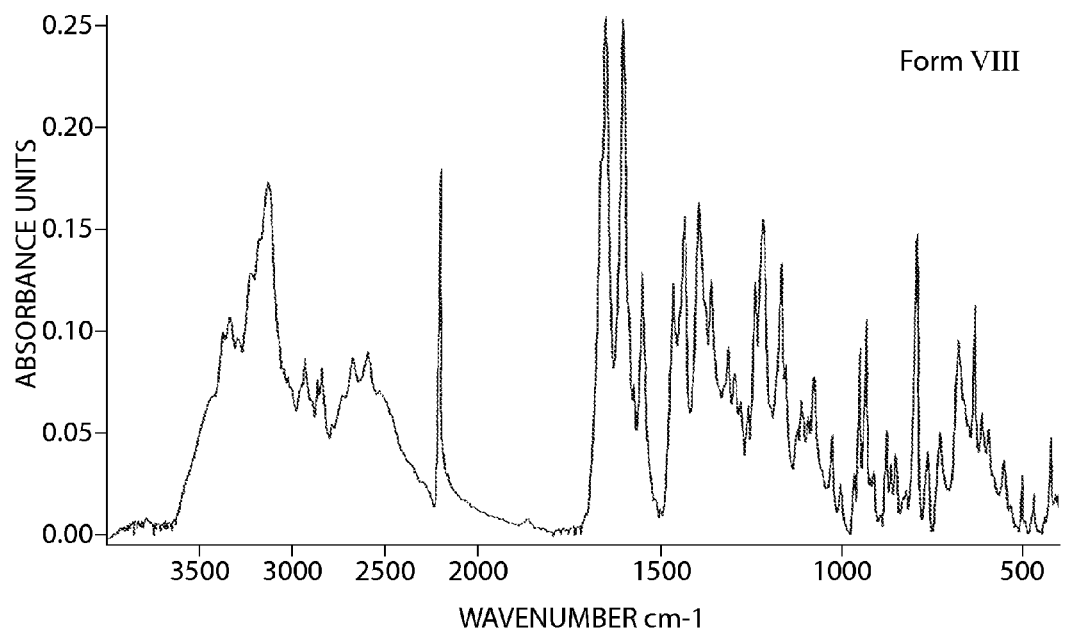
FIG. 8 is an IR absorption spectra of Form VIII
Figure 20:
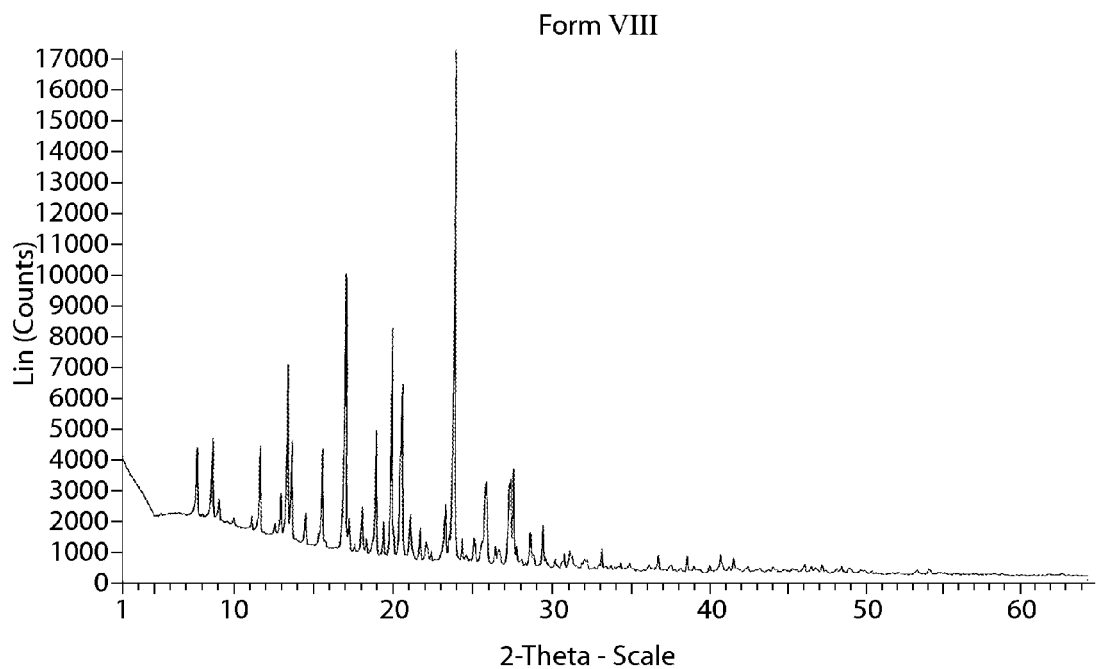
FIG. 20 is an x-ray diffractogram of Form VIII

Form VIII according to the invention has the characteristic IR absorption spectra as shown in FIG. 8 and the characteristic X-ray diffraction pattern as shown in FIG. 20. XRD pattern were recorded using a x-ray powder diffractometer (Bruker AXS D5000) in transmission mode (Cu K alpha 1, PSD).

IR absorption spectra were measured in the spectral range 4000-400 $cm^{-1}$ on a Bruker IFS48. Spectral resolution was 2 $cm^{-1}$. Sample preparation was performed generally as KBr disk.

Figure 35:
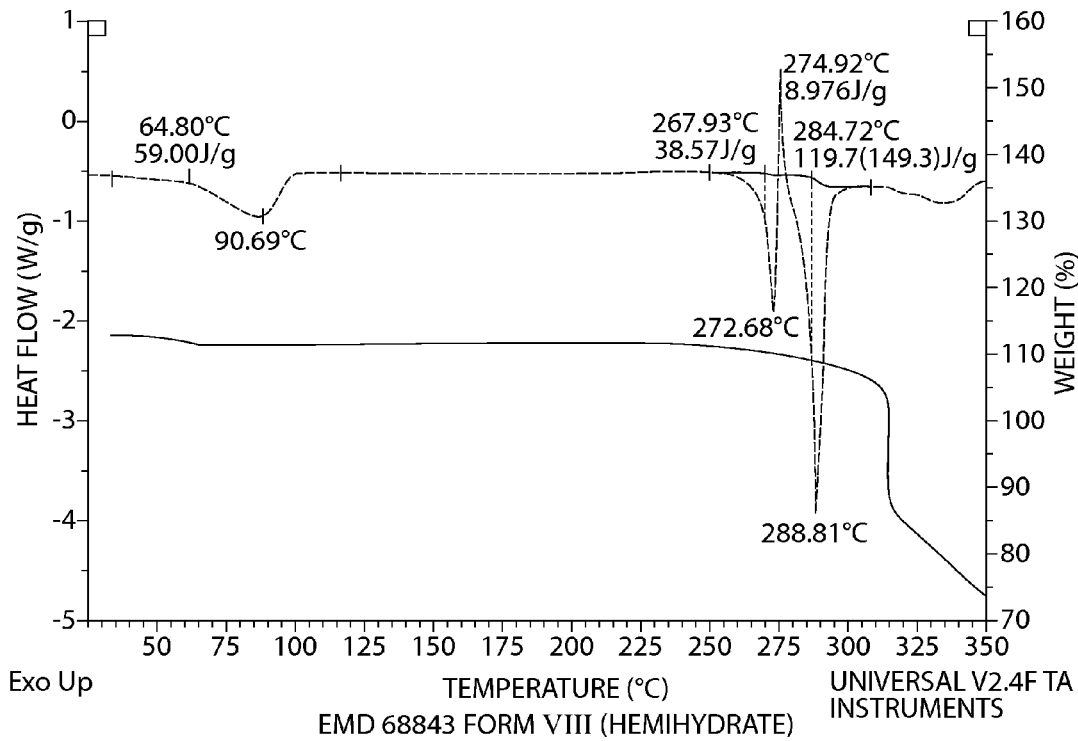
FIG. 35 is a diagram of thermal analysis of Form VIII

Form VIII can be further characterized with the aid of a thermal analysis measured in the range of 30° C. to 350° C. FIG. 35 shows the DSC (TA Instruments DSC 2920) and TGA (TA Instruments TGA 2950) measurements. Form VIII shows a dehydration process between 25° C. and 125° C. Analysis by thermogravimetry showed the presence of 1 weight-% to 2 weight-% of water (theory of 1:0.5 solvate 1.85 weight-%). The DSC measurement gives a melting of resulted form IX around 268° C. The thermoanalytically resulting form VII melts between 280° C. and 290° C.

The invention also provides a process for preparing the above Form VIII according to the invention, which comprises:

(1) stirring of Form VI of 1-[4-(5-cyanoindol-3-yl)butyl]-4-(2-carbamoyl-benzofuran-5-yl)-piperazine hydrochloride, as described above, in water for more than 12 hours, and (2) recovering the precipitated 1-[4-(5-cyanoindol-3-yl)butyl]-4-(2-carbamoyl-benzofuran-5-yl)-piperazine hydrochloride hemihydrate by filtration, and drying in vacuo at room temperature.

Alternatively, Form VIII can be prepared according to a process which comprises:

(1) stirring of Form II of 1-[4-(5-cyanoindol-3-yl)butyl]-4-(2-carbamoyl-benzofuran-5-yl)-piperazine hydrochloride, as described above, in water for 12 hours, and (2) recovering the precipitated 1-[4-(5-cyanoindol-3-yl)butyl]-4-(2-carbamoyl-benzofuran-5-yl)-piperazine hydrochloride hemihydrate by filtration, and drying in vacuo at room temperature.

Additionally, it has been found that 1-[4-(5-cyanoindol-3-yl)butyl]-4-(2-carbamoyl-benzofuran-5-yl)-piperazine hydrochloride form crystalline modifications as anhydrates.

It should be understood that the present anhydrates of the invention may contain unbound water that is to say water which is other than water of crystallization.

Preferred forms of anhydrates of 1-[4-(5-cyanoindol-3-yl)butyl]-4-(2-carbamoyl-benzofuran-5-yl)-piperazine hydrochloride include:

a) 1-[4-(5-cyanoindol-3-yl)butyl]-4-(2-carbamoyl-benzofuran-5-yl)-piperazine hydrochloride in Form IV (as hereinafter defined);

b) 1-[4-(5-cyanoindol-3-yl)butyl]-4-(2-carbamoyl-benzofuran-5-yl)-piperazine hydrochloride in Form III (as hereinafter defined);

c) 1-[4-(5-cyanoindol-3-yl)butyl]-4-(2-carbamoyl-benzofuran-5-yl)-piperazine hydrochloride in Form VII (as hereinafter defined); and d) 1-[4-(5-cyanoindol-3-yl)butyl]-4-(2-carbamoyl-benzofuran-5-yl)-piperazine hydrochloride in Form IX (as hereinafter defined).

Figure 9:
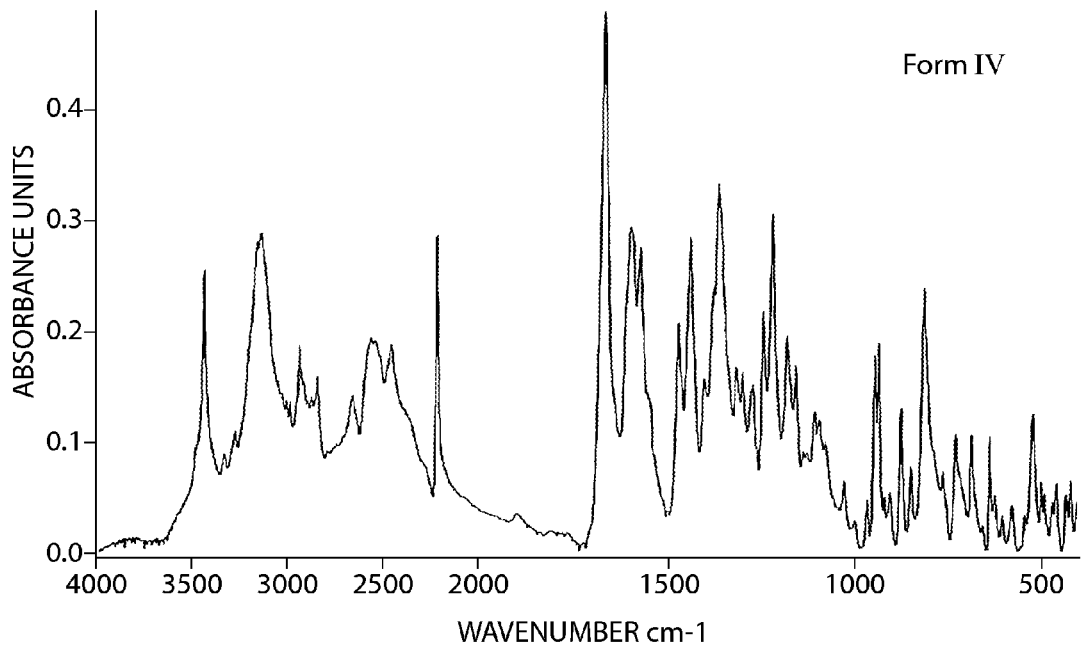
FIG. 9 is an IR absorption spectra of Form IV
Figure 21:
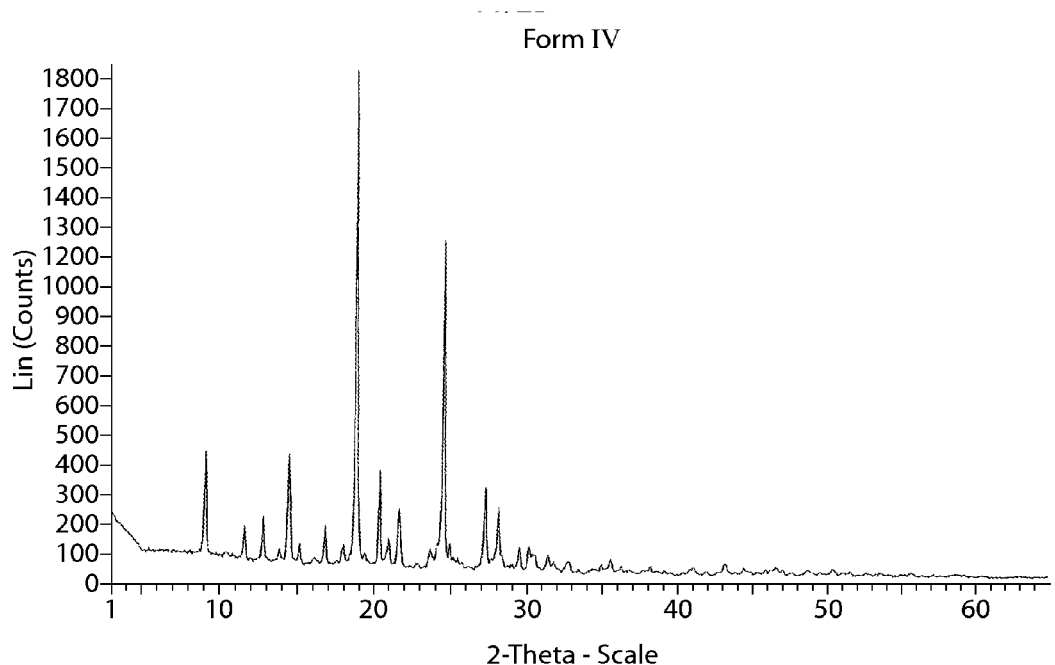
FIG. 21 is an x-ray diffractogram of Form IV

Form IV according to the invention has the characteristic IR absorption spectra as shown in FIG. 9 and the characteristic X-ray diffraction pattern as shown in FIG. 21. XRD pattern were recorded using a x-ray powder diffractometer (Bruker AXS D5000) in transmission mode (Cu K alpha 1, PSD).

IR absorption spectra were measured in the spectral range 4000-400 $cm^{-1}$ on a Bruker IFS48. Spectral resolution was 2 $cm^{-1}$. Sample preparation was performed generally as KBr disk.

Figure 31:
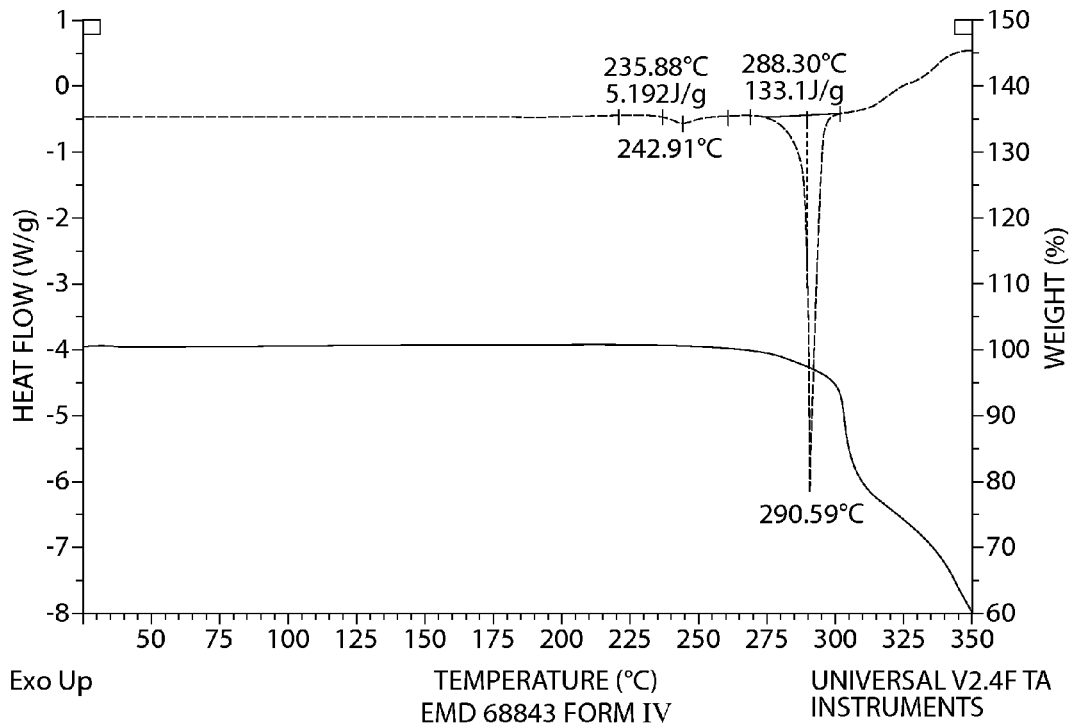
FIG. 31 is a diagram of thermal analysis of Form IV

Form IV can be further characterized with the aid of a thermal analysis measured in the range of 30° to 350° C. FIG. 31 shows the DSC (TA Instruments DSC 2920) and TGA (TA Instruments TGA 2950) measurements. The DSC measurement gives a phase transition to form VII between 200° C. and 260° C. The thermoanalytically resulting form VII melts between 280° C. and 290° C.

Owing to its crystalline properties, Form IV of 1-[4-(5-cyanoindol-3-yl)butyl]-4-(2-carbamoyl-benzofuran-5-yl)-piperazine hydrochloride according to the invention has surprising advantages with regard to its solubility and for its pharmaceutical processing into solid dosage forms. The solubility of Form IV in water is 0.328 µg/ml. Form IV according to the invention is obtained as colorless solid substance in form of well defined crystals.

Figure 27:
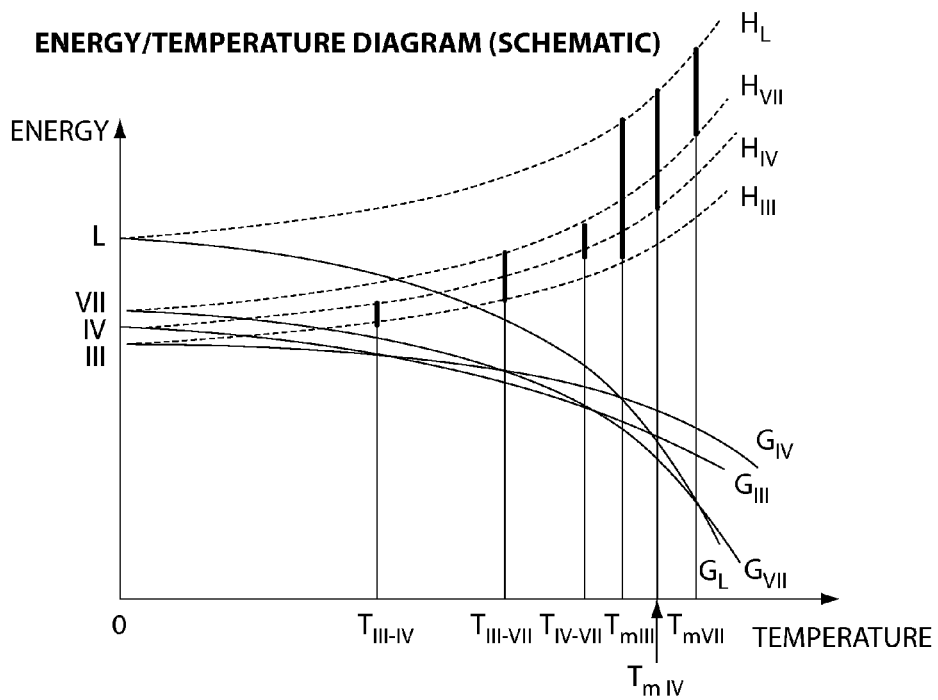
FIG. 27 is an energy/temperature diagram of Forms III, IV and VII

As shown in FIG. 27, Form IV is the most stable form at higher temperatures, e.g. >100° C.

The invention also provides a process for preparing the above Form IV according to the invention, which comprises:

(1) dispersing 1-[4-(5-cyanoindol-3-yl)butyl]-4-(2-carbamoyl-benzofuran-5-yl)-piperazine in tetrahydrofuran, (2) converting the 1-[4-(5-cyanoindol-3-yl)butyl]-4-(2-carbamoyl-benzofuran-5-yl)-piperazine base, by addition of aqueous hydrochloric acid into the hydrochloride salt at temperatures between 20° and 30° C., (3) precipitation of Form V at room temperature, (4) recovering the precipitated 1-[4-(5-cyanoindol-3-yl)butyl]-4-(2-carbamoyl-benzofuran-5-yl)-piperazine hydrochloride monohydrate Form V by filtration, and (5) drying of Form V in vacuo at temperatures of 85° to 90° C. to give Form IV.

Alternatively, Form IV can be prepared according to a process which comprises:

(1) drying of Form XI of 1-[4-(5-cyanoindol-3-yl)butyl]-4-(2-carbamoyl-benzofuran-5-yl)-piperazine hydrochloride monomethanolate, as described above, at temperatures between 55° and 65° C. to give Form IV.

This particular polymorphic form (herein designated "Form IV") has superior properties over other crystalline forms and is more suitable for inclusion in pharmaceutical formulations.

Figure 10:
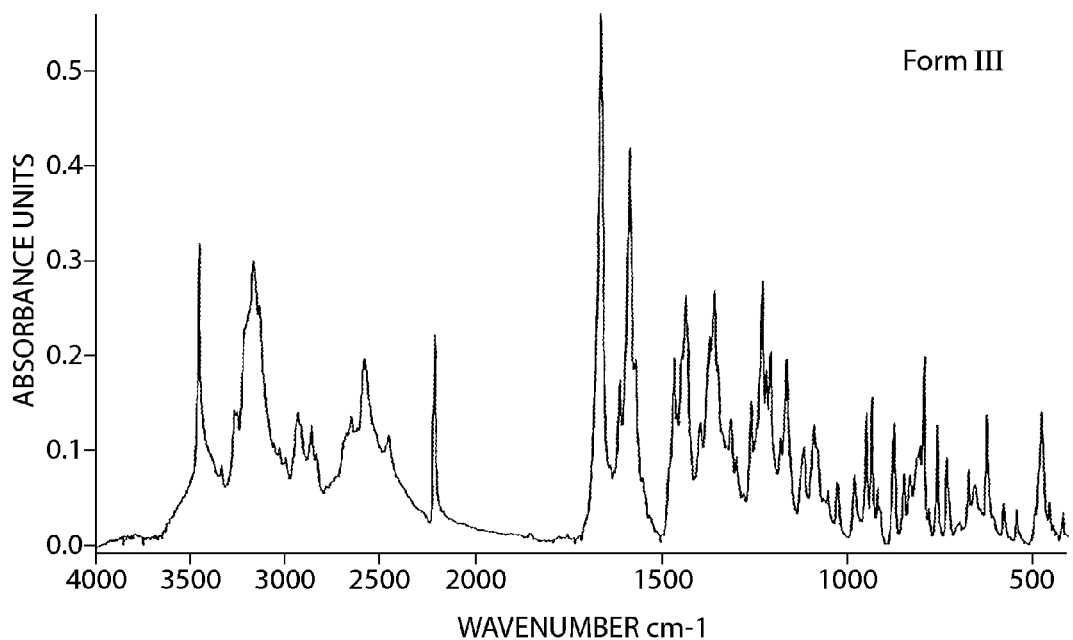
FIG. 10 is an IR absorption spectra of Form III
Figure 22:
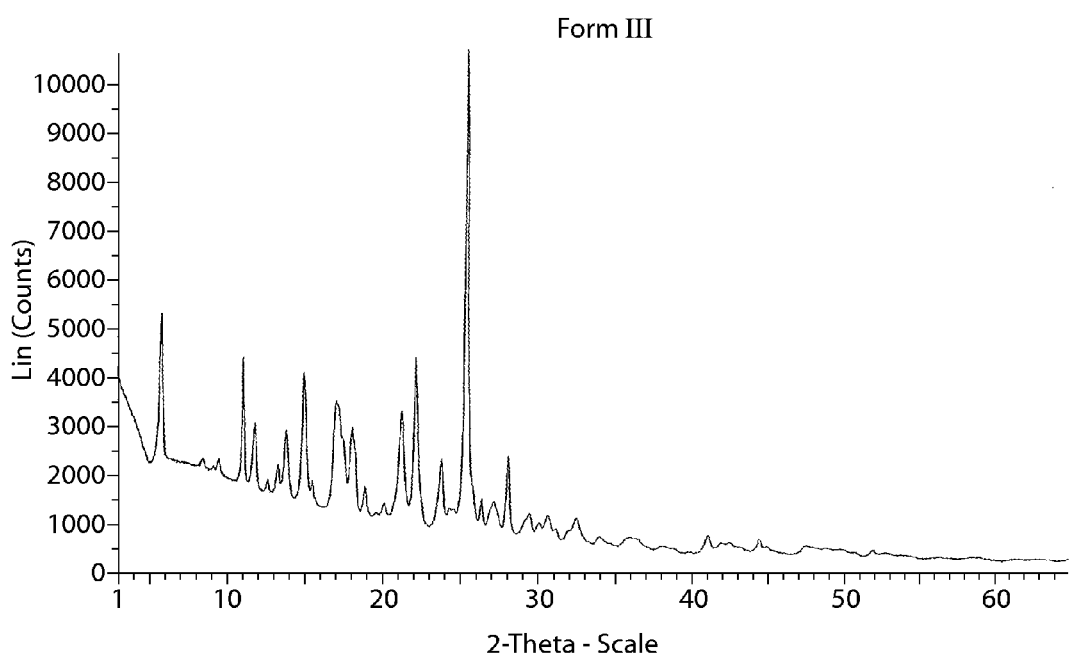
FIG. 22 is an x-ray diffractogram of Form III

Form III according to the invention has the characteristic IR absorption spectra as shown in FIG. 10 and the characteristic X-ray diffraction pattern as shown in FIG. 22. XRD pattern were recorded using a x-ray powder diffractometer (Bruker AXS D5000) in transmission mode (Cu K alpha 1, PSD).

IR absorption spectra were measured in the spectral range 4000-400 cm$^{-1}$ on a Bruker IFS48. Spectral resolution was 2 cm$^{-1}$. Sample preparation was performed generally as KBr disk.

Figure 30:
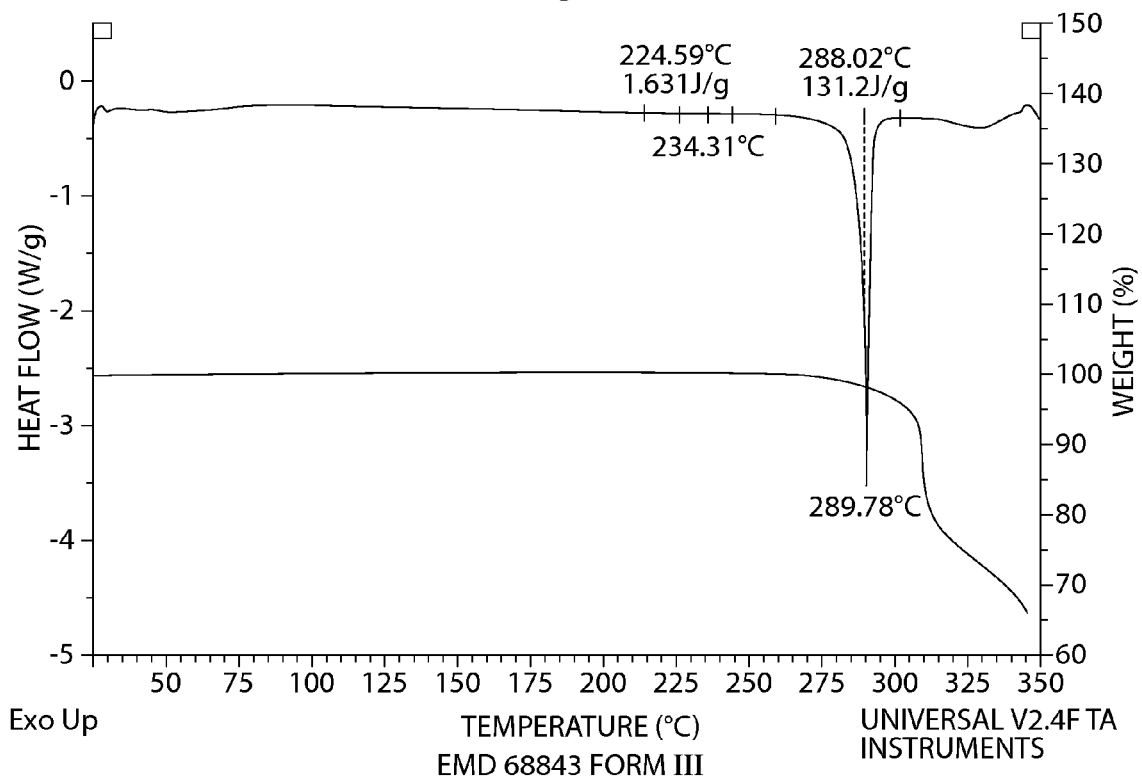
FIG. 30 is a diagram of thermal analysis of Form III

Form III can be further characterized with the aid of a thermal analysis measured in the range of 30° to 350° C. FIG. 30 shows the DSC (TA Instruments DSC 2920) and TGA (TA Instruments TGA 2950) measurements. The DSC measurement gives a phase transition to form VII between 200° C. and 260° C. The thermoanalytically resulting form VII melts between 280° C. and 290°.

Owing to its crystalline properties, Form III of 1-[4-(5-cyanoindol-3-yl)butyl]-4-(2-carbamoyl-benzofuran-5-yl)-piperazine hydrochloride according to the invention is the most stable form at room temperature, that means the thermodynamically stable form at room temperature (FIG. 27). Form III according to the invention is obtained as colorless solid substance in form of well defined crystals.

The invention also provides a process for preparing the above Form III according to the invention, which comprises:
(1) dispersing 1-[4-(5-cyanoindol-3-yl)butyl]-4-(2-carbamoyl-benzofuran-5-yl)-piperazine in tetrahydrofuran,
(2) converting the 1-[4-(5-cyanoindol-3-yl)butyl]-4-(2-carbamoyl-benzofuran-5-yl)-piperazine base, by addition of 1N hydrochloric acid into the hydrochloride salt at temperatures between 10° C. and 40° C., preferably between 20° C. and 30° C.,
(3) precipitation of Form II at room temperature,
(4) recovering the precipitated 1-[4-(5-cyanoindol-3-yl)butyl]-4-(2-carbamoyl-benzofuran-5-yl)-piperazine hydrochloride solvate with tetrahydrofuran by filtration, and
(5) drying of Form II in vacuo at temperatures of at least 100° C. to give Form III.

Figure 11:
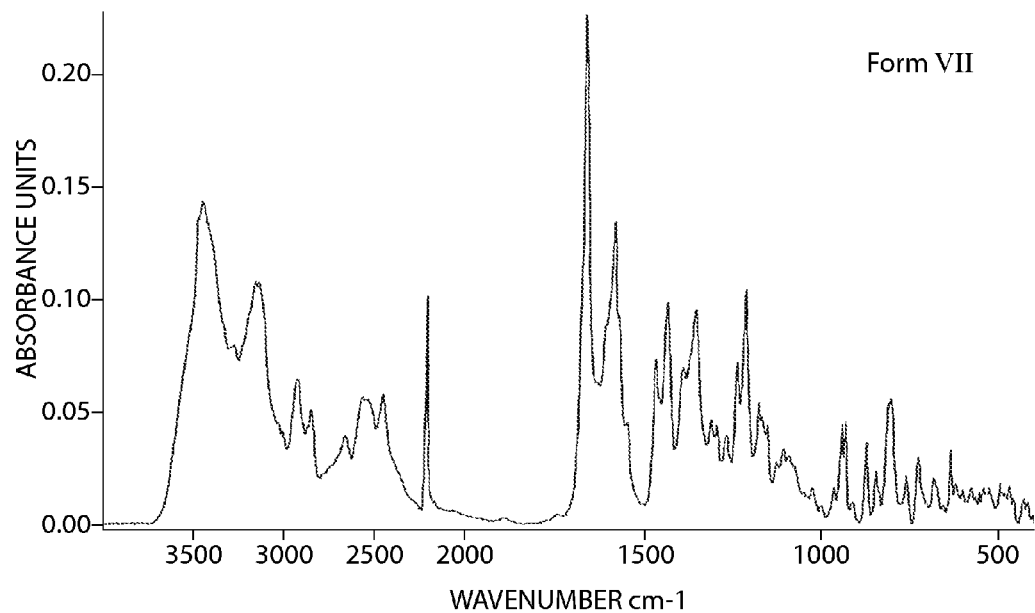
FIG. 11 is an IR absorption spectra of Form VII
Figure 23:
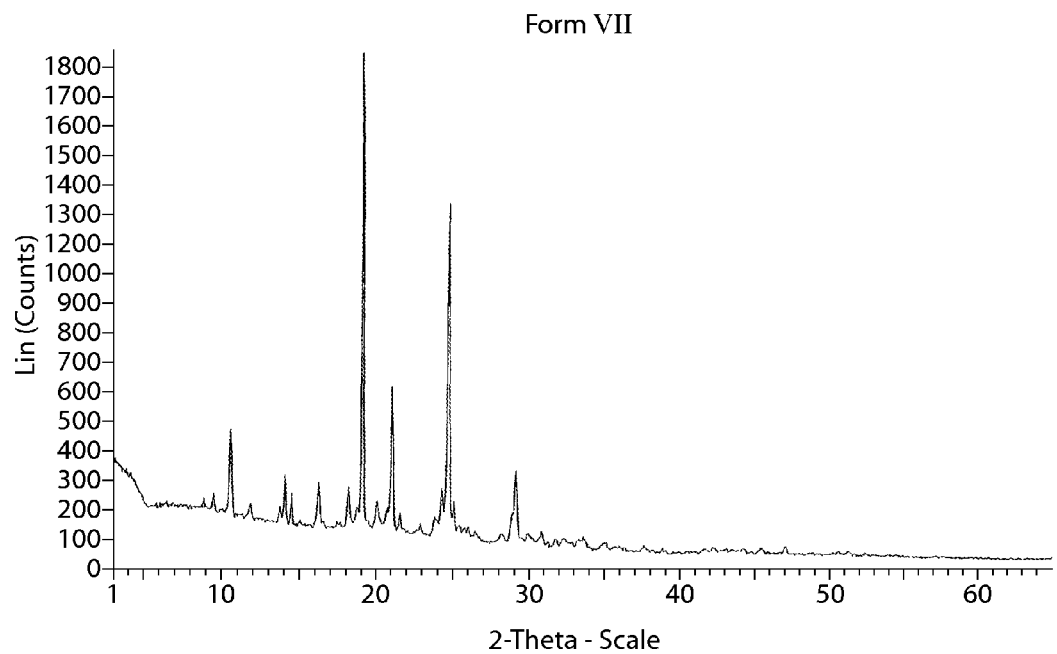
FIG. 23 is an x-ray diffractogram of Form VII

Form VII according to the invention has the characteristic IR absorption spectra as shown in FIG. 11 and the characteristic X-ray diffraction pattern as shown in FIG. 23. XRD pattern were recorded using a x-ray powder diffractometer (Bruker AXS D5000) in transmission mode (Cu K alpha 1, PSD).

IR absorption spectra were measured in the spectral range 4000-400 cm$^{-1}$ on a Bruker IFS48. Spectral resolution was 2 cm$^{-1}$. Sample preparation was performed generally as KBr disk.

Figure 34:
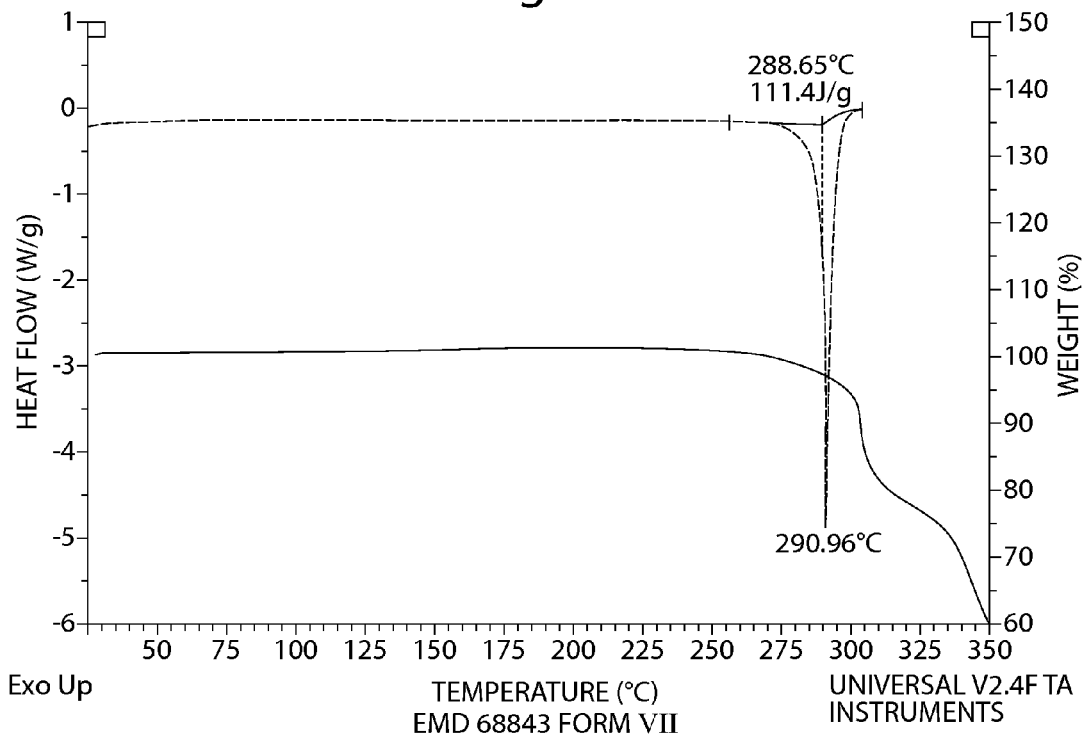
FIG. 34 is a diagram of thermal analysis of Form VII

Form VII can be further characterized with the aid of a thermal analysis measured in the range of 30° to 350° C. FIG. 34 shows the DSC (TA Instruments DSC 2920) and TGA (TA Instruments TGA 2950) measurements. The DSC measurement indicates the melting point of the pure Form VII at 288° C.

Form VII is the high temperature form of 1-[4-(5-cyanoindol-3-yl)butyl]-4-(2-carbamoyl-benzofuran-5-yl)-piperazine hydrochloride according to the invention. Form VII according to the invention is obtained as colorless solid substance in form of well defined crystals.

The invention also provides a process for preparing the above Form VII according to the invention, which comprises:
(1) tempering Form IV of 1-[4-(5-cyanoindol-3-yl)butyl]-4-(2-carbamoyl-benzofuran-5-yl)-piperazine hydrochloride, as described above, at temperatures of at least 200° C., preferably at 250° C., for 30 minutes.

Figure 24:
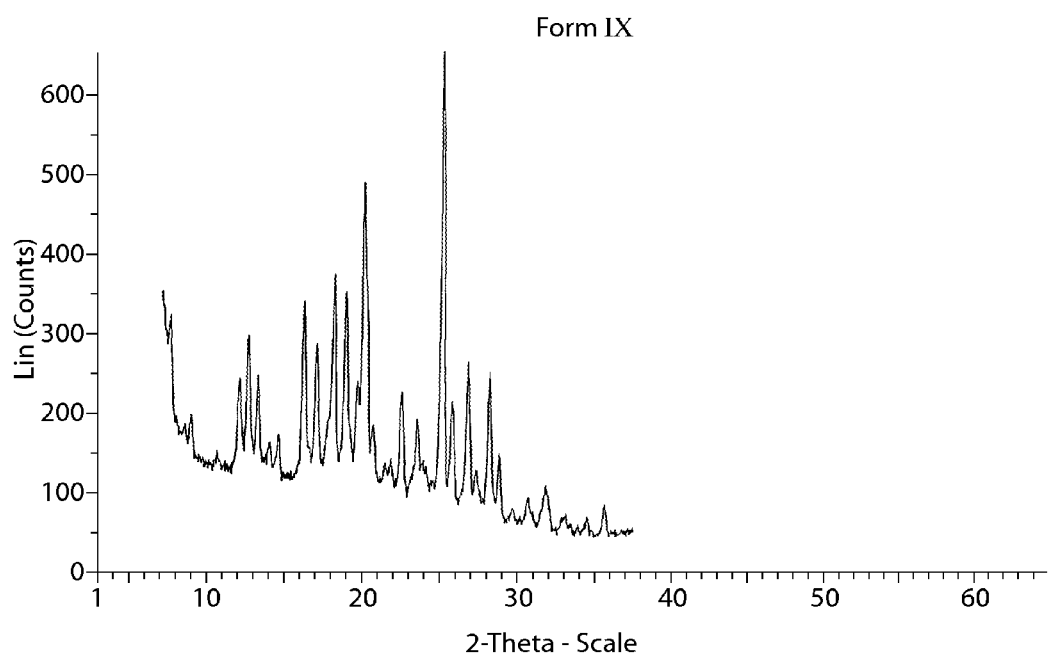
FIG. 24 is an x-ray diffractogram of Form IX

Form IX according to the invention has the characteristic X-ray diffraction pattern as shown in FIG. 24. XRD pattern were recorded using a x-ray powder diffractometer (Bruker AXS D5000) in transmission mode (Cu K alpha 1, PSD).

Figure 36:
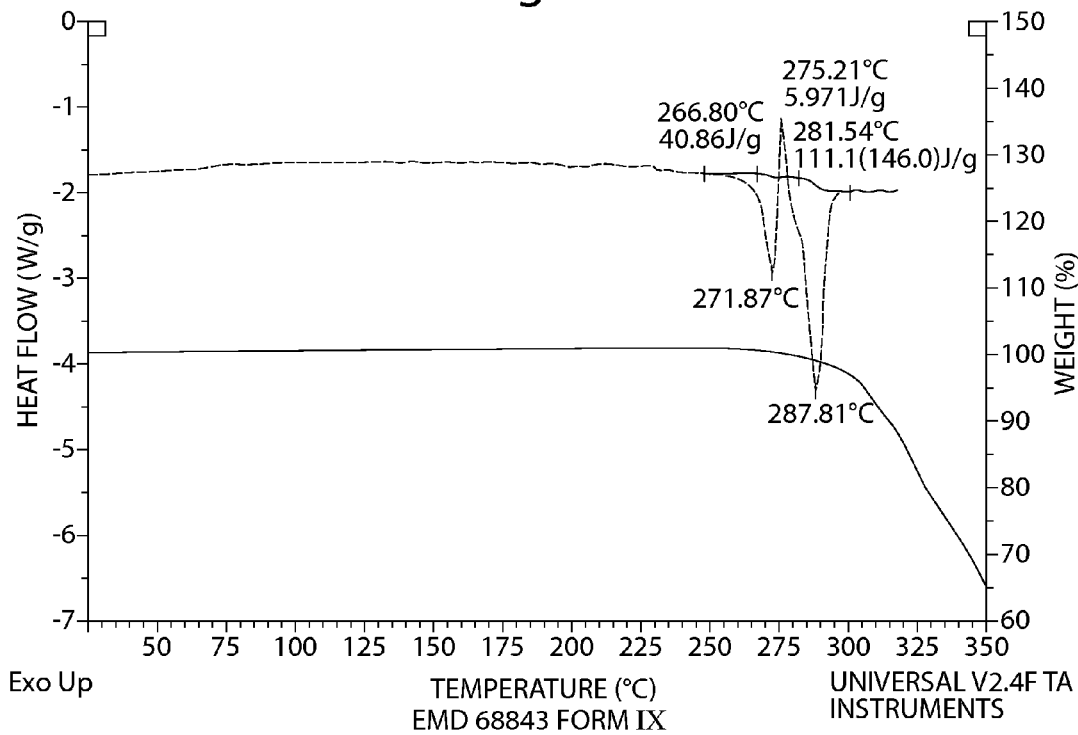
FIG. 36 is a diagram of thermal analysis of Form IX

Form IX can be further characterized with the aid of a thermal analysis measured in the range of 30° to 350° C. FIG. 36 shows the DSC (TA Instruments DSC 2920) and TGA (TA Instruments TGA 2950) measurements. The DSC measurement gives of the melting of form IX at 267° C. followed by a recrystallization to form VII. The thermoanalytically resulting form VII melts between 280° C. and 290° C.

Form IX according to the invention is obtained as colorless solid substance in form of well defined crystals.

The invention also provides a process for preparing the above Form IX according to the invention, which comprises:
(1) drying of Form VIII of 1-[4-(5-cyanoindol-3-yl)butyl]-4-(2-carbamoyl-benzofuran-5-yl)-piperazine hydrochloride, as described above, at temperatures between 90° C. and 110° C. to give Form IX.

Additionally, it has been found that 1-[4-(5-cyanoindol-3-yl)butyl]-4-(2-carbamoyl-benzofuran-5-yl)-piperazine dihydrochloride form crystalline modifications.

It should be understood that the present dihydrochlorides of the invention may contain unbound water that is to say water which is other than water of crystallization.

A preferred form of 1-[4-(5-cyanoindol-3-yl)butyl]-4-(2-carbamoyl-benzofuran-5-yl)-piperazine dihydrochloride is 1-[4-(5-cyanoindol-3-yl)butyl]-4-(2-carbamoyl-benzofuran-5-yl)-piperazine dihydrochloride in Form XIII; (as hereinafter defined).

Figure 25:
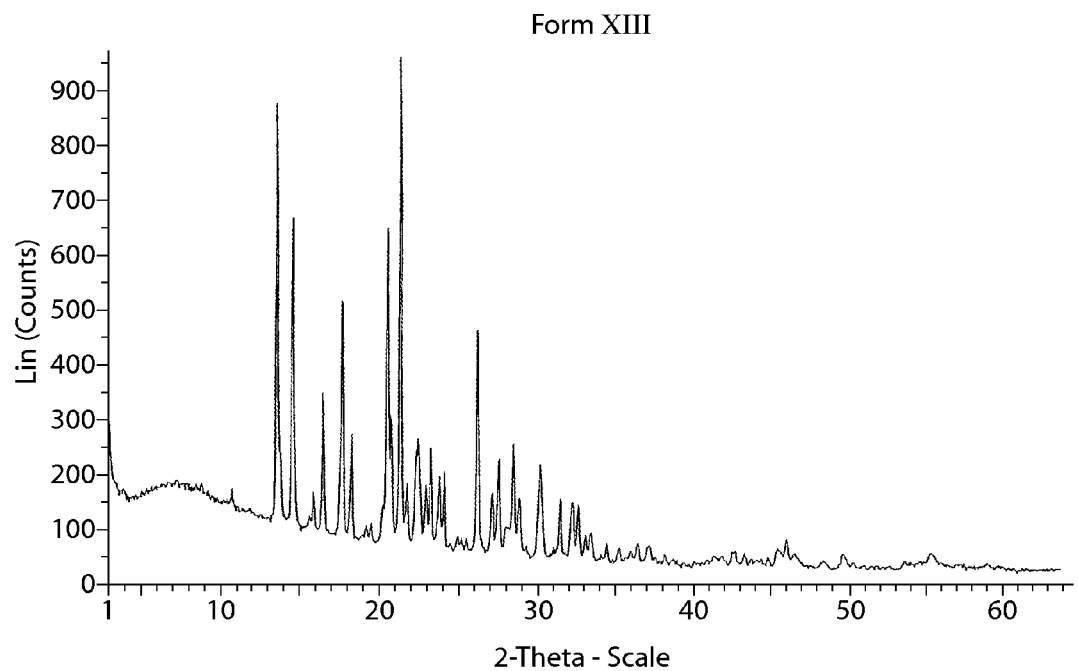
FIG. 25 is an x-ray diffractogram of Form XIII

Form XIII (dihydrochloride) according to the invention has the characteristic X-ray diffraction pattern as shown in FIG. 25. XRD pattern were recorded using a x-ray powder diffractometer (Bruker AXS D5000) in transmission mode (Cu K alpha 1, PSD).

Form XIII according to the invention is obtained as colorless solid substance in form of well defined crystals.

The invention also provides a process for preparing the above Form XIII according to the invention, which comprises:
(1) dispersing 1-[4-(5-cyanoindol-3-yl)butyl]-4-(2-carbamoyl-benzofuran-5-yl)-piperazine in an organic solvent chosen from the group consisting of tetrahydrofuran, ethanol, isopropanol or mixtures thereof with water,
(2) converting the 1-[4-(5-cyanoindol-3-yl)butyl]-4-(2-carbamoyl-benzofuran-5-yl)-piperazine base, by addition of 2N or concentrated hydrochloric acid into the hydrochloride salt at temperatures between 20° and 30° C.,
(3) precipitation of Form XIII at room temperature,
(4) recovering the precipitated 1-[4-(5-cyanoindol-3-yl)butyl]-4-(2-carbamoyl-benzofuran-5-yl)-piperazine dihydrochloride Form XIII by filtration, and
(5) drying of Form XIII in vacuo at room temperature.

Preferably, the solvates of the present invention are in a form having a dense crystalline structure which enables the raw active ingredient to be easily formulated into final dosage form.

Additionally, Form XVI of 1-[4-(5-cyanoindol-3-yl)butyl]-4-(2-carbamoyl-benzofuran-5-yl)-piperazine hydrochloride has been found.

Figure 26:
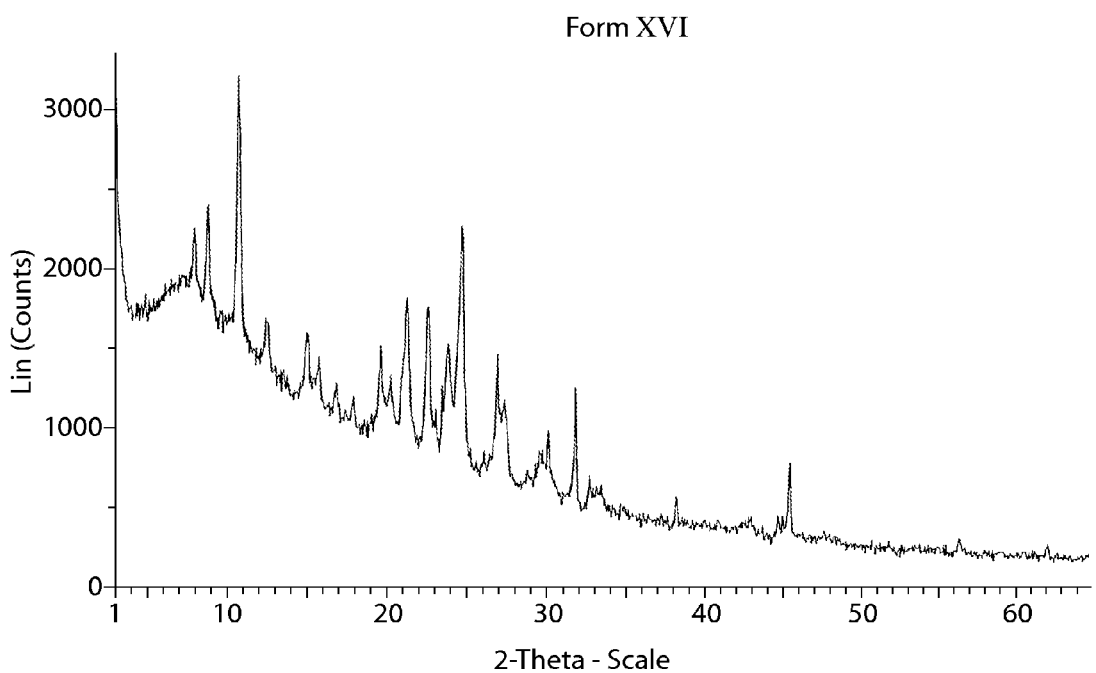
FIG. 26 is an x-ray diffractogram of Form XVI

Form XVI according to the invention has the characteristic X-ray diffraction pattern as shown in FIG. 26. XRD pattern were recorded using a x-ray powder diffractometer (Bruker AXS D5000) in transmission mode (Cu K alpha 1, PSD).

The invention also provides a process for preparing the above Form XVI according to the invention, which comprises:

(1) dissolving 1-[4-(5-cyanoindol-3-yl)butyl]-4-(2-carbamoyl-benzofuran-5-yl)-piperazine hydrochloride in acetonitrile and water in the molar ratio 1:1, and
(2) freeze-drying or spray-drying overnight to give Form XVI of 1-[4-(5-cyanoindol-3-yl)butyl]-4-(2-carbamoyl-benzofuran-5-yl)-piperazine hydrochloride.

Similarly, the freeze-dry process can be performed in other mixtures of water miscible organic solvent (tetrahydrofuran, alcohols, N-methylpyrrolidon) with water.

Additionally, a pure amorphous Form of 1-[4-(5-cyanoindol-3-yl)butyl]-4-(2-carbamoyl-benzofuran-5-yl)-piperazine hydrochloride has been found.

It has been found that due to the solubility and bioavailability properties, Form II and Form VIII are useful as an ingredient of extended release formulations. Form II is especially useful as an ingredient of extended release formulations.

These Forms of 1-[4-(5-cyanoindol-3-yl)butyl]-4-(2-carbamoyl-benzofuran-5-yl)-piperazine hydrochloride or dihydrochloride, as referred to as Forms I, II, III, IV, V, VI, VII, VIII, IX, X, XI, XIII, XIV, XV and XVI respectively and all of which are hereinafter referred to as the "products of the invention" can be used to treat and prevent the disorders: depressive disorders, including the sub-type disorders major depressive disorder and dysthymic disorder, adolescent depression, anxiety disorders, including the sub-type anxiety disorders chosen from the sub-types panic disorder with and/or without agoraphobia, agoraphobia, obsessive-compulsive spectrum disorders, social phobia, specific phobia including neophobia, posttraumatic stress disorder, acute stress indication or generalized-anxiety disorder, bipolar disorders, mania, dementia, including Alzheimer's disease and multi-infarct, substance-related disorders, sexual dysfunctions including premature ejaculation, eating disorders including anorexia nervosa and bulimia nervosa and/or obesity, fibromyalgia, chronic pain, sleeping disorders including dyssomnias and narcolepsy, psychiatric disorders like psychoses, schizophrenia or schizoaffective disorder, cerebral infarct like stroke and cerebral ischemia, CNS disorders such as tension. They are also useful for the therapy of side-effects in the treatment of hypertension (e.g. with α-methyldopa) and for the prophylaxis and therapy of cerebral disorders, in endocrinology and gynecology, e.g. for the treatment of acromegaly, hypogonadism, secondary amenorrhea, premenstrual syndrome or undesired puerperal lactation.

These disorders are herein after referred to as "the Disorders."

The present invention further provides pharmaceutical compositions or medicaments comprising a Product of the Invention. The pharmaceutical composition may comprise additionally one or more conventional auxiliary substances and/or carriers.

Thus, the Products of the Invention can be formulated into the conventional forms of administration, including peroral and parenteral forms of administration. Tablets or capsules are preferred formulations. They can be produced by conventional mixing processes and with the use of conventional auxiliary substances and carriers, as well as binders, disintegrants, flavorings and the like. The dose corresponds to that mentioned in U.S. Pat. No. 5,532,241.

Additionally, the invention relates to the use of a pharmaceutical composition containing at least one product of the invention for the treatment of the Disorders.

The following compositions are preferred:

A Composition comprising Form IV and Form V,

A Composition comprising Form IV and Form V in a molar ratio of about 100 to 1 to 10 to 1, A Pharmaceutical preparation comprising an active ingredient consisting essentially of a mixture of Form IV and Form V, and A Pharmaceutical preparation comprising an active ingredient consisting essentially of a mixture of Form IV and Form V in a molar ratio of about 100 to 1 to 10 to 1.

An extended release formulation comprising Form I and/or Form III and/or form VIII is also preferred.

Furthermore, the present invention relates to the use of Products of the Invention for the manufacture of a medicament for the treatment of and prevention of the Disorders, such as depressive disorders, adolescent depression, anxiety disorders, bipolar disorders, mania, dementia, substance-related disorders, sexual dysfunctions, eating disorders, obesity, fibromyalgia, chronic pain, sleeping disorders, psychiatric disorders, cerebral infarct, tension, for the therapy of side-effects in the treatment of hypertension, cerebral disorders, chronic pain, acromegaly, hypogonadism, secondary amenorrhea, premenstrual syndrome and undesired puerperal lactation.

The present invention further provides a method for treating and/or preventing any one or more of the Disorders by administering an effective and/or prophylactic amount of the Products of the Invention to a patient in need thereof.

Preferably, the Disorders which are treated are depression, anxiety disorders, more preferably social anxiety disorder, panic disorder generalized anxiety disorder, posttraumatic stress disorder and/or obsessive compulsive disorder.

Accordingly, the present invention is further concerned with pharmaceutical formulations comprising this polymorphic form as an active ingredient, and the use of this polymorphic form and its formulations in the treatment of certain disorders.

For the treatment of certain conditions it may be desirable to employ the specific crystalline forms of the present invention in conjunction with another pharmacologically active agent. It will be appreciated that the compound of the present invention may be presented together with another therapeutic agent as a combined preparation for simultaneous, separate or sequential use for the relief of emesis. Such combined preparations may be, for example, in the form of a twin pack.

Without further elaboration, it is believed that one skilled in the art can, using the preceding description, utilize the present invention to its fullest extent. The preferred specific embodiments and examples are, therefore, to be construed as merely illustrative, and not limitative to the remainder of the disclosure in any way whatsoever.

The entire disclosures of all applications, patents, and publications cited above and below, are hereby incorporated by reference.

EXAMPLES

Example 1

Production of Form I of 1-[4-(5-cyanoindol-3-yl) butyl]-4-(2-carbamoyl-benzofuran-5-yl)-piperazine hydrochloride Method 1:
1 g of 1-[4-(5-cyanoindol-3-yl)butyl]-4-(2-carbamoyl-benzofuran-5-yl)-piperazine is dissolved in 80 ml of acetone. The temperature of the solution is allowed to come to 50° C. and 0.5 ml of 1N hydrochloric acid is added to the reaction mixture. After stirring for 2 to 3 minutes the reaction mixture is cooled to room temperature and precipitation occurs. Suction filtration of the precipitated crystals is effected. Drying in vacuo at room temperature to constant weight leads to 1-[4-(5-cyanoindol-3-yl)butyl]-4-(2-carbamoyl-benzofuran-5-yl)-piperazine hydrochloride acetonate Form I.

Method 2:
2.25 g of 1-[4-(5-cyanoindol-3-yl)butyl]-4-(2-carbamoyl-benzofuran-5-yl)-piperazine hydrochloride Form III are dispersed in 200 ml of acetone. After stirring for 14 days the precipitated crystals are recovered by filtration, and drying in vacuo at room temperature to constant weight leads to 1-[4-(5-cyanoindol-3-yl)butyl]-4-(2-carbamoyl-benzofuran-5-yl)-piperazine hydrochloride acetonate Form I which present the IR absorption spectra of FIG. 1 and the x-ray diffraction spectrum of FIG. 12.

Example 2

Production of Form II of 1-[4-(5-cyanoindol-3-yl) butyl]-4-(2-carbamoyl-benzofuran-5-yl)-piperazine hydrochloride Method 1:
1 g of 1-[4-(5-cyanoindol-3-yl)butyl]-4-(2-carbamoyl-benzofuran-5-yl)-piperazine is dissolved in 46.6 g tetrahydrofuran and 2.2 g 1N hydrochloric acid is added to the reaction mixture. After precipitation and stirring for 30 minutes suction filtration of the precipitated crystals is effected. Drying in vacuo at room temperature to constant weight leads to the monosolvate of 1-[4-(5-cyanoindol-3-yl)butyl]-4-(2-carbamoyl-benzofuran-5-yl)-piperazine hydrochloride with tetrahydrofuran of Form II which present the IR absorption spectra of FIG. 2 and the x-ray diffraction spectrum of FIG. 13.

Method 2:
3 g of 1-[4-(5-cyanoindol-3-yl)butyl]-4-(2-carbamoyl-benzofuran-5-yl)-piperazine hydrochloride Form III are dispersed in 400 ml of tetrahydrofuran. After stirring for 20 days the precipitated crystals are recovered by filtration. Drying in vacuo at room temperature to constant weight leads to the solvate of 1-[4-(5-cyanoindol-3-yl)butyl]-4-(2-carbamoyl-benzofuran-5-yl)-piperazine hydrochloride with tetrahydrofuran of Form II.

Example 3

Production of Form XV of 1-[4-(5-cyanoindol-3-yl) butyl]-4-(2-carbamoyl-benzofuran-5-yl)-piperazine hydrochloride 10 ml of 1N hydrochlorid acid are added to a solution of 1-[4-(5-cyanoindol-3-yl)butyl]-4-(2-carbamoyl-benzofuran-5-yl)-piperazine hydrochloride in tetrahydrofuran[200 ml] (molar ratio base to tetrahydrofuran=1:48) at 0° C. After stirring for 30 min the precipitated crystals are recovered by filtration. Drying in vacuo at room temperature to constant weight leads to the solvate of 1-[4-(5-cyanoindol-3-yl)butyl]-4-(2-carbamoyl-benzofuran-5-yl)-piperazine hydrochloride with tetrahydrofuran of Form XV which present the IR absorption spectra of FIG. 3 and the x-ray diffraction spectrum of FIG. 14.

Example 4

Production of Form X of 1-[4-(5-cyanoindol-3-yl) butyl]-4-(2-carbamoyl-benzofuran-5-yl)-piperazine hydrochloride 8.6 g of 1-[4-(5-cyanoindol-3-yl)butyl]-4-(2-carbamoyl-benzofuran-5-yl)-piperazine is dissolved in tetrahydrofuran and 19.4 ml 1N hydrochloric acid and 7.4 ml water are added within 30 minutes to this solution at 35-37° C. After stirring of five hours, precipitation occurs and suction filtration is effected. Drying in vacuo at room temperature to constant weight leads to the solvate of 1-[4-(5-cyanoindol-3-yl)butyl]-4-(2-carbamoyl-benzofuran-5-yl)-piperazine hydrochloride with tetrahydrofuran of Form X which present the x-ray diffraction spectrum of FIG. 15.

Example 5

Production of Form XI of 1-[4-(5-cyanoindol-3-yl) butyl]-4-(2-carbamoyl-benzofuran-5-yl)-piperazine hydrochloride 3 g of 1-[4-(5-cyanoindol-3-yl)butyl]-4-(2-carbamoyl-benzofuran-5-yl)-piperazine hydrochloride Form IV are dispersed in 500 ml of methanol at 60° C. The reaction mixture is cooled to −30° C. and precipitation occurs. Suction filtration of the precipitated crystals is effected at room temperature. Drying in vacuo to constant weight leads to 1-[4-(5-cyanoindol-3-yl)butyl]-4-(2-carbamoyl-benzofuran-5-yl)-piperazine hydrochloride methanolate of Form XI which present the IR absorption spectra of FIG. 4 and the x-ray diffraction spectrum of FIG. 16.

Example 6

Production of Form XIV of 1-[4-(5-cyanoindol-3-yl)butyl]-4-(2-carbamoyl-benzofuran-5-yl)-piperazine hydrochloride 3.6 g of 1-[4-(5-cyanoindol-3-yl)butyl]-4-(2-carbamoyl-benzofuran-5-yl)-piperazine hydrochloride Form III are dispersed in 75 ml of n-heptane. After stirring for three weeks suction filtration of the precipitated crystals is effected at room temperature. Drying in vacuo to constant weight at room temperature leads to the solvate of 1-[4-(5-cyanoindol-3-yl)butyl]-4-(2-carbamoyl-benzofuran-5-yl)-piperazine hydrochloride with n-heptane of Form XIV which present the IR absorption spectra of FIG. 5 and the x-ray diffraction spectrum of FIG. 17.

Example 7

Production of Form V of 1-[4-(5-cyanoindol-3-yl)butyl]-4-(2-carbamoyl-benzofuran-5-yl)-piperazine hydrochloride Method 1:

To a solution of 1 g of 1-[4-(5-cyanoindol-3-yl)butyl]-4-(2-carbamoyl-benzofuran-5-yl)-piperazine in 32.6 g tetrahydrofuran 2.1 g hydrochloric acid (37 weight-%) are added. After stirring suction filtration of the precipitated crystals is effected. Drying in vacuo to constant weight at room temperature leads to 1-[4-(5-cyanoindol-3-yl)butyl]-4-(2-carbamoyl-benzofuran-5-yl)-piperazine hydrochloride hydrate of Form V which present the IR absorption spectra of FIG. 6 and the x-ray diffraction spectrum of FIG. 18.

Method 2:

2.25 g of 1-[4-(5-cyanoindol-3-yl)butyl]-4-(2-carbamoyl-benzofuran-5-yl)-piperazine hydrochloride Form IV are dispersed in 10 bis 20 g water. After stirring for 24 to 48 hours the crystals are recovered by filtration, and drying in vacuo to constant weight at room temperature leads to 1-[4-(5-cyanoindol-3-yl)butyl]-4-(2-carbamoyl-benzofuran-5-yl)-piperazine hydrochloride hydrate of Form V.

Method 3:

10 g of 1-[4-(5-cyanoindol-3-yl)butyl]-4-(2-carbamoyl-benzofuran-5-yl)-piperazine dihydrochloride Form XIII are dispersed in 1 l water. After stirring for 48 hours the crystals are recovered by filtration, and drying in vacuo to constant weight at room temperature leads to 1-[4-(5-cyanoindol-3-yl)butyl]-4-(2-carbamoyl-benzofuran-5-yl)-piperazine hydrochloride hydrate of Form V.

Example 8

Production of Form VI of 1-[4-(5-cyanoindol-3-yl)butyl]-4-(2-carbamoyl-benzofuran-5-yl)-piperazine hydrochloride Method 2:

10 g of 1-[4-(5-cyanoindol-3-yl)butyl]-4-(2-carbamoyl-benzofuran-5-yl)-piperazine hydrochloride Form II are dispersed in 100 ml water. After stirring for 1 hour the crystals are recovered by filtration, and drying in vacuo to constant weight at room temperature leads to 1-[4-(5-cyanoindol-3-yl)butyl]-4-(2-carbamoyl-benzofuran-5-yl)-piperazine hydrochloride hydrate of Form VI.

Example 9

Production of Form VIII of 1-[4-(5-cyanoindol-3-yl)butyl]-4-(2-carbamoyl-benzofuran-5-yl)-piperazine hydrochloride Method 1:

1 g of 1-[4-(5-cyanoindol-3-yl)butyl]-4-(2-carbamoyl-benzofuran-5-yl)-piperazine hydrochloride Form VI are dispersed in 10 ml water. After stirring for 12 hours the crystals are recovered by filtration, and drying in vacuo to constant weight at room temperature leads to 1-[4-(5-cyanoindol-3-yl)butyl]-4-(2-carbamoyl-benzofuran-5-yl)-piperazine hydrochloride hydrate of Form VIII which present the IR absorption spectra of FIG. 8 and the x-ray diffraction spectrum of FIG. 20.

Method 2:

10 g of 1-[4-(5-cyanoindol-3-yl)butyl]-4-(2-carbamoyl-benzofuran-5-yl)-piperazine hydrochloride Form II are dispersed in 10 to 20 g water. After stirring for more than 1 hour the crystals are recovered by filtration, and drying in vacuo to constant weight at room temperature leads to 1-[4-(5-cyanoindol-3-yl)butyl]-4-(2-carbamoyl-benzofuran-5-yl)-piperazine hydrochloride hydrate of Form VIII. (After stirring for about 1 hour Form VI occurs as an intermediate which is subsequently converted into Form VIII)

Example 10

Production of Form IV of 1-[4-(5-cyanoindol-3-yl)butyl]-4-(2-carbamoyl-benzofuran-5-yl)-piperazine hydrochloride Method 1:

Drying of Form V prepared according to example 7 in vacuo to constant weight at 85° to 90° C. leads to 1-[4-(5-cyanoindol-3-yl)butyl]-4-(2-carbamoyl-benzofuran-5-yl)-piperazine hydrochloride of Form IV which present the IR absorption spectra of FIG. 9 and the x-ray diffraction spectrum of FIG. 21.

Method 2:

Drying of Form XI prepared according to example 5 in vacuo to constant weight at 60° C. leads to 1-[4-(5-cyanoindol-3-yl)butyl]-4-(2-carbamoyl-benzofuran-5-yl)-piperazine hydrochloride of Form IV.

Example 11

Production of Form III of 1-[4-(5-cyanoindol-3-yl)butyl]-4-(2-carbamoyl-benzofuran-5-yl)-piperazine hydrochloride Drying of Form II prepared according to example 2 in vacuo to constant weight at 100° to 110° C. leads to 1-[4-(5-cyanoindol-3-yl)butyl]-4-(2-carbamoyl-benzofuran-5-yl)-piperazine hydrochloride of Form III which present the IR absorption spectra of FIG. 10 and the x-ray diffraction spectrum of FIG. 22.

Example 12

Production of Form VII of 1-[4-(5-cyanoindol-3-yl)butyl]-4-(2-carbamoyl-benzofuran-5-yl)-piperazine hydrochloride Tempering of Form IV prepared according to example 10 for 10 minutes at 250° C. leads to 1-[4-(5-cyanoindol-3-yl)butyl]-4-(2-carbamoyl-benzofuran-5-yl)-piperazine hydrochloride of Form VII which present the IR absorption spectra of FIG. 11 and the x-ray diffraction spectrum of FIG. 23.

Example 13

Production of Form IX of 1-[4-(5-cyanoindol-3-yl)butyl]-4-(2-carbamoyl-benzofuran-5-yl)-piperazine hydrochloride Drying of Form VIII prepared according to example 9 in vacuo to constant weight at 100° to 110° C. leads to 1-[4-(5-cyanoindol-3-yl)butyl]-4-(2-carbamoyl-benzofuran- 5-yl)-piperazine hydrochloride of Form IX which present the x-ray diffraction spectrum of FIG. 24.

Example 14

Production of Form XIII of 1-[4-(5-cyanoindol-3-yl)butyl]-4-(2-carbamoyl-benzofuran-5-yl)-piperazine dihydrochloride 3 g of 1-[4-(5-cyanoindol-3-yl)butyl]-4-(2-carbamoyl-benzofuran-5-yl)-piperazine is dissolved in 100 ml of tetrahydrofuran and 10 ml of 2N or concentrated hydrochloric acid. After stirring for 2 to 3 minutes suction filtration of the precipitated crystals is effected. Drying in vacuo at room temperature to constant weight leads to 1-[4-(5-cyanoindol-3-yl)butyl]-4-(2-carbamoyl-benzofuran-5-yl)-piperazine dihydrochloride of Form XIII which present the characteristic x-ray diffraction spectrum of FIG. 25.

Example 15

Production of Form XVI of 1-[4-(5-cyanoindol-3-yl)butyl]-4-(2-carbamoyl-benzofuran-5-yl)-piperazine hydrochloride Method 1: Freeze-Dry
500 mg of 1-[4-(5-cyanoindol-3-yl)butyl]-4-(2-carbamoyl-benzofuran-5-yl)-piperazine hydrochloride of Form IV, III, VII or IX are dissolved in a mixture of 100 ml acetonitril and 100 ml water. The solution is freeze-dried over night to yield 500 mg of a white powder which present the characteristic x-ray diffraction spectrum of FIG. 26.
Advantage: 1-[4-(5-cyanoindol-3-yl)butyl]-4-(2-carbamoyl-benzofuran-5-yl)-piperazine hydrochloride is better soluble in the solvent mixture than in each solvent alone. Similarly the freeze-dry process can be performed in other mixtures of water miscible organic solvent (tetrahydrofuran, alcohols, N-methylpyrrolidon) with water.
Method 2:
b) Spray-Dry
500 mg 1-[4-(5-cyanoindol-3-yl)butyl]-4-(2-carbamoyl-benzofuran-5-yl)-piperazine hydrochloride of Form IV, III, VII or IX are dissolved in a mixture of 100 ml acetonitril and 100 ml water. The solution is spray-dried to yield Form XVI.

Example 16

Solubility data of Forms II, III, IV, V, VI and VIII are measured according to Alex Avdeef et al., *Pharm. Pharmacol. Commun.*, 1998, 4:165-178 and Alex Avdeef et al., *Pharmaceutical Research*, 2000, 17:85-89 via potentiometric titration.
The pSOL™ solubility profiler, automatically collects potentiometric data, calculates the pH-solubility profiles, and prints the values at 0.1 pH unit intervals. Intrinsic solubilities in the milli-, micro- and nanogram levels can be determined. Also presented are two new concepts, the Flux Factor Profile and Dose Limit Profile. Both concepts follow the guidelines consistent with the BioPharmaceutics Classification Scheme.

TABLE II

Solubility data in µg/ml

| Form I | Form II | Form III | Form IV | Form V | Form VI | Form VIII |
|---|---|---|---|---|---|---|
| 0.08 | 0.03 | 0.12 | 0.33 | 0.18 | 0.23 | 0.10 |

Below are given the most relevant peaks of the IR-spectra of the individual Forms:
Form I
3459 (m), 3335 (w), 3271 (m), 3252 (w), 3202 (m), 3180 (m), 3148 (m), 3039 (w), 3009 (w), 2941 (m), 2868 (m), 2847 (m), 2660 (m), 2579 (m), 2487 (w), 2451 (m), 2212 (m), 1761 (w), 1711 (s), 1673 (s), 1617 (m), 1597 (s), 1577 (m), 1473 (m), 1468 (m), 1444 (m), 1423 (w), 1400 (m), 1364 (s), 1319 (w), 1302 (w), 1279 (w), 1265 (m), 1244 (w), 1225 (s), 1197 (w), 1184 (m), 1171 (m), 1136 (w), 1115 (m), 1100 (m), 1093 (sh), 1034 (w), 1013 (w), 973 (w), 956 (m), 939 (m), 925 (w), 881 (m), 864 (m), 841 (w), 832 (w), 821 (m), 801 (m), 762 (m), 738 (m), 730 (w), 689 (sh), 673 (m), 644 (m), 622 (w), 607 (w), 580 (w), 543 (w), 534 (w), 508 (m), 500 (m), 491 (m), 471 (w), 454 (w).
Form II
3458 (m), 3424 (sh), 3348 (w), 3277 (w), 3204 (m), 3184 (m), 3036 (w), 3008 (w), 2972 (sh), 2938 (m), 2863 (m), 2659 (m), 2597 (m), 2579 (m), 2556 (m), 2459 (m), 2210 (m), 1736 (w), 1677 (s), 1618 (m), 1601 (s), 1578 (m), 1552 (sh), 1474 (m), 1446 (m), 1402 (m), 1376 (m), 1368 (m), 1320 (m), 1302 (w), 1275 (w), 1262 (m), 1250 (m), 1221 (m), 1198 (w), 1186 (m), 1169 (m), 1156 (w), 1131 (w), 1116 (w), 1101 (w), 1065 (m), 1034 (w), 1011 (w), 974 (w), 955 (m), 941 (m), 925 (w), 913 (w), 881 (m), 859 (w), 833 (w), 817 (w), 809 (w), 800 (m), 762 (w), 739 (w), 694 (w), 676 (w), 640 (w), 607 (w), 583 (w), 542 (w), 506 (w), 495 (w), 455 (w).
Form III
3460 (m), 3337 (w), 3269 (m), 3257 (m), 3177 (m), 3145 (m), 3061 (m), 3033 (m), 3001 (w), 2936 (m), 2922 (sh), 2865 (m), 2837 (w), 2787 (m), 2655 (m), 2591 (m), 2457 (m), 2218 (m), 1674 (s), 1618 (m), 1598 (s), 1577 (m), 1473 (m), 1463 (m), 1453 (sh), 1445 (m), 1402 (m), 1380 (m), 1368 (m), 1356 (m), 1329 (m), 1320 (m), 1304 (w), 1284 (w), 1265 (m), 1256 (m), 1240 (m), 1226 (m), 1215 (m), 1186 (m), 1172 (m), 1124 (m), 1097 (m), 1088 (sh), 1059 (w), 1035 (w), 987 (w), 955 (m), 941 (m), 924 (m), 918 (sh), 879 (m), 853 (w), 835 (w), 809 (m), 800 (m), 784 (w), 762 (m), 736 (w), 677 (w), 659 (w), 629 (m), 608 (w), 581 (w), 544 (w), 495 (w), 478 (m), 454 (w).
Form IV
3437 (m), 3328 (w), 3273 (w), 3030 (m), 3006 (m), 2987 (m), 2938 (m), 2915 (m), 2875 (m), 2845 (m), 2660 (m), 2459 (m), 2222 (s), 1899 (w), 1670 (s), 1602 (s), 1577 (s), 1475 (m), 1444 (s), 1370 (s), 1320 (m), 1304 (m), 1281 (m), 1275 (m), 1249 (m), 1227 (s), 1186 (m), 1162 (m), 1141 (w), 1131 (w), 1112 (m), 1099 (m), 1082 (w), 1032 (w), 971 (w), 951 (m), 942 (m), 909 (w), 881 (m), 854 (m), 822 (m), 768 (w), 733 (w), 691 (w), 660 (m), 642 (w), 628 (w), 607 (w), 581 (w), 526 (m), 502 (w), 493 (w), 471 (w), 461 (w).
Form V
3483 (s), 3460 (s), 3222 (s), 3192 (m), 3007 (w), 2947 (m), 2864 (w), 2838 (w), 2784 (w), 2682 (m), 2606 (m), 2478 (w), 2461 (w), 2219 (m), 1669 (s), 1604 (s), 1575 (m), 1474 (m), 1461 (m), 1444 (m), 1402 (m), 1382 (m), 1371 (sh), 1362 (m), 1321 (w), 1304 (m), 1271 (m), 1263 (sh), 1247 (m), 1226 (m), 1185 (m), 1160 (m), 1137 (w), 1113 (m), 1101 (w), 1091 (w), 1082 (w), 1058 (w), 1048 (w), 1030 (w), 1008 (w), 972 (w), 954 (m), 942 (m), 917 (w), 883 (w), 857 (w), 822 (m), 815 (w), 767 (w), 739 (w), 682 (w), 661 (w), 641 (w), 624 (w), 591 (w), 583 (w), 529 (m), 499 (w).
Form VI
3410 (s), 3334 (sh), 3271 (s), 3217 (s), 3188 (s), 3172 (s), 3032 (sh), 2938 (m), 2915 (m), 2846 (m), 2675 (m), 2581 (m), 2539 (sh), 2449 (m), 2216 (s), 1670 (s), 1603 (s), 1593

(s), 1577 (s), 1470 (m), 1444 (s), 1397 (m), 1381 (s), 1369 (sh), 1350 (m), 1323 (m), 1304 (m), 1272 (m), 1247 (m), 1219 (s), 1187 (m), 1164 (m), 1132 (m), 1120 (m), 1099 (m), 1030 (w), 1008 (w), 983 (w), 960 (m), 942 (m), 920 (w), 887 (m), 854 (w), 838 (w), 815 (m), 776 (sh), 767 (w), 739 (w), 727 (sh), 677 (w), 655 (w), 635 (m), 607 (w), 542 (w), 530 (w), 499 (w), 472 (w), 426 (w).

Form VII 3480 (sh), 3459 (s), 3166 (m), 3146 (m), 3031 (m), 3007 (m), 2926 (m), 2870 (sh), 2853 (m), 2664 (m), 2570 (m), 2540 (sh), 2460 (m), 2221 (m), 1673 (s), 1613 (sh), 1592 (s), 1578 (sh), 1552 (m), 1475 (m), 1445 (m), 1398 (m), 1366 (m), 1319 (m), 1303 (m), 1275 (m), 1248 (m), 1226 (m), 1187 (m), 1177 (m), 1161 (m), 1133 (w), 1114 (w), 1101 (w), 1033 (w), 1009 (w), 973 (w), 952 (m), 942 (m), 925 (w), 919 (w), 882 (m), 855 (w), 823 (m), 815 (w), 769 (w), 735 (w), 690 (w), 642 (m), 627 (w), 608 (w), 581 (w), 571 (w), 559 (w), 547 (w), 501 (w).

Form VIII 3379 (m), 3342 (m), 3298 (m), 3234 (m), 3188 (s), 3141 (s), 3027 (w), 2938 (m), 2866 (w), 2844 (m), 2787 (w), 2729 (w), 2679 (m), 2598 (m), 2210 (s), 1658 (s), 1611 (s), 1576 (w), 1556 (m), 1472 (m), 1464 (m), 1443 (s), 1404 (s), 1385 (sh), 1369 (m), 1331 (sh), 1321 (m), 1302 (w), 1286 (w), 1264 (w), 1249 (m), 1230 (s), 1177 (m), 1162 (m), 1128 (w), 1117 (w), 1099 (w), 1084 (w), 1033 (w), 1008 (w), 971 (w), 958 (m), 941 (m), 926 (w), 917 (w), 898 (w), 882 (w), 870 (w), 857 (w), 836 (w), 826 (w), 803 (s), 767 (w), 733 (w), 687 (m), 655 (w), 641 (m), 618 (w), 599 (w), 554 (w), 535 (w), 503 (w), 493 (w), 470 (w), 439 (w).

Form XI 3415 (s), 3290 (m), 3282 (m), 3234 (s), 3196 (s), 3176 (s), 3005 (m), 2993 (m), 2938 (m), 2849 (m), 2678 (m), 2629 (m), 2592 (m), 2473 (m), 2457 (m), 2217 (s), 1680 (s), 1673 (s), 1608 (s), 1594 (sh), 1576 (s), 1474 (m), 1457 (sh), 1440 (s), 1427 (sh), 1401 (m), 1372 (m), 1365 (m), 1354 (m), 1321 (m), 1304 (sh), 1281 (m), 1263 (w), 1247 (m), 1236 (m), 1222 (s), 1185 (m), 1175 (m), 1169 (m), 1160 (sh), 1128 (m), 1121 (m), 1100 (m), 1086 (m), 1032 (w), 1019 (w), 978 (w), 958 (m), 942 (m), 921 (w), 893 (w), 884 (m), 856 (m), 813 (m), 775 (w), 764 (w), 739 (w), 731 (w), 699 (w), 673 (m), 658 (w), 634 (m), 608 (m), 567 (m), 544 (m), 535 (w), 502 (w), 492 (w), 476 (w), 466 (w), 455 (w).

Form XIV 3458 (s), 2923 (m), 2853 (m), 2696 (w), 2595 (w), 2456 (w), 2218 (m), 1674 (s), 1617 (m), 1598 (s), 1580 (sh), 1559 (sh), 1472 (m), 1445 (m), 1401 (m), 1383 (m), 1369 (m), 1321 (m), 1304 (w), 1263 (sh), 1240 (m), 1226 (m), 1216 (m), 1186 (m), 1169 (m), 1159 (m), 1123 (m), 1096 (m), 1057 (w), 1034 (w), 986 (m), 956 (m), 941 (m), 924 (w), 883 (w), 864 (w), 853 (m), 810 (m), 801 (m), 762 (m), 735 (m), 641 (w), 629 (m), 501 (m).

Form XV 3458 (s), 3281 (m), 3227 (m), 3187 (sh), 2935 (m), 2925 (sh), 2866 (w), 2701 (w), 2594 (w), 2455 (w), 2217 (m), 1675 (s), 1617 (m), 1598 (m), 1578 (m), 1472 (m), 1444 (m), 1401 (m), 1380 (m), 1369 (m), 1357 (sh), 1320 (m), 1303 (w), 1265 (m), 1241 (m), 1227 (m), 1215 (m), 1203 (w), 1186 (w), 1172 (m), 1123 (w), 1097 (w), 1087 (w), 1032 (w), 986 (w), 956 (w), 941 (w), 924 (w), 882 (w), 853 (w), 835 (w), 812 (w), 802 (w), 762 (w), 736 (w), 676 (w), 641 (w), 630 (w).

Below are given the most relevant peaks of the Raman-spectra of the individual Forms with an estimated accuracy of +/−5 cm$^{-1}$:

Form I:

3128 (m), 3071 (m), 3044 (w), 3011 (w), 2993 (m), 2975 (m), 2956 (m), 2912 (m), 2868 (m), 2849 (m), 2214 (s), 1674 (m), 1618 (m), 1594 (s), 1578 (s), 1553 (m), 1475 (w), 1446 (m), 1400 (m), 1367 (m), 1347 (m), 1337 (m), 1322 (m), 1303 (m), 1282 (m), 1267 (m), 1244 (s), 1229 (m), 1184 (m), 1174 (m), 1138 (m), 1097 (m), 1052 (m), 1033 (m), 1014 (m), 974 (w), 957 (w), 940 (m), 925 (w), 914 (w), 881 (m), 836 (w), 818 (m), 794 (w), 783 (w), 767 (w), 753 (w), 729 (w), 693 (w), 674 (w), 658 (w), 644 (w), 625 (w), 608 (w), 587 (w), 581 (w), 540 (w), 503 (w), 492 (w), 477 (w), 443 (w), 438 (w), 407 (w), 380 (w), 328 (w), 298 (w), 268 (w), 252 (w), 230 (w), 211 (w).

Form II:

3128 (w), 3113 (w), 3068 (m), 3040 (w), 3031 (w), 2992 (m), 2974 (m), 2957 (m), 2905 (m), 2865 (m), 2850 (m), 2222 (m), 2210 (s), 1679 (m), 1617 (m), 1603 (s), 1579 (s), 1552 (m), 1476 (w), 1447 (m), 1404 (w), 1369 (m), 1358 (m), 1347 (m), 1323 (m), 1304 (m), 1277 (m), 1266 (m), 1245 (m), 1233 (w), 1220 (w), 1186 (m), 1176 (m), 1134 (w), 1102 (w), 1051 (m), 1033 (m), 1010 (w), 974 (w), 957 (w), 942 (m), 927 (w), 917 (w), 882 (m), 862 (w), 846 (w), 830 (m), 819 (m), 786 (w), 767 (w), 755 (w), 735 (w), 695 (w), 679 (w), 661 (w), 641 (w), 632 (w), 608 (w), 586 (w), 541 (w), 506 (w), 495 (w), 477 (w), 447 (w), 438 (w), 405 (w), 379 (w), 330 (w), 298 (w), 270 (w), 255 (w), 228 (w), 212 (m).

Form III:

3128 (w), 3087 (sh), 3061 (m), 2995 (m), 2984 (m), 2966 (m), 2957 (m), 2939 (m), 2916 (m), 2867 (m), 2790 (w), 2220 (s), 1675 (m), 1619 (s), 1595 (s), 1579 (s), 1554 (m), 1476 (w), 1446 (m), 1404 (w), 1376 (w), 1352 (m), 1328 (m), 1303 (m), 1285 (m), 1272 (m), 1266 (m), 1247 (s), 1228 (w), 1215 (w), 1170 (w), 1137 (w), 1098 (m), 1058 (w), 1034 (w), 989 (w), 957 (m), 942 (m), 924 (m), 884 (m), 858 (w), 839 (m), 826 (m), 783 (w), 752 (w), 731 (w), 702 (w), 678 (w), 659 (w), 628 (w), 609 (w), 581 (w), 563 (w), 546 (w), 496 (w), 482 (w), 469 (w), 444 (w), 409 (m), 367 (w), 352 (w), 328 (w), 285 (w), 264 (w), 249 (w), 212 (m).

Form IV:

3160 (w), 3145 (w), 3109 (w), 3073 (m), 3008 (w), 2987 (m), 2973 (m), 2959 (w), 2936 (w), 2910 (m), 2870 (w), 2849 (m), 2797 (w), 2226 (s), 1665 (w), 1622 (m), 1588 (s), 1549 (m), 1478 (w), 1445 (w), 1410 (w), 1355 (w), 1346 (m), 1322 (m), 1277 (w), 1252 (m), 1189 (m), 1144 (w), 1116 (w), 1049 (w), 1034 (w), 1005 (w), 973 (w), 943 (m), 927 (w), 916 (w), 883 (m), 831 (m), 817 (w), 770 (w), 757 (w), 736 (w), 695 (w), 685 (w), 661 (w), 642 (w), 628 (w), 610 (w), 587 (w), 536 (w), 504 (w), 493 (w), 475 (w), 460 (w), 439 (w), 409 (w), 390 (w), 344 (w), 317 (w), 277 (w), 248 (w), 223 (w).

Form V:

3112 (w), 3091 (m), 3074 (m), 3028 (w), 3004 (w), 2081 (m), 2933 (w), 2919 (m), 2866 (w), 2841 (w), 2787 (w), 2222 (s), 1663 (w), 1618 (m), 1607 (m), 1577 (s), 1552 (m), 1478 (m), 1440 (m), 1406 (w), 1381 (m), 1358 (m), 1342 (m), 1321 (m), 1307 (m), 1276 (m), 1252 (m), 1235 (m), 1189 (m), 1143 (w), 1105 (w), 1092 (w), 1052 (w), 1012 (w), 974 (w), 944 (m), 927 (w), 918 (w), 885 (m), 860 (w), 847 (w), 830 (m), 771 (m), 757 (w), 736 (w), 696 (w), 684 (w), 660 (w), 642 (w), 626 (w), 610 (w), 583 (w), 541 (m), 501 (w), 478 (w), 441 (w), 410 (w), 381 (w), 323 (w), 302 (w), 282 (w), 239 (w), 226 (w).

Form XI:

3133 (m), 3094 (w), 3078 (m), 3060 (m), 3004 (w), 2989 (m), 2968 (m), 2943 (m), 2923 (w), 2897 (m), 2871 (w), 2852 (w), 2835 (w), 2221 (s), 1676 (m), 1613 (s), 1578 (s), 1544 (m), 1473 (m), 1447 (m), 1424 (m), 1401 (w), 1375 (m), 1353 (m), 1342 (m), 1325 (m), 1302 (m), 1279 (m), 1264 (m), 1246 (m), 1233 (m), 1222 (w), 1197 (w), 1186 (w), 1171 (m), 1130 (w), 1102 (w), 1078 (m), 1049 (w), 1018 (w), 983 (w), 959 (w), 942 (m), 923 (m), 886 (m), 857 (w), 838 (m), 817 (m), 765 (w), 749 (w), 733 (w), 698 (w), 673 (w), 658 (w), 634 (w), 627 (w), 609 (w), 566 (w), 546 (w), 535 (w), 503 (w), 492 (w), 481 (w), 467 (w), 440 (w), 432 (w), 406 (m), 366 (w), 354 (w), 327 (w), 285 (w), 241 (w).

Form XIV:

3128 (w), 3061 (m), 3002 (m), 2995 (m), 2983 (w), 2966 (m), 2957 (m), 2938 (m), 2914 (m), 2867 (m), 2219 (s), 1675 (m), 1619 (s), 1596 (s), 1579 (s), 1554 (m), 1475 (w), 1446 (m), 1404 (w), 1374 (w), 1352 (m), 1329 (w), 1322 (w), 1303 (m), 1285 (m), 1273 (m), 1265 (m), 1247 (m), 1228 (w), 1216 (w), 1204 (w), 1187 (w), 1170 (m), 1137 (w), 1098 (m), 1058 (w), 1034 (w), 989 (w), 958 (w), 942 (m), 924 (m), 884 (m), 858 (w), 840 (m), 825 (w), 782 (w), 752 (w), 732 (w), 701 (w), 678 (w), 657 (w), 629 (w), 609 (w), 581 (w), 563 (w), 546 (w), 536 (w), 496 (w), 482 (w), 469 (w), 443 (w), 409 (m), 397 (w), 367 (w), 328 (w), 319 (w), 286 (w), 265 (w), 248 (w), 212 (w).

TABLE III

Data of powder-XRD-pattern of polymorphic Forms.
(10 characteristic peaks of each polymorph have been taken for evaluation. The XRD instrument is controlled for 2Theta ± 0.1°).

| No. | d (Å) | 2θ | I/I$_0$ |
|---|---|---|---|
| | Form I: | | |
| 1 | 8.501 | 10.40 | 21 |
| 2 | 7.898 | 11.19 | 17 |
| 3 | 6.606 | 13.39 | 31 |
| 4 | 6.532 | 13.54 | 25 |
| 5 | 6.416 | 13.79 | 26 |
| 6 | 5.590 | 15.84 | 28 |
| 7 | 4.210 | 21.09 | 63 |
| 8 | 3.761 | 23.64 | 18 |
| 9 | 3.632 | 24.49 | 100 |
| 10 | 3.452 | 25.79 | 26 |
| | Form II: | | |
| 1 | 8.426 | 10.49 | 29 |
| 2 | 7.541 | 11.73 | 25 |
| 3 | 6.742 | 13.12 | 41 |
| 4 | 6.119 | 14.46 | 33 |
| 5 | 5.455 | 16.24 | 39 |
| 6 | 4.592 | 19.32 | 30 |
| 7 | 4.425 | 20.05 | 26 |
| 8 | 4.083 | 21.75 | 54 |
| 9 | 3.782 | 23.50 | 100 |
| 10 | 3.380 | 26.35 | 37 |
| | Form III: | | |
| 1 | 15.165 | 5.82 | 32 |
| 2 | 8.034 | 11.00 | 27 |
| 3 | 5.944 | 14.89 | 27 |
| 4 | 5.224 | 16.96 | 23 |
| 5 | 5.089 | 17.41 | 15 |
| 6 | 4.932 | 17.97 | 18 |
| 7 | 4.195 | 21.16 | 23 |
| 8 | 4.029 | 22.05 | 35 |
| 9 | 3.520 | 25.28 | 100 |
| 10 | 3.181 | 28.03 | 16 |
| | Form IV: | | |
| 1 | 9.732 | 9.08 | 22 |
| 2 | 6.885 | 12.85 | 10 |
| 3 | 6.102 | 14.50 | 22 |
| 4 | 5.246 | 16.89 | 9 |
| 5 | 4.695 | 18.89 | 100 |
| 6 | 4.344 | 20.43 | 20 |
| 7 | 4.088 | 21.72 | 12 |
| 8 | 3.615 | 24.61 | 67 |
| 9 | 3.258 | 27.35 | 17 |
| 10 | 3.164 | 28.18 | 12 |
| | Form V: | | |
| 1 | 9.466 | 9.34 | 14 |
| 2 | 8.166 | 10.83 | 15 |
| 3 | 6.807 | 13.00 | 20 |
| 4 | 6.569 | 13.47 | 12 |
| 5 | 4.742 | 18.70 | 16 |
| 6 | 4.563 | 19.44 | 100 |
| 7 | 4.416 | 20.09 | 32 |
| 8 | 4.231 | 20.98 | 12 |
| 9 | 3.503 | 25.41 | 64 |
| 10 | 3.408 | 26.13 | 14 |
| | Form VI: | | |
| 1 | 9.762 | 9.05 | 29 |
| 2 | 8.841 | 10.00 | 17 |
| 3 | 6.780 | 13.05 | 52 |
| 4 | 4.250 | 20.89 | 42 |
| 5 | 4.177 | 21.26 | 100 |
| 6 | 3.888 | 22.85 | 37 |
| 7 | 3.846 | 23.11 | 20 |
| 8 | 3.766 | 23.61 | 41 |
| 9 | 3.724 | 23.87 | 17 |
| 10 | 3.594 | 24.76 | 20 |
| | Form VII: | | |
| 1 | 8.472 | 10.43 | 18 |
| 2 | 6.336 | 13.97 | 10 |
| 3 | 5.476 | 16.17 | 10 |
| 4 | 4.893 | 18.12 | 9 |
| 5 | 4.664 | 19.01 | 100 |
| 6 | 4.236 | 20.96 | 30 |
| 7 | 3.676 | 24.19 | 10 |
| 8 | 3.609 | 24.65 | 71 |
| 9 | 3.561 | 24.99 | 8 |
| 10 | 3.071 | 29.05 | 16 |
| | Form VIII: | | |
| 1 | 7.656 | 11.55 | 18 |
| 2 | 6.672 | 13.26 | 34 |
| 3 | 6.538 | 13.53 | 20 |
| 4 | 5.721 | 15.48 | 20 |
| 5 | 5.244 | 16.89 | 54 |
| 6 | 4.700 | 18.87 | 25 |
| 7 | 4.475 | 19.82 | 45 |
| 8 | 4.330 | 20.49 | 34 |
| 9 | 3.745 | 23.74 | 100 |
| 10 | 3.240 | 27.50 | 20 |
| | Form IX: | | |
| 1 | 7.044 | 12.56 | 31 |
| 2 | 6.712 | 13.18 | 22 |
| 3 | 5.487 | 16.14 | 40 |
| 4 | 5.218 | 16.98 | 30 |
| 5 | 4.897 | 18.10 | 46 |
| 6 | 4.714 | 18.81 | 42 |
| 7 | 4.445 | 19.96 | 67 |
| 8 | 3.554 | 25.04 | 100 |
| 9 | 3.333 | 26.72 | 32 |
| 10 | 3.173 | 28.10 | 31 |
| | Form X: | | |
| 1 | 15.817 | 5.58 | 31 |
| 2 | 9.123 | 9.69 | 23 |
| 3 | 8.280 | 10.68 | 27 |
| 4 | 7.953 | 11.12 | 28 |
| 5 | 6.561 | 13.48 | 42 |
| 6 | 6.440 | 13.74 | 36 |
| 7 | 5.507 | 16.08 | 35 |
| 8 | 4.167 | 21.30 | 98 |

TABLE III-continued

Data of powder-XRD-pattern of polymorphic Forms.
(10 characteristic peaks of each polymorph have been taken for evaluation.
The XRD instrument is controlled for 2Theta ± 0.1°).

| No. | d (Å) | 2θ | I/I₀ |
|---|---|---|---|
| 9 | 4.132 | 21.49 | 49 |
| 10 | 3.576 | 24.88 | 100 |
| Form XI: | | | |
| 1 | 10.348 | 8.54 | 39 |
| 2 | 7.077 | 12.50 | 25 |
| 3 | 6.717 | 13.17 | 28 |
| 4 | 4.778 | 18.56 | 23 |
| 5 | 4.599 | 19.28 | 34 |
| 6 | 4.490 | 19.76 | 100 |
| 7 | 4.239 | 20.94 | 51 |
| 8 | 4.186 | 21.21 | 18 |
| 9 | 3.504 | 25.40 | 66 |
| 10 | 3.391 | 26.26 | 69 |
| Form XIII: | | | |
| 1 | 6.579 | 13.45 | 85 |
| 2 | 6.121 | 14.46 | 63 |
| 3 | 5.424 | 16.33 | 28 |
| 4 | 5.047 | 17.56 | 47 |
| 5 | 4.884 | 18.15 | 21 |
| 6 | 4.344 | 20.43 | 64 |
| 7 | 4.301 | 20.63 | 25 |
| 8 | 4.181 | 21.24 | 100 |
| 9 | 3.414 | 26.08 | 45 |
| 10 | 3.145 | 28.36 | 23 |
| Form XIV: | | | |
| 1 | 15.012 | 5.88 | 29 |
| 2 | 7.980 | 11.08 | 20 |
| 3 | 5.182 | 17.10 | 24 |
| 4 | 4.886 | 18.14 | 100 |
| 5 | 4.189 | 21.19 | 20 |
| 6 | 3.999 | 22.21 | 24 |
| 7 | 3.494 | 25.47 | 64 |
| 8* | | | |
| 9* | | | |
| 10* | | | |
| Form XV: | | | |
| 1 | 16.422 | 5.38 | 27 |
| 2 | 9.225 | 9.58 | 55 |
| 3 | 8.281 | 10.68 | 38 |
| 4 | 6.430 | 13.76 | 66 |
| 5 | 5.541 | 15.98 | 44 |
| 6 | 3.985 | 22.29 | 65 |
| 7 | 3.782 | 23.50 | 43 |
| 8 | 3.592 | 24.77 | 60 |
| 9 | 3.389 | 26.28 | 100 |
| 10 | 3.358 | 26.52 | 30 |
| Form XVI: | | | |
| 1 | 11.249 | 7.85 | 36 |
| 2 | 10.139 | 8.71 | 46 |
| 3 | 8.348 | 10.59 | 100 |
| 4 | 4.555 | 19.47 | 31 |
| 5 | 4.201 | 21.13 | 51 |
| 6 | 3.955 | 22.46 | 50 |
| 7 | 3.749 | 23.72 | 40 |
| 8 | 3.629 | 24.51 | 87 |
| 9 | 3.325 | 26.79 | 44 |
| 10 | 2.817 | 31.74 | 44 |

*Further peaks exhibit intensities < 3* noise.

The invention claimed is:

1. A compound which is 1-[4-(5-cyanoindol-3-yl)butyl]-4-(2-carbamoyl-benzofuran-5-yl)-piperazine hydrochloride solvate in its crystalline modification and having at least one group of 2Theta characteristic peak values selected from the following groups:
   i. Group A: at least three of the characteristic peak values corresponding to 10.40±0.1, 11.19±0.1, 13.39±0.1, 13.54±0.1, 13.79±0.1, 15.84±0.1, 21.09±0.1, 23.64±0.1, 24.49±0.1 or 25.79±0.1 degrees;
   ii. Group B: at least three of the characteristic peak values corresponding to 10.49±0.1, 11.73±0.1, 13.12±0.1, 14.46±0.1, 16.24±0.1, 19.32±0.1, 20.05±0.1, 21.75±0.1, 23.50±0.1, or 26.35±0.1 degrees;
   iii. Group C: at least three of the characteristic peak values corresponding to 5.38±0.1, 9.58±0.1, 10.68±0.1, 13.76±0.1, 15.98±0.1, 22.29±0.1, 23.50±0.1, 24.77±0.1, 26.28±0.1 or 26.52±0.1 degrees;
   iv. Group D: at least three of the characteristic peak values corresponding to 5.58±0.1, 9.69±0.1, 10.68±0.1, 11.12±0.1, 13.48±0.1, 13.74±0.1, 16.08±0.1, 21.30±0.1, 21.49±0.1 or 24.88±0.1 degrees;
   v. Group E: at least three of the characteristic peak values corresponding to 8.54±0.1, 12.50±0.1, 13.17±0.1, 18.56±0.1, 19.28±0.1, 19.76±0.1, 20.94±0.1, 21.21±0.1, 25.40±0.1, or 26.26±0.1 degrees; and
   vi. Group F: at least three of the characteristic peak values corresponding to 5.88±0.1, 11.08±0.1, 17.10±0.1, 18.14±0.1, 21.19±0.1, 22.21±0.1 or 25.47±0.1 degrees.

2. A compound according to claim 1 as 1-[4-(5-cyanoindol-3-yl)butyl]-4-(2-carbamoyl-benzofuran-5-yl)-piperazine hydrochloride solvate in its crystalline modification and having at least three of the characteristic peak values in Group A (Form I).

3. A compound according to claim 1 as 1-[4-(5-cyanoindol-3-yl)butyl]-4-(2-carbamoyl-benzofuran-5-yl)-piperazine hydrochloride solvate in its crystalline modification and having at least three of the characteristic peak values in Group B (Form II).

4. A compound according to claim 1 as 1-[4-(5-cyanoindol-3-yl)butyl]-4-(2-carbamoyl-benzofuran-5-yl)-piperazine hydrochloride solvate in its crystalline modification and having at least three of the characteristic peak values in Group C (Form XV).

5. A compound according to claim 1 as 1-[4-(5-cyanoindol-3-yl)butyl]-4-(2-carbamoyl-benzofuran-5-yl)-piperazine hydrochloride solvate in its crystalline modification and having at least three of the characteristic peak values in Group D (Form X).

6. A compound according to claim 1 as 1-[4-(5-cyanoindol-3-yl)butyl]-4-(2-carbamoyl-benzofuran-5-yl)-piperazine hydrochloride solvate in its crystalline modification and having at least three of the characteristic peak values in Group E (Form XI).

7. A compound according to claim 1 as 1-[4-(5-cyanoindol-3-yl)butyl]-4-(2-carbamoyl-benzofuran-5-yl)-piperazine hydrochloride solvate in its crystalline modification and having at least three of the characteristic peak values in Group F.

8. A pharmaceutical composition comprising a compound according to any one of claims 1 to 7.

9. A compound which is 1-[4-(5-cyanoindol-3-yl)butyl]-4-(2-carbamoyl-benzofuran-5-yl)-piperazine hydrochloride hydrate in its crystalline modification and having at least one group of 2Theta characteristic peak values selected from the following groups:
   i. Group A: at least three of the characteristic peak values corresponding to 9.34±0.1, 10.83±0.1, 13.00±0.1, 13.47±0.1, 18.70±0.1, 19.44±0.1, 20.09±0.1, 20.98±0.1, 25.41±0.1 or 26.13±0.1 degrees;
   ii. Group B: at least three of the characteristic peak values corresponding to 9.05±0.1, 10.00±0.1, 13.05±0.1, 20.89±0.1, 21.26±0.1, 22.85±0.1, 23.11±0.1, 23.61±0.1, 23.87±0.1, or 24.76±0.1 degrees; and iii. Group C: at least three of the characteristic peak values corresponding to 11.55±0.1, 13.26±0.1, 13.53±0.1, 15.48±0.1, 16.89±0.1, 18.87±0.1, 19.82±0.1, 20.49±0.1, 23.74±0.1 or 27.50±0.1 degrees.

10. A compound according to claim 9 as 1-[4-(5-cyanoindol-3-yl)butyl]-4-(2-carbamoyl-benzofuran-5-yl)-piperazine hydrochloride hydrate in its crystalline modification and having at least three of the characteristic peak values in Group A (Form V).

11. A compound according to claim 9 as 1-[4-(5-cyanoindol-3-yl)butyl]-4-(2-carbamoyl-benzofuran-5-yl)-piperazine hydrochloride hydrate in its crystalline modification and having at least three of the characteristic peak values in Group B.

12. A compound according to claim 9 as 1-[4-(5-cyanoindol-3-yl)butyl]-4-(2-carbamoyl-benzofuran-5-yl)-piperazine hydrochloride hydrate in its crystalline modification and having at least three of the characteristic peak values in Group C.

13. A pharmaceutical composition comprising a compound according to any one of claims 9 to 12.

14. Process for preparing Form I according to claim 2, which comprises:
   (1) dispersing 1-[4-(5-cyanoindol-3-yl)butyl]-4-(2-carbamoyl-benzofuran-5-yl)-piperazine in acetone;
   (2) converting the 1-[4-(5-cyanoindol-3-yl)butyl]-4-(2-carbamoyl-benzofuran-5-yl)-piperazine base, by addition of 1N hydrochloric acid into the hydrochloride salt at temperatures between 30° C. and the boiling point of acetone;
   (3) precipitation of Form I at room temperature; and
   (4) recovering the precipitated 1-[4-(5-cyanoindol-3-yl)butyl]-4-(2-carbamoyl-benzofuran-5-yl)-piperazine hydrochloride acetonate by filtration, and drying in vacuo at room temperature.

15. Process for preparing Form I according to claim 2 which comprises:
   (1) suspending Form III of 1-[4-(5-cyanoindol-3-yl)butyl]-4-(2-carbamoyl-benzofuran-5-yl)-piperazine hydrochloride in acetone;
   (2) stirring at room temperature between a few hours to 20 days; and
   (3) recovering the precipitated 1-[4-(5-cyanoindol-3-yl)butyl]-4-(2-carbamoyl-benzofuran-5-yl)-piperazine hydrochloride acetonate by filtration, and drying in vacuo at room temperature.

16. The process of claim 15, wherein step (2) is carried out for 10 to 20 days.

17. Process for preparing Form II according to claim 3, which comprises:
   (1) dispersing 1-[4-(5-cyanoindol-3-yl)butyl]-4-(2-carbamoyl-benzofuran-5-yl)-piperazine in tetrahydrofuran;
   (2) converting the 1-[4-(5-cyanoindol-3-yl)butyl]-4-(2-carbamoyl-benzofuran-5-yl)-piperazine base, by addition of 1N hydrochloric acid into the hydrochloride salt at temperatures between 10° C. and 60° C.;
   (3) precipitation of Form II at room temperature; and
   (4) recovering the precipitated 1-[4-(5-cyanoindol-3-yl)butyl]-4-(2-carbamoyl-benzofuran-5-yl)-piperazine hydrochloride solvate with tetrahydrofuran by filtration, and drying in vacuo at room temperature.

18. Process for preparing Form II according to claim 3 which comprises:
   (1) suspending Form III of 1-[4-(5-cyanoindol-3-yl)butyl]-4-(2-carbamoyl-benzofuran-5-yl)-piperazine hydrochloride in tetrahydrofuran;
   (2) stirring at room temperature between a few hours to 30 days; and
   (3) recovering the precipitated 1-[4-(5-cyanoindol-3-yl)butyl]-4-(2-carbamoyl-benzofuran-5-yl)-piperazine hydrochloride tetrahydrofuran by filtration, and drying in vacuo at room temperature.

19. The process of claim 18, wherein step (2) is carried out for 15 to 30 days.

20. Process for preparing Form XV according to claim 4, which comprises:
   (1) dispersing 1-[4-(5-cyanoindol-3-yl)butyl]-4-(2-carbamoyl-benzofuran-5-yl)-piperazine in tetrahydrofuran;
   (2) converting the 1-[4-(5-cyanoindol-3-yl)butyl]-4-(2-carbamoyl-benzofuran-5-yl)-piperazine base, by addition of 1N hydrochloric acid into the hydrochloride salt at temperatures between −10° C. and 10° C.;
   (3) precipitation of Form XV at room temperature; and
   (4) recovering the precipitated 1-[4-(5-cyanoindol-3-yl)butyl]-4-(2-carbamoyl-benzofuran-5-yl)-piperazine hydrochloride solvate with tetrahydrofuran by filtration, and drying in vacuo at room temperature.

21. Process for preparing Form X according to claim 5, which comprises:
   (1) dispersing 1-[4-(5-cyanoindol-3-yl)butyl]-4-(2-carbamoyl-benzofuran-5-yl)-piperazine in tetrahydrofuran;
   (2) converting the 1-[4-(5-cyanoindol-3-yl)butyl]-4-(2-carbamoyl-benzofuran-5-yl)-piperazine base, by addition of 1N hydrochloric acid into the hydrochloride salt at temperatures between 10° C. and 40° C.;
   (3) precipitation of Form II at room temperature; and
   (4) recovering the precipitated 1-[4-(5-cyanoindol-3-yl)butyl]-4-(2-carbamoyl-benzofuran-5-yl)-piperazine hydrochloride solvate with tetrahydrofuran by filtration, and drying at temperatures up to 80° C. maximum.

22. Process for preparing Form XI according to claim 6, which comprises:
   (1) suspending Form VI of 1-[4-(5-cyanoindol-3-yl)butyl]-4-(2-carbamoyl-benzofuran-5-yl)-piperazine hydrochloride in methanol at temperatures between 55° C. and the boiling point of methanol;
   (2) cooling down the reaction mixture to temperatures between −40° and −10° C.; and
   (3) recovering the precipitated 1-[4-(5-cyanoindol-3-yl)butyl]-4-(2-carbamoyl-benzofuran-5-yl)-piperazine hydrochloride methanolate by filtration at room temperature, and drying in vacuo at room temperature.

23. Process for preparing Form V according to claim 10, which comprises:
   (1) dispersing 1-[4-(5-cyanoindol-3-yl)butyl]-4-(2-carbamoyl-benzofuran-5-yl)-piperazine in tetrahydrofuran;
   (2) converting the 1-[4-(5-cyanoindol-3-yl)butyl]-4-(2-carbamoyl-benzofuran-5-yl)-piperazine base, by addition of aqueous hydrochloric acid into the hydrochloride salt;
   (3) precipitation of Form V at room temperature; and
   (4) recovering the precipitated 1-[4-(5-cyanoindol-3-yl)butyl]-4-(2-carbamoyl-benzofuran-5-yl)-piperazine hydrochloride monohydrate by filtration, and drying in vacuo at room temperature.

24. A method of the treatment of depressive disorders, anxiety disorders, bipolar disorders, mania, dementia, substance-related disorders, sexual dysfunctions, eating disorders, obesity, fibromyalgia, sleeping disorders, psychiatric disorders, cerebral infarct, tension, for the therapy of side-effects in the treatment of hypertension, cerebral disorders, chronic pain, acromegaly, hypogonadism, secondary amenorrhea, premenstrual syndrome and undesired puerperal lactation comprising the step of adminstering to a subject an effective amount of a compound according to any one of claims 1-7.

25. A method for the treatment of depressive disorders, anxiety disorders, bipolar disorders, mania, dementia, substance-related disorders, sexual dysfunctions, eating disorders, obesity, fibromyalgia, sleeping disorders, psychiatric disorders, cerebral infarct, tension, for the therapy of side-effects in the treatment of hypertension, cerebral disorders, chronic pain, acromegaly, hypogonadism, secondary amenorrhea, premenstrual syndrome and undesired puerperal lactation comprising the step of administering to a subject an effective amount of a compound according to any one of claims 9-12.

26. A method for the treatment of depressive disorders comprising the step of administering to a subject an effective amount of a compound according to any one of claims 1-7.

27. A method for the treatment of depressive disorders comprising the step of administering to a subject an effective amount of a compound according to any one of claims 9-12.

* * * * *